United States Patent
Shao et al.

(10) Patent No.: US 8,754,117 B2
(45) Date of Patent: *Jun. 17, 2014

(54) PYRROLIDINE TRIPLE REUPTAKE INHIBITORS

(71) Applicant: Sunovion Pharmaceuticals Inc., Marlborough, MA (US)

(72) Inventors: Liming Shao, Lincoln, MA (US); Jianguo Ma, Natick, MA (US)

(73) Assignee: Sunovion Pharmaceuticals Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/752,086

(22) Filed: Jan. 28, 2013

(65) Prior Publication Data

US 2013/0137744 A1 May 30, 2013

Related U.S. Application Data

(63) Continuation of application No. 13/148,467, filed as application No. PCT/US2010/023344 on Feb. 5, 2010, now Pat. No. 8,389,559.

(60) Provisional application No. 61/151,167, filed on Feb. 9, 2009.

(51) Int. Cl.
*A61K 31/4025* (2006.01)
*A61K 31/40* (2006.01)
*C07D 207/06* (2006.01)
*C07D 207/08* (2006.01)
*C07D 405/04* (2006.01)

(52) U.S. Cl.
USPC ............ 514/422; 514/428; 548/517; 548/577

(58) Field of Classification Search
None
See application file for complete search history.

(56) References Cited

U.S. PATENT DOCUMENTS

| 6,362,201 | B1 | 3/2002 | Baker et al. | |
|---|---|---|---|---|
| 8,389,559 | B2 * | 3/2013 | Shao et al. | 514/408 |
| 2002/0183306 | A1 | 12/2002 | Howard | |
| 2006/0270713 | A1 | 11/2006 | Beadle et al. | |

OTHER PUBLICATIONS

International Search Report dated Mar. 29, 2012 in PCT/US2010/023344.

* cited by examiner

*Primary Examiner* — Michael Barker
(74) *Attorney, Agent, or Firm* — Choate, Hall & Stewart LLP

(57) ABSTRACT

In various embodiments, the present invention provides cycloalkyl pyrrolidine compounds and methods for their use in the treatment and/or prevention of various diseases, conditions and syndromes, including central nervous system (CNS) disorders, such as depression, anxiety, schizophrenia and sleep disorder as well as methods for their synthesis. The invention also relates to pharmaceutical compositions containing the compounds of the invention, as well as methods of inhibiting reuptake of endogenous monoamines, such as dopamine, serotonin and norepinephrine from the synaptic cleft and methods of modulating one or more monoamine transporter.

26 Claims, No Drawings

PYRROLIDINE TRIPLE REUPTAKE INHIBITORS

CROSS-REFERENCE TO RELATED APPLICATIONS

This application is a continuation of U.S. application Ser. No. 13/148,467, filed on Sep. 27, 2011, which is a §371 national phase application of International Patent Application No. PCT/US2010/023344, filed Feb. 5, 2010, which claims priority to U.S. Provisional Application No. 61/151,167, filed on Feb. 9, 2009, the disclosure of all of which are incorporated herein by reference in their entireties for all purposes.

FIELD OF THE INVENTION

In various embodiments, the invention relates to compounds and compositions for the treatment of central nervous system (CNS) disorders.

BACKGROUND OF THE INVENTION

Psychiatric disorders are pathological conditions of the brain characterized by identifiable symptoms that result in abnormalities in cognition, emotion, mood, or affect. These disorders may vary in severity of symptoms, duration, and functional impairment. Psychiatric disorders afflict millions of people worldwide resulting in tremendous human suffering and economic burden due to lost productivity and dependent care.

Over the past several decades, the use of pharmacological agents to treat psychiatric disorders has greatly increased, largely due to research advances in both neuroscience and molecular biology. In addition, chemists have become increasingly sophisticated at creating chemical compounds that are more effective therapeutic agents with fewer side effects, targeted to correct the biochemical alterations that accompany mental disorders.

Yet, despite the many advances that have occurred, many psychiatric diseases remain untreated or inadequately treated with current pharmaceutical agents. In addition, many of the current agents interact with molecular targets not involved with the psychiatric disease. This indiscriminate binding can result in side effects that can greatly influence the overall outcome of therapy. In some cases the side effects are so severe that discontinuation of therapy is required.

Depression is an affective disorder, the pathogenesis of which cannot be explained by any single cause or theory. It is characterized by a persistently low mood or diminished interests in one's surroundings, accompanied by at least one of the following symptoms: reduced energy and motivation, difficulty concentrating, altered sleep and appetite, and at times, suicidal ideation (American Psychiatric Association: *Diagnostic and Statistical Manual of Mental Disorders*, ed. 4. Washington, American Psychiatric Association, 1994). Major depression is associated with high rates of morbidity and mortality, with suicide rates of 10-25% (Kaplan H I, Sadock B J (eds): *Synopsis of Psychiatry*. Baltimore, Williams & Wilkins, 1998, p. 866). The compounds of the invention may also be used to reduce fatigue commonly associated with depression (see, for example, "Bupropion augmentation in the treatment of chronic fatigue syndrome with coexistent major depression episode" Schonfeldt-Lecuona et al., *Pharmacopsychiatry* 39(4):152-4, 2006; "Dysthymia: clinical picture, extent of overlap with chronic fatigue syndrome, neuropharmacological considerations, and new therapeutic vistas" Brunello et al., *J. Affect. Disord.* 52(1-3):275-90, 1999; "Chronic fatigue syndrome and seasonal affective disorder: comorbidity, diagnostic overlap, and implications for treatment" Terman et al., *Am. J. Med.* 105(3A):115S-124S, 1998.).

Depression is believed to result from dysfunction in the noradrenergic or serotonergic systems, more specifically, from a deficiency of certain neurotransmitters (NTs) at functionally important adrenergic or serotonergic receptors.

Neurotransmitters produce their effects as a consequence of interactions with specific receptors. Neurotransmitters, including norepinephrine (NE) and/or serotonin (5-hydroxytryptamine, or 5-HT), are synthesized in brain neurons and stored in vesicles. Upon a nerve impulse, NTs are released into the synaptic cleft, where they interact with various postsynaptic receptors. Regional deficiencies in the synaptic levels of 5-HT and/or NE are believed to be involved in the etiology of depression, wakefulness, and attention.

Norepinephrine is involved in regulating arousal, dreaming, and moods. Norepinephrine can also contribute to the regulation of blood pressure, by constricting blood vessels and increasing heart rate.

Serotonin (5-HT) is implicated in the etiology or treatment of various disorders. The most widely studied effects of 5-HT are those on the CNS. The functions of 5-HT are numerous and include control of appetite, sleep, memory and learning, temperature regulation, mood, behavior (including sexual and hallucinogenic behavior), cardiovascular function, smooth muscle contraction, and endocrine regulation. Peripherally, 5-HT appears to play a major role in platelet homeostasis and motility of the GI tract. The actions of 5-HT are terminated by three major mechanisms: diffusion; metabolism; and reuptake. The major mechanism by which the action of 5-HT is terminated is by reuptake through presynaptic membranes. After 5-HT acts on its various postsynaptic receptors, it is removed from the synaptic cleft back into the nerve terminal through an uptake mechanism involving a specific membrane transporter in a manner similar to that of other biogenic amines. Agents that selectively inhibit this uptake increase the concentration of 5-HT at the postsynaptic receptors and have been found to be useful in treating various psychiatric disorders, particularly depression.

Approaches to the treatment of depression over the years have involved the use of agents that increase the levels of NE and 5-HT, either by inhibiting their metabolism (e.g., monoamine oxidase inhibitors) or reuptake (e.g., tricyclic antidepressants or selective serotonin reuptake inhibitors (SSRIs)).

There are more than twenty approved antidepressant drugs available in the United States. The classical tricyclic antidepressants (TCAs) currently available block primarily the uptake of NE and also, to varying degrees, the uptake of 5-HT, depending on whether they are secondary or tertiary amines. Tertiary amines such as imipramine and amitriptyline are more selective inhibitors of the uptake of 5-HT than of catecholamines, compared with secondary amines such as desipramine.

Selective serotonin reuptake inhibitors have been investigated as potential antidepressants. Fluoxetine (PROZAC®), sertraline (ZOLOFT®), and paroxetine (PAXIL®) are three examples of SSRIs currently on the U.S. market. These agents do not appear to possess greater efficacy than the TCAs, nor do they generally possess a faster onset of action; however, they do have the advantage of causing less side-effects. Of these three SSRIs, paroxetine is the most potent inhibitor of 5-HT uptake, fluoxetine the least. Sertaline is the most selective for 5-HT versus NE uptake, fluoxetine the least selective.

Fluoxetine and sertraline produce active metabolites, while paroxetine is metabolized to inactive metabolites. The SSRIs, in general, affect only the uptake of serotonin and display little or no affinity for various receptor systems including muscarinic, adrenergic, dopamine, and histamine receptors.

In addition to treating depression, several other potential therapeutic applications for SSRIs have been investigated. They include treatment of Alzheimer's disease, aggressive behavior, premenstrual syndrome, diabetic neuropathy, chronic pain, fibromyalgia, and alcohol abuse. For example, fluoxetine is approved for the treatment of obsessive-compulsive disorder (OCD). Of particular significance is the observation that 5-HT reduces food consumption by increasing meal-induced satiety and reducing hunger, without producing the behavioral effects of abuse liability associated with amphetamine-like drugs. Thus, there is interest in the use of SSRIs in the treatment of obesity.

Venlafaxine (EFFEXOR®) is a dual-reuptake antidepressant that differs from the classical TCAs and the SSRIs chemically and pharmacologically in that it acts as a potent inhibitor of both 5-HT and NE uptake. Neither venlafaxine nor its major metabolite has a significant affinity for adrenergic alpha-1 receptors. Venlafaxine possesses an efficacy equivalent to that of the TCAs, and a benign side effect profile similar to those of the SSRIs.

Dopamine is hypothesized to play a major role in psychosis and certain neurodegenerative diseases, such as Parkinson's disease, where a deficiency in dopaminergic neurons is believed to be the underlying pathology. Dopamine affects brain processes that control movement, emotional response, and ability to experience pleasure and pain. Regulation of DA plays a crucial role in our mental and physical health. Certain drugs increase DA concentrations by preventing DA reuptake, leaving more DA in the synapse. An example is methylphenidate (RITALIN®), used therapeutically to treat childhood hyperkinesias and symptoms of schizophrenia. Dopamine abnormalities are believed to underlie some of the core attentional abnormalities seen in acute schizophrenics.

A therapeutic lag is associated with the use of these drugs. Patients must take a drug for at least three (3) weeks before achieving clinically meaningful symptom relief. Furthermore, a significant number of patients do not respond to current therapies at all. For example, it is currently estimated that up to thirty percent (30%) of clinically diagnosed cases of depression are resistant to all forms of drug therapy.

SUMMARY OF THE INVENTION

In various embodiments, the present invention relates to novel cycloalkylamines and salts thereof. It further relates to novel pharmaceutical compositions, and their use in the treatment of CNS and other disorders, e.g., depression (e.g., major depressive disorder, bipolar disorder), fibromyalgia, pain (e.g., neuropathic pain), sleep apnea, attention deficit disorder (ADD), attention deficit hyperactivity disorder (ADHD), restless leg syndrome, schizophrenia, anxiety, obsessive compulsive disorder, posttraumatic stress disorder, seasonal affective disorder (SAD), premenstrual dysphoria as well as neurodegenerative disease (e.g., Parkinson's disease, Alzheimer's disease) and seizures.

Exemplary compounds of the invention have a structure according to Formula (I):

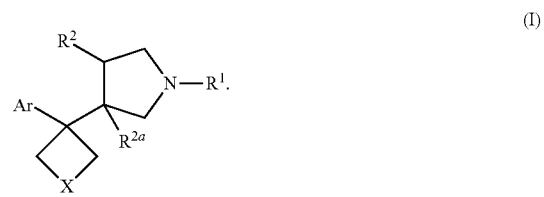

In Formula I, the symbol $R^1$ represents H, $C_1$-$C_3$ substituted or unsubstituted alkyl or $C_1$-$C_3$ substituted or unsubstituted heteroalkyl. The symbols $R^2$ and $R^{2a}$ independently represent H, $C_1$-$C_3$ substituted or unsubstituted alkyl, $C_1$-$C_3$ substituted or unsubstituted heteroalkyl, or $OR^3$. $R^3$ is selected from H, $C_1$-$C_3$ substituted or unsubstituted alkyl and $C_1$-$C_3$ substituted or unsubstituted heteroalkyl. Ar is an aryl group. Exemplary of Ar groups of use in the compound of the invention are substituted or unsubstituted naphthyl and substituted or unsubstituted phenyl. The symbol X represents:

—$CH_2$—; —$CH_2CH_2$—; or —$CH_2ZCH_2$— wherein Z is a member selected from:

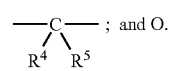; and O.

$R^4$ and $R^5$ independently represent H, $C_1$-$C_3$ substituted or unsubstituted alkyl, $C_1$-$C_3$ substituted or unsubstituted heteroalkyl, or $OR^6$. $R^6$ is H, $C_1$-$C_3$ substituted or unsubstituted alkyl or $C_1$-$C_3$ substituted or unsubstituted heteroalkyl.

Any salt, solvate, enantiomer, diastereomer, racemic mixture, enantiomerically enriched mixture, and enantiomerically pure form of the above described compounds falls within the scope of the invention. In an exemplary embodiment, the invention provides a pharmaceutically acceptable salt, solvate, enantiomer, diastereomer, racemic mixture, enantiomerically enriched mixture, or enantiomerically pure form of a compound according to Formula I.

In an exemplary embodiment, the invention provides a pharmaceutical composition including a compound of the invention (or a pharmaceutically acceptable salt, solvate, etc.) thereof, and a pharmaceutically acceptable carrier.

The invention also provides method of using the compounds according to Formula I. For example, the invention provides a method of inhibiting binding of a monoamine transporter ligand to a monoamine transporter, such as serotonin transporter, dopamine transporter and norepinephrine transporter. An exemplary method includes contacting the monoamine transporter and a compound of the invention. In an exemplary embodiment the monoamine transporter ligand is a monoamine, such as serotonin, dopamine and norepinephrine.

In various embodiments, the invention provides a method of inhibiting the activity of at least one monoamine transporter, such as serotonin transporter, dopamine transporter and norepinephrine transporter. Exemplary methods include contacting the monoamine transporter and a compound of the invention.

Furthermore, in an exemplary embodiment, the invention provides a method of inhibiting uptake of at least one monoamine, such as serotonin, dopamine and norepinephrine, by a cell. An exemplary method includes contacting the cell with a compound of the invention. In an exemplary embodiment, the cell is a brain cell, such as a neuronal cell or a glial cell.

In various embodiments, the invention provides a method of treating depression by inhibiting the activity at least one monoamine transporter. The method includes administering to a mammalian subject a compound of the invention. Exemplary compound of the invention inhibit the activity of at least two different monoamine transporters. In an exemplary embodiment, the mammalian subject is a human.

The invention also provides a method of treating a central nervous system disorder. The method includes administering to a subject in need thereof a therapeutically effective amount of a compound of the invention or a pharmaceutically acceptable salt or solvate thereof. In an exemplary embodiment, the subject is a human.

Other embodiments, objects and advantages of the present invention are set forth in the detailed description below.

DETAILED DESCRIPTION OF THE INVENTION

I. Definitions

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, optionally includes those derivatives of alkyl defined in more detail below, such as "heteroalkyl." Alkyl groups that are limited to hydrocarbon groups are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$CO_2R'$— represents both —C(O)OR' and —OC(O)R'.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, S, Si and B, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) optionally includes both aryl and heteroaryl rings as defined above. Thus, the term "arylalkyl" can include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") optionally include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: substituted or unsubstituted alkyl, substituted or unsubstituted heteroalkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: substituted or unsubstituted alkyl, substituted or unsubstituted heteroalkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R' and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$-D-, wherein A and D are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X" is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$)alkyl.

As used herein, the term "acyl" describes a substituent containing a carbonyl residue, C(O)R. Exemplary species for R include H, halogen, substituted or unsubstituted alkyl, substituted or unsubstituted aryl, substituted or unsubstituted heteroaryl, and substituted or unsubstituted heterocycloalkyl.

As used herein, the term "fused ring system" means at least two rings, wherein each ring has at least 2 atoms in common with another ring. "Fused ring systems may include aromatic as well as non aromatic rings. Examples of "fused ring systems" are naphthalenes, indoles, quinolines, chromenes and the like.

As used herein, the term "heteroatom" includes oxygen (O), nitrogen (N), sulfur (S), silicon (Si) and boron (B).

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, and substituted or unsubstituted heterocycloalkyl groups.

The phrase "therapeutically effective amount" as used herein means that amount of a compound, or composition comprising a compound of the present invention which is effective for producing some desired therapeutic effect (e.g., by inhibiting uptake of a monoamine from the synaptic cleft of a mammal, thereby modulating the biological consequences of that pathway in the treated organism) at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in human beings and animals without excessive toxicity, irritation, allergic response, or other problem or complication, commensurate with a reasonable benefit/risk ratio.

The phrase "pharmaceutically acceptable carrier" as used herein means any pharmaceutically acceptable material, which may be liquid or solid. Exemplary carriers include vehicles, diluents, additives, liquid and solid fillers, excipients, solvents, solvent encapsulating materials. Each carrier must be "acceptable" in the sense of being compatible with the other ingredients of the formulation and not injurious to the patient. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set forth herein, certain embodiments of the present compounds may contain a basic functional group, e.g., amino or alkylamino, or an acidic functional group, e.g., a carboxylic- or sulfonic acid and are, thus, capable of forming pharmaceutically acceptable salts with pharmaceutically acceptable acids or bases, respectively. The term "pharmaceutically acceptable salts" in this respect, refers to the relatively nontoxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, sulfamate, bisulfate, phosphate, nitrate, acetate, valerate, oleate, palmitate, stearate, laurate, benzoate, lactate, tosylate, citrate, maleate, ascorbate, palmitate, fumarate, succinate, tartrate, napthylate, mesylate, hydroxymaleate, phenylacetate, glutamate, glucoheptonate, salicyclate, sulfanilate, 2-acetoxybenzoate, methanesulfonate, ethane disulfonate, oxalate, isothionate, lactobionate, and laurylsulphonate salts and the like. When the compound of the invention includes an acidic group, appropriate salts are formed from substituted or unsubstituted alkyl, heteroalky and aryl amines. See, for example, Berge et al. (1977) "Pharmaceutical Salts", *J. Pharm. Sci.* 66:1-19.

The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science*, 66: 1-19 (1977)). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention. "Compound or a pharmaceutically acceptable salt or solvate of a compound" intends the inclusive meaning of "or", in that a material that is both a salt and a solvate is encompassed.

Certain compounds of the present invention possess asymmetric carbon atoms (optical centers) or double bonds; the racemates, diastereomers, geometric isomers and individual isomers are encompassed within the scope of the present invention. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

The graphic representations of racemic, ambiscalemic and scalemic or enantiomerically pure compounds used herein are taken from Maehr, *J. Chem. Ed.*, 62: 114-120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but not implying any absolute stereochemistry; and wedge outlines and dotted or broken lines denote enantiomerically pure compounds of indeterminate absolute configuration.

As used herein, the term "enantiomerically enriched" or "diastereomerically enriched" refers to a compound having an enantiomeric excess (ee) or a diastereomeric excess (de) greater than about 50%, preferably greater than about 70% and more preferably greater than about 90%. In general, higher than about 90% enantiomeric or diastereomeric purity is particularly preferred, e.g., those compositions with greater than about 95%, greater than about 97% and greater than about 99% ee or de.

The terms "enantiomeric excess" and "diastereomeric excess" are used interchangeably herein. Compounds with a single stereocenter are referred to as being present in "enantiomeric excess", those with at least two stereocenters are referred to as being present in "diastereomeric excess".

For example, the term "enantiomeric excess" is well known in the art and is defined as:

$$ee_a = \left(\frac{conc.\ of\ a - conc.\ of\ b}{conc.\ of\ a + conc.\ of\ b}\right) \times 100$$

The term "enantiomeric excess" is related to the older term "optical purity" in that both are measures of the same phenomenon. The value of ee will be a number from 0 to 100, zero being racemic and 100 being enantiomerically pure. A compound which in the past might have been called 98% optically pure is now more precisely characterized by 96% ee. A 90% ee reflects the presence of 95% of one enantiomer and 5% of the other(s) in the material in question.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

The term "monoamine transporter ligand" refers to any compound, which binds to a monoamine transporter. Ligands include endogenous monoamines, which are the natural ligands for a given monoamine transporter as well as drug molecules and other compounds, such as synthetic molecules known to bind to a particular monoamine transporter. In one example, the ligand includes a radioisotope, such as tritium or is otherwise (e.g., fluorescently) labeled. It is within the abilities of a skilled person to select an appropriate ligand for a given monoamine transporter. For example, known ligands for the dopamine transporter include dopamine and WIN35428, known ligands for the serotonin transporter include 5-hydroxytryptamine (serotonin) and citalopram, and ligands for the norepinephrine transporter include norepinephrine and nisoxetinc.

The term "central nervous system disorder" refers to any abnormal condition of the central nervous system of a mammal. Central nervous system disorder includes neurodegenerative diseases such Alzheimer's disease and Parkinson's disease, neuropsychiatric diseases (e.g., schizophrenia), anxieties, sleep disorders, depression, dementias, movement disorders, psychoses, alcoholism, post-traumatic stress disorder and the like. "Central nervous system disorder" also includes any condition associated with the disorder, such as loss of memory and/or loss of cognition. For instance, a method of treating a neurodegenerative disease would also include treating or preventing loss of neuronal function characteristic of such disease. "Central nervous system disorder" also includes any disease or condition that is implicated, at least in part, in monoamine (e.g., norepinephrine) signaling pathways (e.g., cardiovascular disease).

The term "neurological disorder" refers to any condition of the central or peripheral nervous system of a mammal. The term "neurological disorder" includes neurodegenerative diseases (e.g., Alzheimer's disease, Parkinson's disease and amyotrophic lateral sclerosis), neuropsychiatric diseases (e.g. Schizophrenia and anxieties, such as general anxiety disorder). Exemplary neurological disorders include MLS (cerebellar ataxia), Huntington's disease, Down syndrome, multi-infarct dementia, status epilecticus, contusive injuries (e.g. spinal cord injury and head injury), viral infection induced neurodegeneration, (e.g. AIDS, encephalopathies), epilepsy, benign forgetfulness, closed head injury, sleep disorders, depression (e.g., bipolar disorder), dementias, movement disorders, psychoses, alcoholism, post-traumatic stress disorder and the like. "Neurological disorder" also includes any condition associated with the disorder. For instance, a method of treating a neurodegenerative disorder includes methods of treating loss of memory and/or loss of cognition associated with a neurodegenerative disorder. Such method would also include treating or preventing loss of neuronal function characteristic of neurodegenerative disorder.

"Pain" is an unpleasant sensory and emotional experience. Pain classifications have been based on duration, etiology or pathophysiology, mechanism, intensity, and symptoms. The term "pain" as used herein refers to all categories of pain, including pain that is described in terms of stimulus or nerve response, e.g., somatic pain (normal nerve response to a noxious stimulus) and neuropathic pain (abnormal response of a injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, AIDS pain, arthropathy, migraine, trigeminal neuralgia, cardiac ischaemia, and diabetic neuropathy (see, e.g., Harrison's Principles of Internal Medicine, pp. 93-98 (Wilson et al., eds., 12th ed. 1991); Williams et al., *J. of Med. Chem.* 42: 1481-1485 (1999), herein each incorporated by reference in their entirety). "Pain" is also meant to include mixed etiology pain, dual mechanism pain, allodynia, causalgia, central pain, hyperesthesia, hyperpathia, dysesthesia, and hyperalgesia.

"Somatic" pain, as described above, refers to a normal nerve response to a noxious stimulus such as injury or illness, e.g., trauma, burn, infection, inflammation, or disease process such as cancer, and includes both cutaneous pain (e.g., skin, muscle or joint derived) and visceral pain (e.g., organ derived).

"Neuropathic pain" is a heterogeneous group of neurological conditions that result from damage to the nervous system. "Neuropathic" pain, as described above, refers to pain resulting from injury to or dysfunctions of peripheral and/or central sensory pathways, and from dysfunctions of the nervous system, where the pain often occurs or persists without an obvious noxious input. This includes pain related to peripheral neuropathies as well as central neuropathic pain. Common types of peripheral neuropathic pain include diabetic neuropathy (DN or DPN), post-herpetic neuralgia (PHN), and trigeminal neuralgia (TGN). Central neuropathic pain, involving damage to the brain or spinal cord, can occur following stroke, spinal cord injury, and as a result of multiple sclerosis.

Common clinical features of neuropathic pain include sensory loss, allodynia (non-noxious stimuli produce pain), hyperalgesia and hyperpathia (delayed perception, summation, and painful aftersensation). Pain is often a combination of nociceptive and neuropathic types, for example, mechanical spinal pain and radiculopathy or myelopathy.

"Acute pain", is the normal, predicted physiological response to a noxious chemical, thermal or mechanical stimulus typically associated with invasive procedures, trauma and disease. It is generally time-limited, and may be viewed as an appropriate response to a stimulus that threatens and/or produces tissue injury. "Acute pain", as described above, refers to pain which is marked by short duration or sudden onset.

"Chronic pain" occurs in a wide range of disorders, for example, trauma, malignancies and chronic inflammatory diseases such as rheumatoid arthritis. Chronic pain usually lasts more than about six months. In addition, the intensity of chronic pain may be disproportionate to the intensity of the noxious stimulus or underlying process. "Chronic pain", as described above, refers to pain associated with a chronic disorder, or pain that persists beyond resolution of an underlying disorder or healing of an injury, and that is often more intense than the underlying process would predict. It may be subject to frequent recurrence.

"Inflammatory pain" is pain in response to tissue injury and the resulting inflammatory process. Inflammatory pain is adaptive in that it elicits physiologic responses that promote healing. However, inflammation may also affect neuronal function. Inflammatory mediators, including $PGE_2$ induced by the COX2 enzyme, bradykinins, and other substances, bind to receptors on pain-transmitting neurons and alter their function, increasing their excitability and thus increasing pain sensation. Much chronic pain has an inflammatory component. "Inflammatory pain", as described above, refers to pain which is produced as a symptom or a result of inflammation or an immune system disorder.

"Visceral pain", as described above, refers to pain which is located in an internal organ.

"Mixed etiology" pain, as described above, refers to pain that contains both inflammatory and neuropathic components.

"Dual mechanism" pain, as described above, refers to pain that is amplified and maintained by both peripheral and central sensitization.

"Causalgia", as described above, refers to a syndrome of sustained burning, allodynia, and hyperpathia after a traumatic nerve lesion, often combined with vasomotor and sudomotor dysfunction and later trophic changes.

"Central" pain, as described above, refers to pain initiated by a primary lesion or dysfunction in the central nervous system.

"Hyperesthesia", as described above, refers to increased sensitivity to stimulation, excluding the special senses.

"Hyperpathia", as described above, refers to a painful syndrome characterized by an abnormally painful reaction to a stimulus, especially a repetitive stimulus, as well as an increased threshold. It may occur with allodynia, hyperesthesia, hyperalgesia, or dysesthesia.

"Dysesthesia", as described above, refers to an unpleasant abnormal sensation, whether spontaneous or evoked. Special cases of dysesthesia include hyperalgesia and allodynia, "Hyperalgesia", as described above, refers to an increased response to a stimulus that is normally painful. It reflects increased pain on suprathreshold stimulation.

"Allodynia", as described above, refers to pain due to a stimulus that does not normally provoke pain.

The term "convulsion" refers to a CNS disorder and is used interchangeably with "seizure," although there are many types of seizure, some of which have subtle or mild symptoms instead of convulsions. Seizures of all types may be caused by disorganized and sudden electrical activity in the brain. Convulsions are when a person's body shakes rapidly and uncontrollably. During convulsions, the person's muscles contract and relax repeatedly. If a person has recurring seizures, and there are no underlying causes that can be identified, that person is said to have epilepsy.

The term "depression" includes all forms of depression, which include major depressive disorder (MDD), bipolar disorder, seasonal affective disorder (SAD) and dysthymia. "Major depressive disorder" is used herein interchangeably with "unipolar depression" and "major depression. "Depression" also includes any condition commonly associated with depression, such as all forms of fatigue (e.g., chronic fatigue syndrom) and cognitive deficits.

II. Introduction

One strategy to develop effective therapies is the use of broad spectrum compounds (e.g., antidepressants) that simultaneously inhibit the reuptake of more than one biogenic amine, such as serotonin (5-HT), norepinephrine (NE) and dopamine (DA). The rationale for this approach is based upon clinical and preclinical evidence showing that deficiencies in dopaminergic function can be correlated with anhedonia, which is a core symptom of depression. Baldessarini, R. J., "Drugs and the Treatment of Psychiatric Disorders: Depression and Mania, in Goodman and Gilman's The Pharmacological Basis of Therapeutics 431-459 ($9^{th}$ ed 1996) Hardman et al. eds.

An exemplary advantage of selected compounds and compositions of the present invention is their ability to increase synaptic availability of at least two, or three, neurotransmitters (e.g, NE, 5-HT and DA) by inhibiting their (re)uptake from the synaptic cleft. Skolnick and coworkers report on a body of preclinical evidence suggesting that the therapeutic profile of an antidepressant concurrently increasing the synaptic availability of DA, NE and 5-HT will differ from a compound inhibiting only NE and/or 5-HT. Skolnick, P. et al., "Antidepressant-like actions of DOV-21,947: a "triple" reuptake inhibitor," Eur. J. Pharm. 2003, 461, 103.

For example, Skolnick and coworkers have reported that a compound, DOV 21,947 ((+)-1-(3,4-dichlorophenyl)-3-azabicyclo[3.1.0]hexane), inhibits the reuptake of serotonin, norepinephrine, and dopamine in human embryonic kidney (HEK293) cells expressing the corresponding human recombinant transporters ($IC_{50}$ values of 12, 23 and 96 nM, respectively). Skolnick, P. et al., "Antidepressant-like actions of DOV-21,947: a "triple" reuptake inhibitor," Eur. J. Pharm. 2003, 461, 99. In addition, DOV 21,947 reduces the duration of immobility in the forced swim test (in rats) and also produces a dose-dependent reduction in immobility in the tail suspension test. Additional evidence can be found in preclinical data for new triple reuptake inhibitors such as DOV 21,947 in, e.g., U.S. Pat. No. 6,372,919, wherein DOV 21,947 was disclosed as having a significantly greater affinity for the norepinephrine and serotonin uptake sites than the racemic compound, (±)-1-(3,4-dichlorophenyl)-3-azabicyclo[3.1.0] hexane.

Taken together, the preclinical data for compounds such as DOV 21,947 indicate that dual or triple reuptake inhibitors form the basis of novel treatments for CNS (e.g., depression) and other disorders in the clinic.

III. Compositions

A. Pyrrolidine Cycloalkyl Amines

In an exemplary embodiment, the invention provides a compound having a structure according to Formula (I):

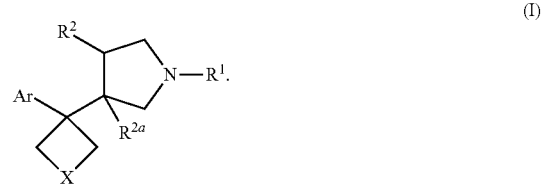

In Formula I, the symbol $R^1$ represents H, $C_1$-$C_3$ substituted or unsubstituted alkyl or $C_1$-$C_3$ substituted or unsubstituted heteroalkyl. The symbols $R^2$ and $R^{2a}$ independently represent H, $C_1$-$C_3$ substituted or unsubstituted alkyl, $C_1$-$C_3$ substituted or unsubstituted heteroalkyl, or $OR^3$. $R^3$ is selected from H, $C_1$-$C_3$ substituted or unsubstituted alkyl and $C_1$-$C_3$ substituted or unsubstituted heteroalkyl. Ar is an aryl group, particularly a member selected from substituted or unsubstituted naphthyl and substituted or unsubstituted phenyl. The symbol X represents:

—CH$_2$—; —CH$_2$CH$_2$—; or —CH$_2$ZCH$_2$— wherein Z is a member selected from:

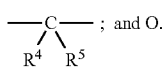; and O.

$R^4$ and $R^5$ independently represent H, $C_1$-$C_3$ substituted or unsubstituted alkyl, $C_1$-$C_3$ substituted or unsubstituted heteroalkyl, or $OR^6$. $R^6$ is H, $C_1$-$C_3$ substituted or unsubstituted alkyl or $C_1$-$C_3$ substituted or unsubstituted heteroalkyl.

Exemplary compounds of the invention include:

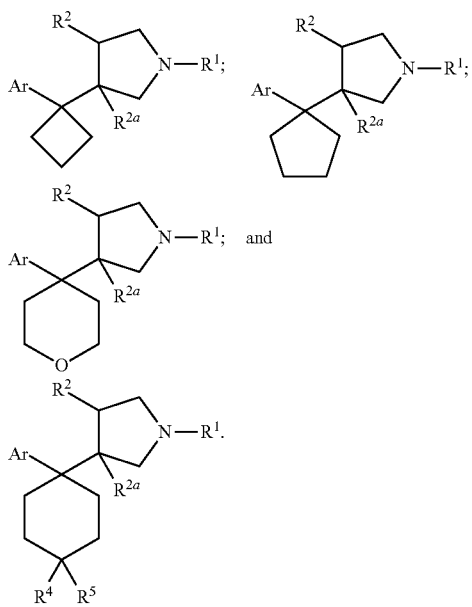

In various embodiments, Ar is a member selected from substituted or unsubstituted phenyl, and substituted or unsubstituted naphthyl. In an exemplary embodiment, Ar is a phenyl substituted with at least one halogen, or Ar is unsubstituted naphthyl. The phenyl group can be substituted with any halogen moiety; however, in one embodiment, it is substituted with at least one chloro moiety.

In an exemplary embodiment, Ar has a formula which is a member selected from:

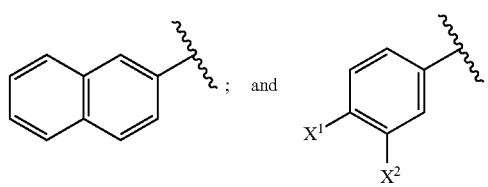

wherein $X^1$ and $X^2$ are independently selected from H and halogen. In exemplary compounds of the invention, at least one of $X^1$ and $X^2$ is halogen.

In certain embodiments, the invention provides compounds according to Formula I in which the moiety:

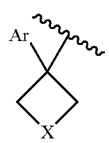

has a formula which is a member selected from:

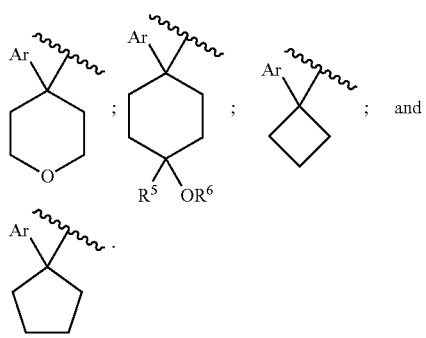

In various exemplary embodiments, the invention provides compounds according to Formula I in which the moiety:

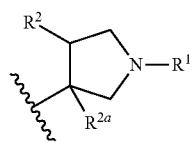

has a formula selected from:

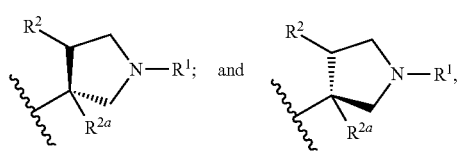

and Ar has a formula selected from:

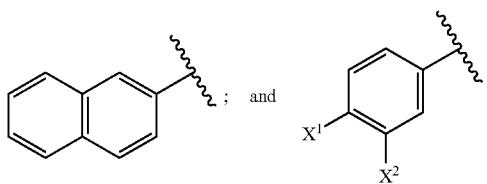

In an exemplary embodiment, the invention provides compounds according to Formula I wherein the moiety:

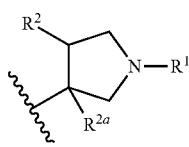

has the formula:

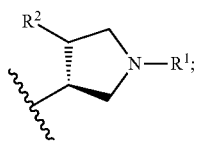

and
Ar has a formula selected from:

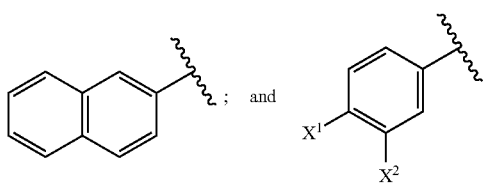

Exemplary compounds of the invention include an amine moiety (e.g., a primary, secondary or tertiary amino group) and as such can be converted into a salt form by contacting the compound (e.g., the free base) with an acid. In an exemplary embodiment, the salt form is generated to convert an otherwise oily or viscous compound into a solid substance for easier handling. In another exemplary embodiment, converting the free base of a compound of the invention into a corresponding salt increases solubility of the compound in aqueous media, which can effect biological characteristics, such as bioavailability, pharmacokinetics and pharmacodynamics. Hence, any salt forms, such as pharmaceutically acceptable salts, including salts of inorganic acids (e.g., hydrochloride salts) or organic acids, of the compounds of the invention are within the scope of the current invention. Also within the scope of the invention are any prodrugs of the compounds of the invention. For example, $R^3$ and $R^4$ can be any group, which is cleavable in vivo to result in an amine, such as a primary or secondary amine.

B. Compositions Including Stereoisomers

The compounds of the invention can include one or more stereocenter and may exist in particular geometric or stereoisomeric forms. Compounds can be chiral, racemic or be present in a composition including one or more stereoisomer. The current invention encompasses any enantiomer, diastereomer, racemic mixtures, enantiomerically enriched mixtures, and diastereomerically enriched mixture as well as any enantiomerically or diastereomerically (essentially) pure forms of the compounds of the invention. The invention contemplates cis- and trans-isomers, (−)- and (+)-enantiomers, (D)-isomers, (L)-isomers, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts may be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

Hence, in one embodiment, the invention provides a composition including a first stereoisomer and at least one additional stereoisomer of a compound of the invention. The first stereoisomer may be present in a diastereomeric or enantiomeric excess of at least about 80%, preferably at least about 90% and more preferably at least about 95%. In a particularly preferred embodiment, the first stereoisomer is present in a diastereomeric or enantiomeric excess of at least about 96%, at least about 97%, at least about 98%, at least about 99% or at least about 99.5%. Enantiomeric or diastereomeric excess may be determined relative to exactly one other stereoisomer, or may be determined relative to the sum of at least two other stereoisomers. In an exemplary embodiment, enantiomeric or diastereomeric excess is determined relative to all other detectable stereoisomers, which are present in the mixture. Stereoisomers are detectable if a concentration of such stereoisomer in the analyzed mixture can be determined using common analytical methods, such as chiral HPLC.

C. Synthesis of the Compounds

1. General

Compounds of the invention may be synthesized as a racemic mixture, a mixture of cis and trans isomers, or a mixture of two or more diastereomers. Stereoisomers may be separated at an appropriate synthetic stage, for example, by chiral column chromatography, such as HPLC to give enantiomerically/diastereomerically enriched or enantiomerically or diastereomerically pure forms of the respective stereoisomers. Cis and trans assignments may be made on the basis of NMR coupling patterns optionally in conjunction with literature values. Absolute configurations can be determined by synthesis from chiral precursor of known configuration, or by X-ray crystallographic determination using crystallized materials.

Cis- and trans-configurations are defined according to the relative configuration of the amine-bearing side chain and the substituent on the cyclalkyl ring. When more than one substituent is present, the higher order (IUPAC) substituent is used for the determination of cis- and trans-configuration.

Compounds of the invention may be synthesized according to the various schemes included herein. It is within the abilities of a person skilled in the art to select appropriate alternative reagents replacing the exemplary reagents shown in the schemes in order to synthesize a desired compound of the invention. It is also within the abilities of a skilled artisan to omit or add synthetic steps when necessary. As a non-limiting example, Ar in the schemes set forth herein is selected from substituted or unsubstituted naphthyl and substituted or unsubstituted phenyl. In an exemplary embodiment, Ar is 3,4-dichlorophenyl.

2. General Synthesis of Pyrrolidinyl Cycloalkylamines

In one embodiment, the compounds of the invention are synthesized from the corresponding nitrile a as shown in Scheme 1, below.

In the first step, nitrite a is alkylated with a dibromo-alkyl or heteroalkyl reagent, forming the corresponding cycloalkyl nitrile b, which is reduced to aldhehyde c. The aldehyde Wittig substrate c is converted to ester d and, subsequently to carboxylic acid-nitrile e. The nitrile and carboxylic acid groups are reduced to the corresponding amine and alcohol moieties, respectively (f) and pyrrolidine g is formed by cyclizing this substrate. The pyrrolidine amine is protected as the N-Boc or N-Troc moiety, forming compound h, which is separated into its enantiomers, i and j, by chiral chromatography. The enantiomers are deprotected, forming k and l, which are optionally N-alkylated, providing n and m, respectively.

Stereoisomeric mixtures of compounds of the invention are resolved, purified or enriched in one stereoisomer using art- Scheme 1:

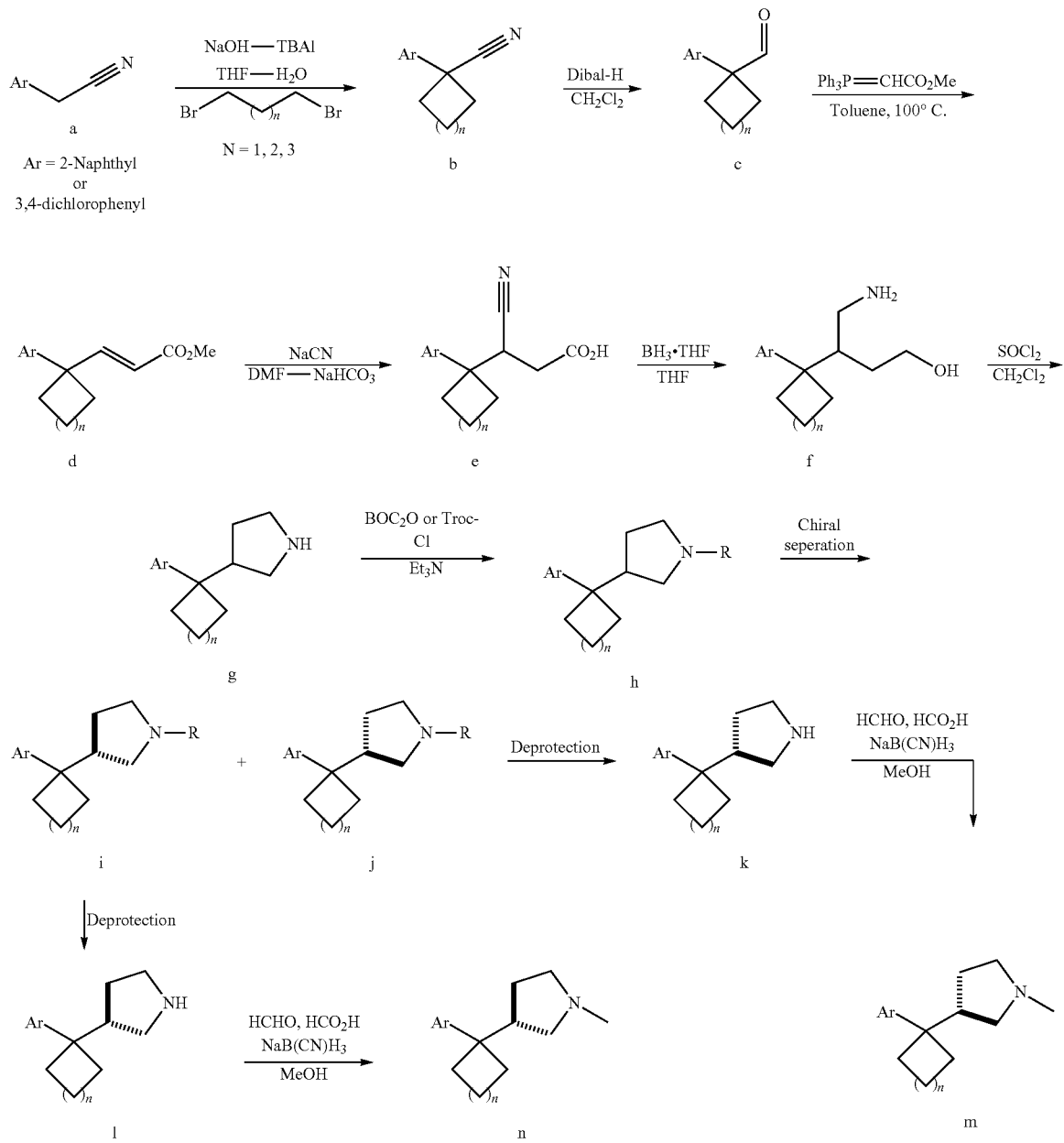

recognized methods including, but not limited to, chiral chromatography. An exemplary enrichment procedure using an RO1 column is set forth in Scheme 2:
Scheme 2
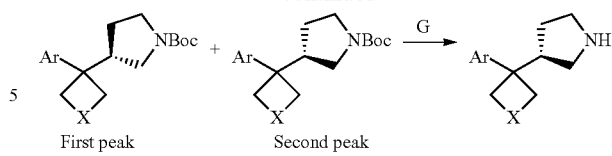
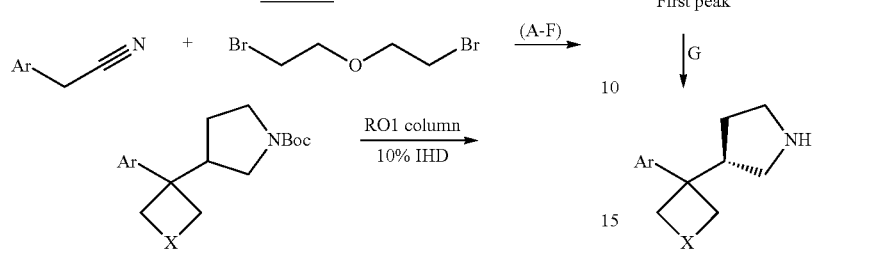
Scheme 3
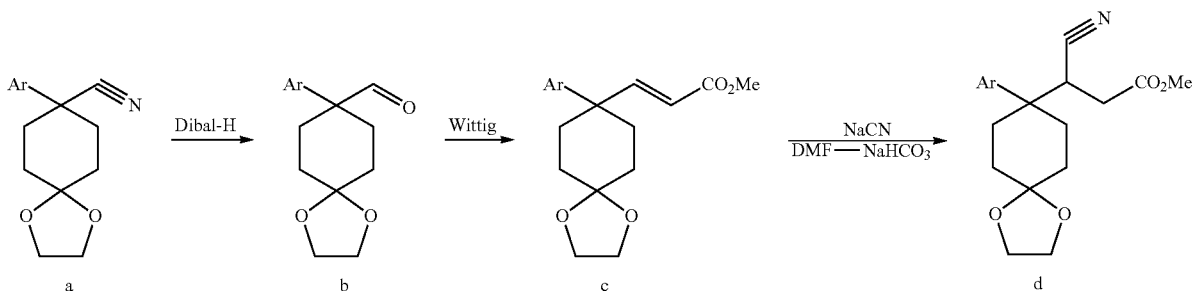
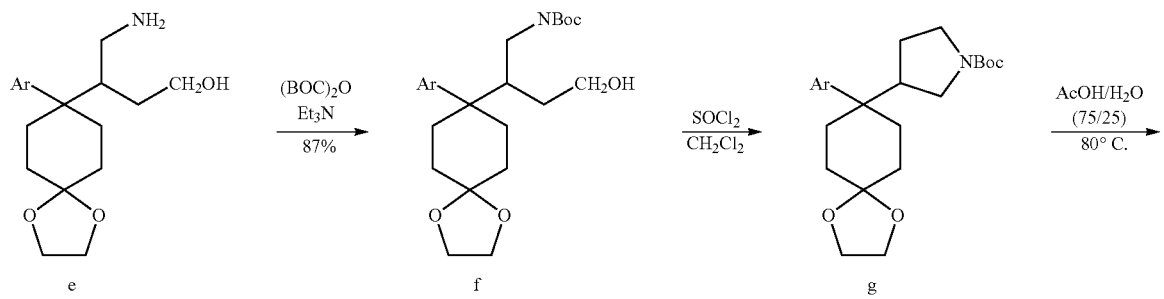
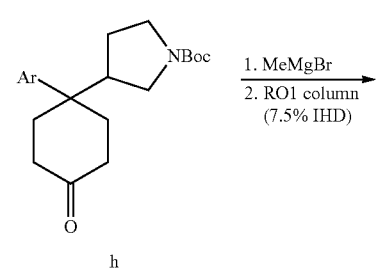

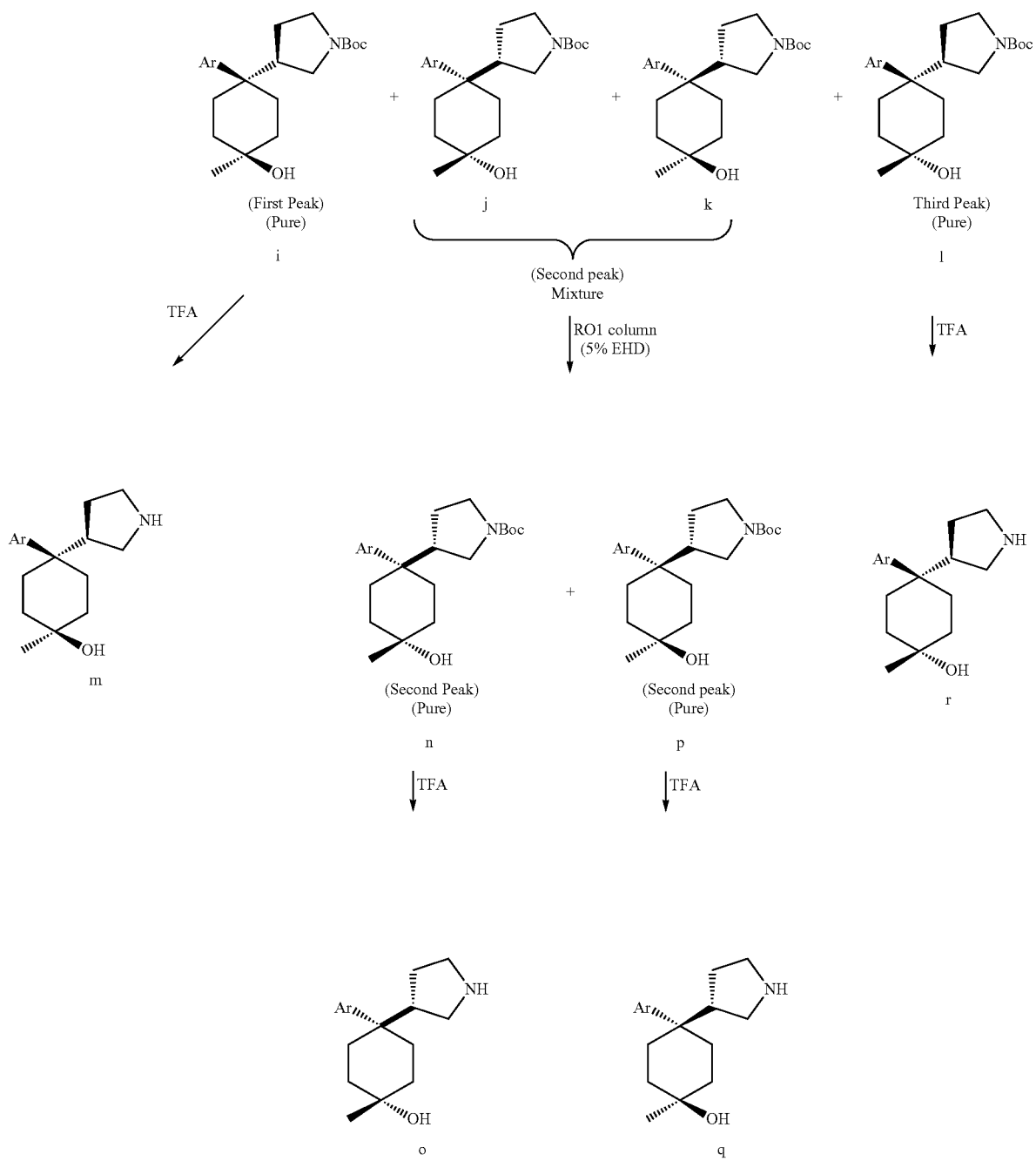

Scheme 3 provides an exemplary route for the synthesis and purification of substituted cyclohexyl compounds of the invention. Thus, protected cyano cyclohexyl ketone a is reduced to the corresponding aldehyde b by action of Dibal, forming the Wittig substrate, which is subsequently converted to unsaturated ester c. The double bond of c is converted to the corresponding nitrite d, and the nitrile and ester moieties are reduced to the corresponding amine and alcohol moieties, respectively, forming e. The amine moiety of e is protected as the Boc group and resulting compound f is cyclized to form pyrrolidinyl compound g. The masked ketone of compound g is deprotected, forming h, which is converted to substituted cyclohexyl derivative i by the action of methyl magnesium bromide. The resulting mixture of stereoisomers is resolved using a RO1 column. The first peak, contains pure 1, which is deprotected by removing the Boc moiety. The second peak includes two compounds, j and k, which are further resolved by resubmission to an RO1 column, affording n and p, which are subsequently deprotected by removing the Boc group, producing o and q, respectively. The third peak from the first chromatography provides pure 1, which is deprotected to form r.

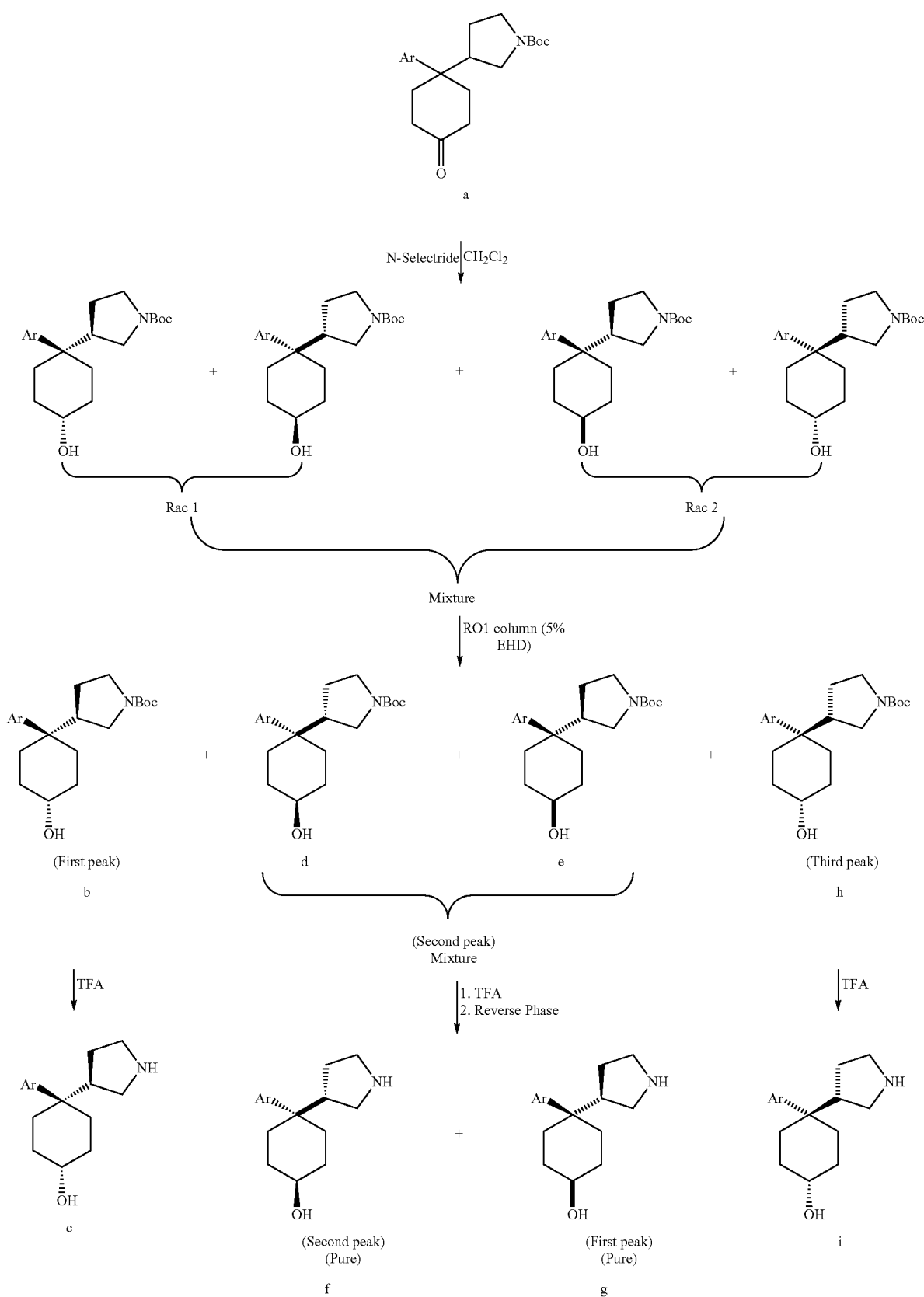
Scheme 4

In Scheme 4, an exemplary route for resolution of various stereoisomers of the invention is shown. Protected pyrrolidine ketone a is reduced to two racemic mixtures of the corresponding cyclohexyl alcohol, which are resolved using an RO1 column to a first peak containing pure b, a second peak containing a mixture of d and e and a third peak containing pure h. The N-Boc moiety of the compounds in the first and third peak, b and h, respectively are cleaved providing c and i. The compounds in the second peak are deprotected and submitted to reverse phase chromatography, affording pure f and g.

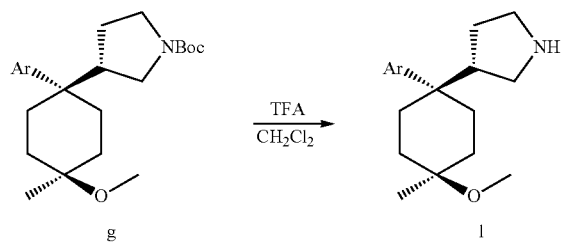

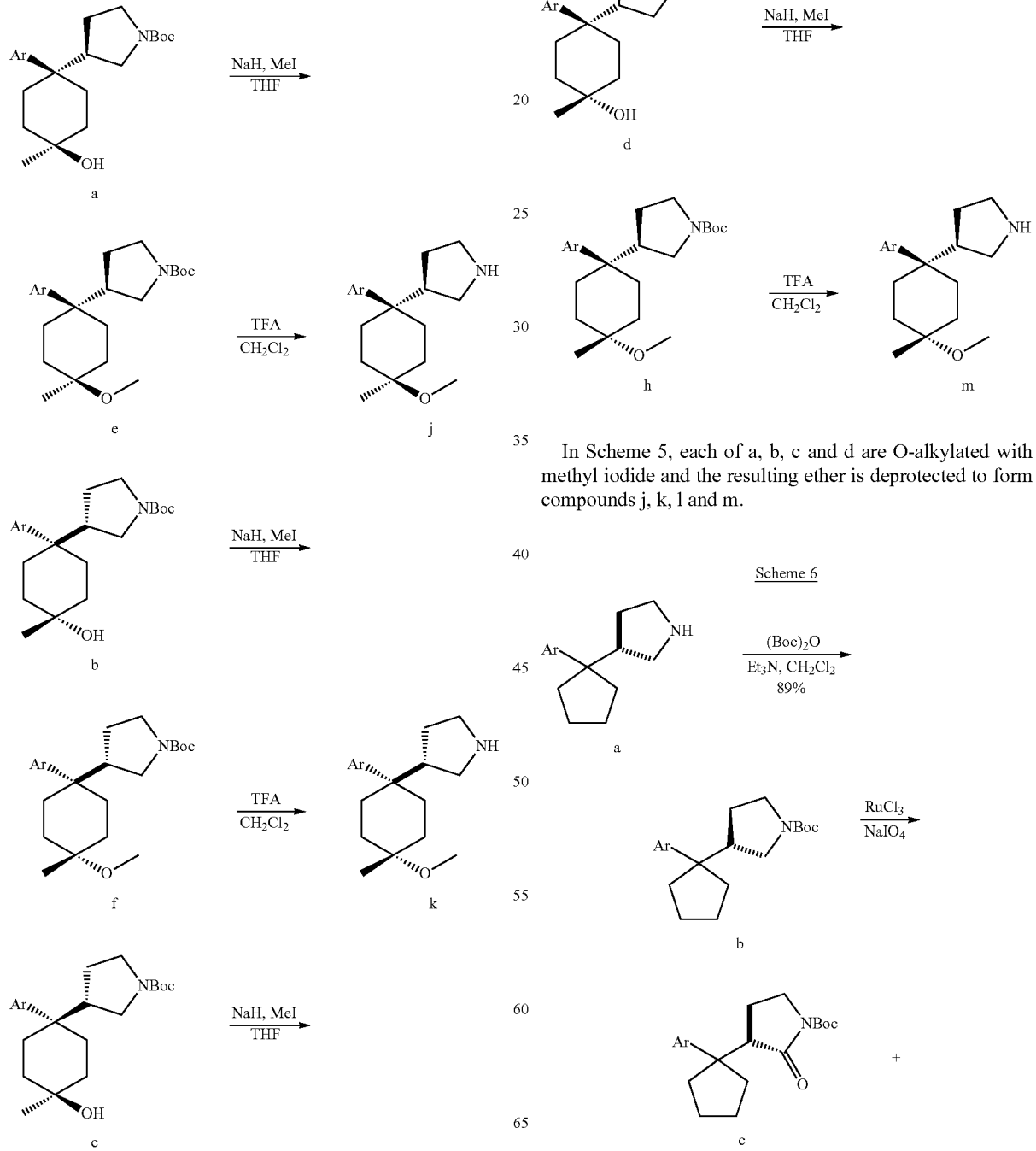

In Scheme 5, each of a, b, c and d are O-alkylated with methyl iodide and the resulting ether is deprotected to form compounds j, k, l and m.

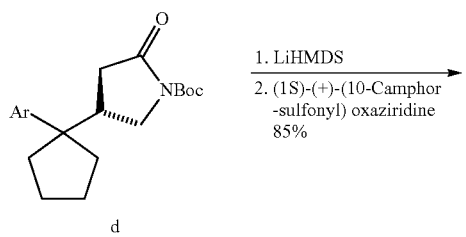
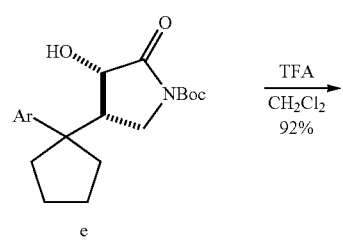
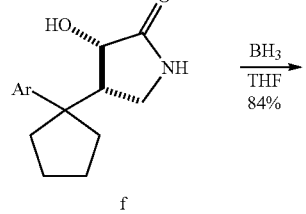
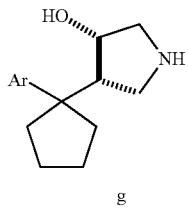
In Scheme 6, N—H pyrrolidone a is protected as the N-Boc derivative (b) and this compound is oxidized to the corresponding N-protected lactams c and d. The lactam is hydroxylated at a position alpha to the lactam carbonyl moiety, forming e, which is deprotected by removal of Boc to provide f, which is reductively decarbonylated by the action of BH$_3$, providing g.
Scheme 7
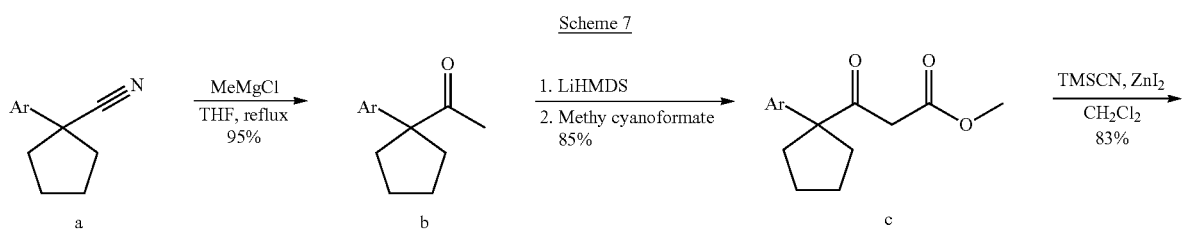
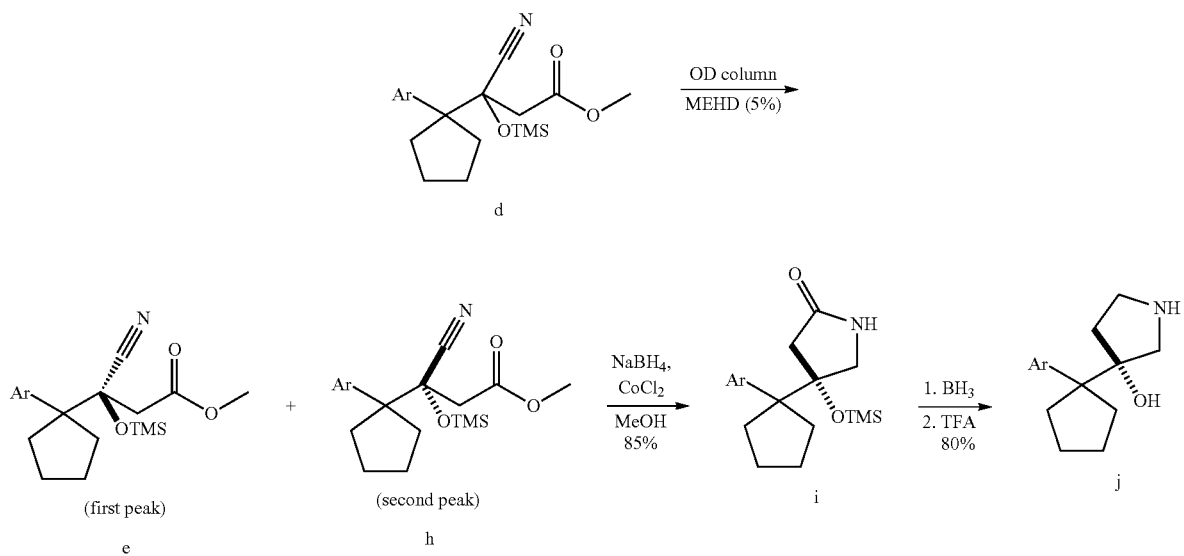

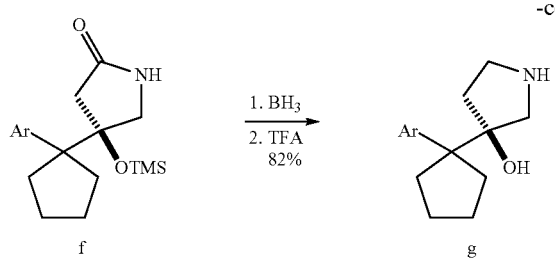

In Scheme 7, cyclopentyl nitrile a is converted to the corresponding ketone b, which is homologated to the corresponding methylene methyl ester c. Compound d is formed by conversion of the ketone carbonyl of c into the corresponding nitrile. The stereochemical mixture of d is resolved into peaks containing e and h. The compounds from these peaks are reacted through two steps to form compounds g and h.

Table 1 sets forth exemplary compounds of the invention prepared according to the methods set forth herein.

TABLE 1

Exemplary Compounds

| Cpd No. | Structure |
|---|---|
| 1 | 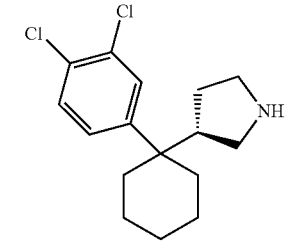 |
| 2 | 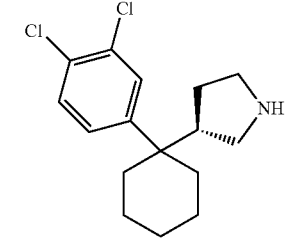 |
| 3 | 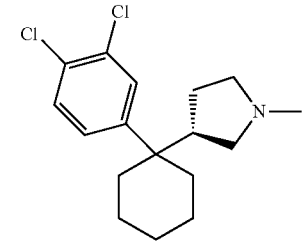 |

TABLE 1-continued

Exemplary Compounds

| Cpd No. | Structure |
|---|---|
| 4 | 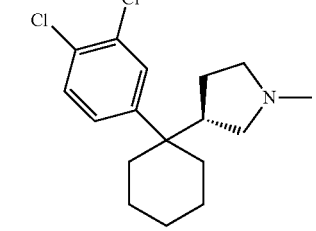 |
| 5 | 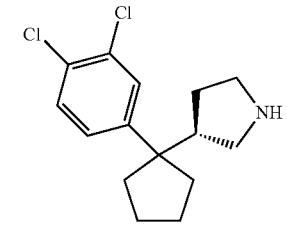 |
| 6 | 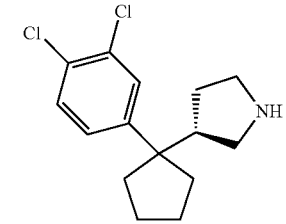 |
| 7 | 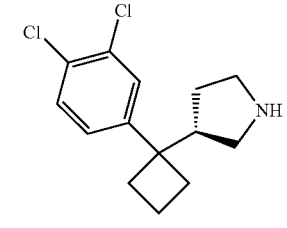 |
| 8 | 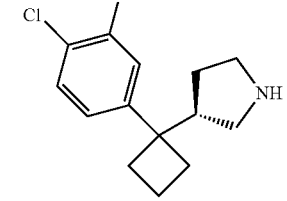 |

TABLE 1-continued

Exemplary Compounds

| Cpd No. | Structure |
|---|---|
| 9 | 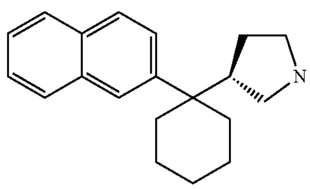 |
| 10 | 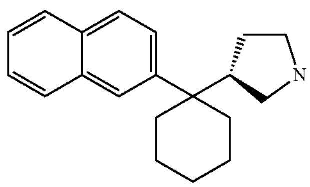 |
| 11 | 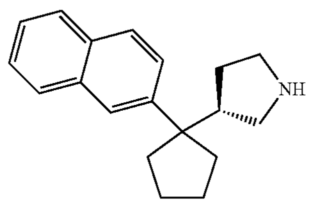 |
| 12 | 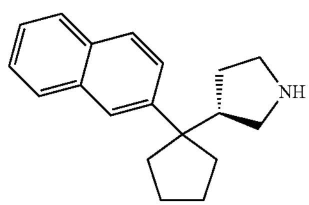 |
| 13 | 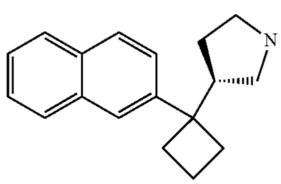 |
| 14 | 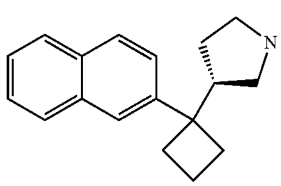 |
| 15 | 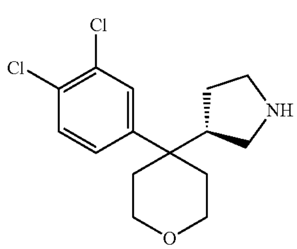 |
| 16 | 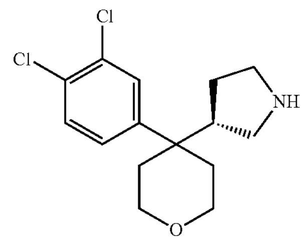 |
| 17 | 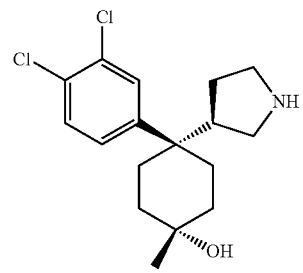 [SMILES: C[C@]1(O)CC[C@@](c2ccc(Cl)c(Cl)c2)([C@H]2CCNC2)CC1] |
| 18 | 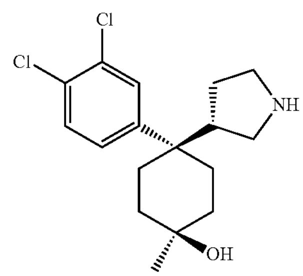 [SMILES: C[C@]1(O)CC[C@@](c2ccc(Cl)c(Cl)c2)([C@@H]2CCNC2)CC1] |
| 19 | 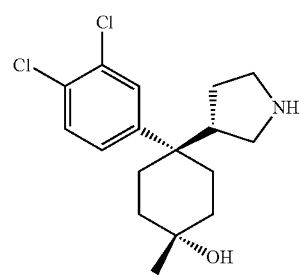 [SMILES: C[C@]1(O)CC[C@](c2ccc(Cl)c(Cl)c2)([C@@H]2CCNC2)CC1] |
| 20 | 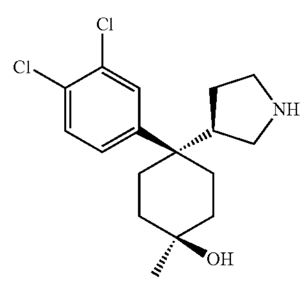 [SMILES: C[C@]1(O)CC[C@](c2ccc(Cl)c(Cl)c2)([C@H]2CCNC2)CC1] |

TABLE 1-continued
Exemplary Compounds
| Cpd No. | Structure |
|---|---|
| 21 | 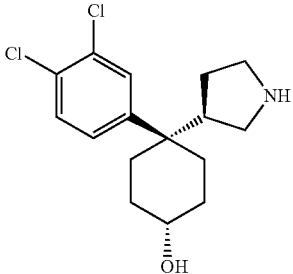 [SMILES: O[C@H]1CC[C@@](c2ccc(Cl)c(Cl)c2)([C@H]2CCNC2)CC1] |
| 22 | 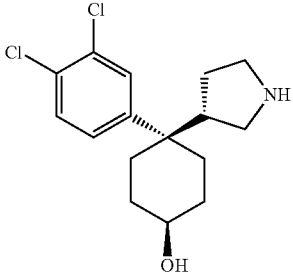 [SMILES: O[C@H]1CC[C@@](c2ccc(Cl)c(Cl)c2)([C@@H]2CCNC2)CC1] |
| 23 | 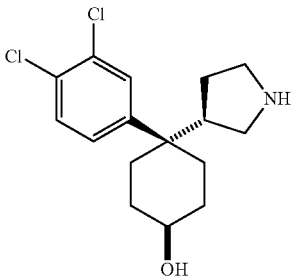 |
| 24 | 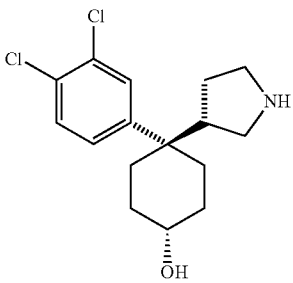 |
| 25 | 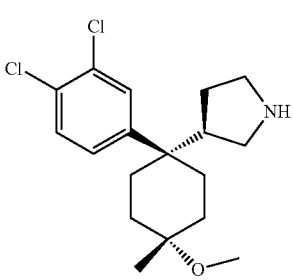 [SMILES: CO[C@]1(C)CC[C@](c2ccc(Cl)c(Cl)c2)([C@H]2CCNC2)CC1] |
| 26 | 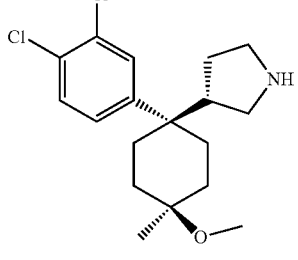 |
| 27 | 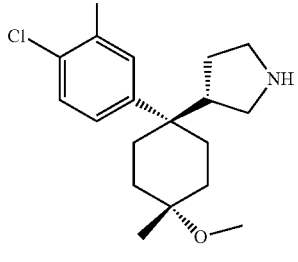 |
| 28 | 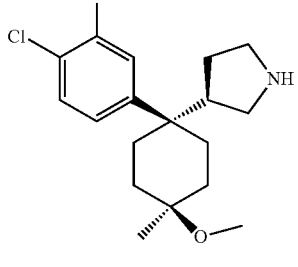 |
| 29 | 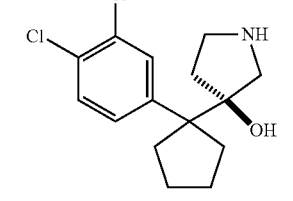 |
| 30 | 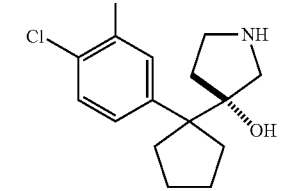 |
| 31 | 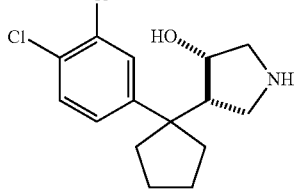 |
D. Pharmaceutical Compositions
The present invention also provides a pharmaceutical composition including a compound of the invention (e.g., a compound of Formula (I)) or a pharmaceutically acceptable salt or solvate thereof, and at least one pharmaceutically acceptable carrier.

As described in detail below, the pharmaceutical compositions of the present invention may be specially formulated for administration in solid or liquid form, including those adapted for oral administration, e.g., tablets, drenches (aqueous or non-aqueous solutions or suspensions), parenteral administration (including intravenous and intramuscular), or epidural injection as, for example, a sterile solution or suspension, or sustained release formulation. The pharmaceutical compositions of the present invention may also be specifically formulated for administration transdermally.

The pharmaceutical compositions of the invention may be administered orally, parenterally, subcutaneously, transdermally, nasally, or by anal suppository. The pharmaceutical compositions of the invention may also be administered using controlled delivery devices.

Formulations of the present invention include those suitable for oral and parenteral administration, particularly intramuscular, intravenous and subcutaneous administration. The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the compound which produces a therapeutic effect, without being toxic to the patient. Generally, out of one hundred percent, this amount will range from about 1 percent to about ninety-nine percent of active ingredient.

In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, caplets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a compound of the present invention as an active ingredient. A compound of the present invention may also be administered as a bolus, electuary or paste.

In solid dosage forms of the invention for oral administration (capsules, tablets, caplets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue. Pharmaceutical compositions or unit dosage forms of the present invention in the form of prolonged-action tablets may comprise compressed tablets formulated to release the drug substance in a manner to provide medication over a period of time. There are a number of tablet types that include delayed-action tablets in which the release of the drug substance is prevented for an interval of time after administration or until certain physiological conditions exist. Repeat action tablets may be formed that periodically release a complete dose of the drug substance to the gastrointestinal fluids. Also, extended release tablets that continuously release increments of the contained drug substance to the gastrointestinal fluids may be formed.

Compounds of the invention can be also administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the compounds of this invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Compounds of the present invention may also be formulated as transdermal, topical, and mucosal dosage forms, which forms include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences,* 16th and 18th eds., Mack Publishing, Easton Pa. (1980 & 1990); and *Introduction to Pharmaceutical Dosage Forms,* 4th ed., Lea & Febiger, Philadelphia (1985). Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied.

Depending on the specific tissue to be treated, additional components may be used prior to, in conjunction with, or subsequent to treatment with active ingredients of the invention. For example, penetration enhancers can be used to assist in delivering the active ingredients to the tissue.

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

When the compounds of the present invention are administered as pharmaceuticals, to humans and animals, they can be given per se or as a pharmaceutical composition containing, for example, 0.1 to 99.5% of active ingredient in combination with a pharmaceutically acceptable carrier.

The preparations of the present invention may be given orally and parenterally. They are of course given in forms suitable for each administration route. For example, they are administered in tablets or capsule form, by injection, and by intravenous administration. In one embodiment, oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

The present invention also provides a unit dosage form of a compound of the invention. In general, the unit dosage form includes the compound and a pharmaceutically acceptable carrier, diluent, excipient, etc. such as those set forth herein or otherwise known in the art. In an exemplary embodiment, the unit dosage formulation includes from about 0.1 to about 7000 mg of a compound of the invention. In various embodiments, the unit dosage formulation includes from 2.5 mg to about 500 mg, or from about 5 mg to about 50 mg of a compound of the invention. In various embodiments, the unit dosage includes a dose sufficient to provide antidepressant activity in the subject to whom the unit dosage formulation is administered. In various embodiments, the unit dosage provides sufficient active compound to provide anti-depressant activity in the subject to whom it is administered when the unit dosage is orally administered.

IV. Methods

A. General

The present invention also provides methods of using the compounds of the invention, which are set forth in greater detail hereinbelow. The terms "treatment" or "treating" is intended to encompass therapy, preventing (prophylaxis), preventing relapse, and amelioration of acute symptoms. Note that "treating" refers to either or both of the amelioration of symptoms and the resolution of the underlying condition. In many of the conditions of the invention, the administration of a compound or composition of the invention may act not directly on the disease state, but rather on some pernicious symptom, and the improvement of that symptom leads to a general and desirable amelioration of the disease state The patient receiving this treatment is any animal in need, including primates, in particular humans, and other mammals such as equines, cattle, swine and sheep, as well as poultry and pets in general.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient will range from about 0.005 mg per kilogram to about 5 mg per kilogram of body weight per day.

The compounds and pharmaceutical compositions of the invention can be administered in conjunction with other pharmaceutical agents, for instance antimicrobial agents, such as penicillins, cephalosporins, aminoglycosides and glycopeptides, and other psychoactive agents. Conjunctive therapy thus includes sequential, simultaneous and separate administration of the active compound in a way that the therapeutic effects of the first administered agent have not entirely disappeared when the subsequent agent is administered.

B. Binding to Monoamine Transporter

In another aspect the invention provides a method of binding a compound of the invention to a monoamine transporter. The method includes contacting the monoamine transporter and a compound of the invention.

In yet another aspect, the invention provides a method of inhibiting binding of a monoamine transporter ligand to a monoamine transporter (such as serotonin transporter, dopamine transporter and norepinephrine transporter). The method includes contacting the monoamine transporter and a compound of the invention. In an exemplary embodiment the monoamine transporter ligand is an endogenous monoamine, such as serotonin, dopamine or norepinephrine. In another exemplary embodiment, the ligand is a drug molecule or another small molecule known to have binding affinity to a monoamine transporter. In another exemplary embodiment, the monoamine transporter ligand is a radioactively labeled compound, known to bind to the monoamine transporter.

In an exemplary embodiment, inhibition of ligand binding is shown using an ex vivo binding assay, such as those described herein, below in Example 7. In an exemplary embodiment, the compound of the invention inhibits mean binding by between about 1% and about 100%, preferably by between about 10% and about 100%, more preferably by between about 20% and about 90% when compared to vehicle Inhibition of mean binding is preferably dose dependent.

C. Inhibition of Monoamine Transporter Activity

In yet another aspect, the invention provides a method of modulating (e.g, inhibiting, augmenting) the activity of at least one monoamine transporter, such as serotonin transporter, dopamine transporter and norepinephrine transporter. The method includes contacting the monoamine transporter and a compound of the invention. In an exemplary embodiment, the monoamine transporter is contacted with a compound of the invention by administering to a subject a therapeutically effective amount of the compound of the invention, e.g., a compound according to Formula (I), or a pharmaceutically acceptable salt or solvate thereof. In a preferred embodiment, the subject is a human. In another exemplary embodiment, the monoamine transporter is dopamine transporter (DAT), serotonin transporter (SERT) or norepinephrine transporter (NET). In another exemplary embodiment, the compound of the invention inhibits the activity of at least two different monoamine transporters Inhibition of monoamine transporter activity may be measured using assays known in the art. Exemplary assay formats include in vitro functional uptake assays. In an exemplary embodiment, the functional uptake assay utilizes an appropriate cell-line expressing a desired monoamine transporter. In another exemplary embodiment, the functional uptake assay utilizes synaptosomes isolated from brain tissue of an appropriate organism. Alternatively, inhibition of monoamine transporter activity may be assessed using receptor binding experiments known in the art, e.g., utilizing appropriate membrane preparations. Another assay involves treatment of a test subject (e.g., a rat) with a compound of the invention as well as a reference compound, followed by isolation of brain tissue and ex vivo analysis of receptor occupancy, as described herein.

D. Inhibition of Monoamine Uptake

In yet another aspect, the invention provides a method of inhibiting uptake of at least one monoamine (e.g., dopamine, serotonin, norepinephrine) by a cell. The method includes contacting the cell with a compound of the invention. In an exemplary embodiment, the cell is a brain cell, such as a neuron or a glial cell. In one example, inhibition of monoamine uptake occurs in vivo. In an organism, neuronal uptake (also termed reuptake) of a monoamine such as dopamine or serotonin occurs, for example, from the synaptic cleft. Thus, in one embodiment, the neuronal cell is in contact with a synaptic cleft of a mammal. In another exemplary embodiment, inhibition of monoamine uptake occurs in vitro. In those methods the cell, may be a brain cell, such as a neuronal cell or a cell-type, which expresses a recombinant monoamine transporter.

In one embodiment, the compound inhibits uptake of at least two different monoamines. This can, for example, be shown by performing various in vitro functional uptake assays utilizing a cell-type, which simultaneously expresses multiple different monoamine transporters (such as isolated synaptosomes), or may be shown by using two different cell types, each expressing a different monoamine transporter, such as a recombinant dopamine transporter, together with an appropriate, labelled monoamine. Inhibition of monoamine uptake is demonstrated when the inhibitor (e.g., a compound of the invention) has an $IC_{50}$ of between about 0.1 nM and about 10 µM, preferably between about 1 nM and about 1 µM, more preferably between about 1 nM and about 500 nM, and even more preferably between about 1 nM and about 100 nM in a functional monoamine uptake assay, such as those described herein below.

E. Treatment of CNS Disorders

In another aspect, the invention provides a method of treating depression by inhibiting the activity at least one monoamine transporter. The method includes administering to a mammalian subject a compound of the invention. In an exemplary embodiment, the mammalian subject is a human. In another exemplary embodiment, the compound of the invention inhibits the activity of at least two different monoamine transporters. For example, the compound of the invention inhibits the activity of at least two of serotonin transporter, dopamine transporter and norepinephrine transporter. Inhibition of monoamine transporter activity may be shown by functional monoamine uptake assays as described herein below. Demonstration of anti-depressant activity of a compound of the invention may be shown by utilizing an appropriate animal model of depression, such as the Rat Forced Swim Test, the Mouse Tail Suspension Test and Rat Locomotor Activity Analyses. The Rat Forced Swim Test is also suitable for the analysis of compounds having activities against more than one monoamine transporter (mixed monoamine transporter activity). For example, an increase in swimming activity is indicative of serotonin reuptake inhibition, while an increase in climbing activity is indicative of norepinephrine reuptake inhibition. In a preferred embodiment, the compounds of the invention are active in at least one animal model, which can be used to measure anti-depressant-like activities, for instance those assessing immobility. In an exemplary embodiment, the compounds of the invention are active when they inhibit mean immobility by between about 5% and about 90%, preferably between about 10% and about 70% and more preferably between about 10% and about 50% in at least one animal model, when compared to vehicle.

In yet another aspect, the invention provides a method of effecting an anti-depressant-like effect. The method includes administering to a mammalian subject in need thereof a therapeutically effective amount of a compound or composition of the invention, e.g., a compound according to Formula (I), or a pharmaceutically acceptable salt or solvate thereof. Anti-depressant-like effects may be measured using an animal model of disease, such as those described herein.

In a further aspect, the invention provides a method of treating a central nervous system disorder. The method includes administering to a subject in need thereof a therapeutically effective amount of a composition or compound of the invention, e.g., a compound according to Formula (I), or a pharmaceutically acceptable salt or solvate thereof. In a preferred embodiment, the subject is a human.

In another exemplary embodiment, the central nervous system disorder is a member selected from the group consisting of depression (e.g., major depressive disorder, bipolar disorder, unipolar disorder, dysthymia and seasonal affective disorder), cognitive deficits, fibromyalgia, pain (e.g., neuropathic pain), sleep related disorders (e.g., sleep apnea, insomnia, narcolepsy, cataplexy) including those sleep disorders, which are produced by psychiatric conditions, chronic fatigue syndrom, attention deficit disorder (ADD), attention deficit hyperactivity disorder (ADHD), restless leg syndrome, schizophrenia, anxieties (e.g. general anxiety disorder, social anxiety disorder, panic disorder), obsessive compulsive disorder, posttraumatic stress disorder, seasonal affective disorder (SAD), premenstrual dysphoria, postmenopausal vasomotor symptoms (e.g., hot flashes, night sweats), and neurodegenerative disease (e.g., Parkinson's disease, Alzheimer's disease and amyotrophic lateral sclerosis), manic conditions, dysthymic disorder, and cyclothymic disorder. In a preferred embodiment, the CNS disorder is depression, such as major depressive disorder. In an exemplary embodiment, the compounds of the invention are useful to treat two conditions/disorders, which are comorbid, such as cognitive deficit and depression.

Central nervous system disorder includes cerebral function disorders, including without limitation, senile dementia, Alzheimer's type dementia, cognition, memory loss, amnesia/amnestic syndrome, epilepsy, disturbances of consciousness, coma, lowering of attention, speech disorders, Lennox syndrome, autism, and hyperkinetic syndrome.

Neuropathic pain includes without limitation post herpetic (or post-shingles) neuralgia, reflex sympathetic dystrophy/causalgia or nerve trauma, phantom limb pain, carpal tunnel syndrome, and peripheral neuropathy (such as diabetic neuropathy or neuropathy arising from chronic alcohol use).

Other exemplary diseases and conditions that may be treated using the methods of the invention include obesity; migraine or migraine headache; urinary incontinence, including without limitation involuntary voiding of urine, dribbling or leakage of urine, stress urinary incontinence (SUI), urge incontinence, urinary exertional incontinence, reflex incontinence, passive incontinence, and overflow incontinence; as well as sexual dysfunction, in men or women, including without limitation sexual dysfunction caused by psychological and/or physiological factors, erectile dysfunction, premature ejaculation, vaginal dryness, lack of sexual excitement, inability to obtain orgasm, and psycho-sexual dysfunction, including without limitation, inhibited sexual desire, inhibited sexual excitement, inhibited female orgasm, inhibited male orgasm, functional dysparcunia, functional vaginismus, and atypical psychosexual dysfunction.

Selected compounds of the invention were evaluated in the mouse tail suspension and locomotor activity test, which showed that the tested compounds exhibited an antidepressant-like profile (i.e., significantly decreased immobility time). At doses active in the tail suspension test, no change or a decrease in baseline motor activity was observed indicating that antidepressant-like activity was not due to a general stimulant effect.

Selected compounds of the invention were also evaluated in the rat forced swim and locomotor activity tests. The decrease in immobility produced by these compounds appeared to be due to increases in swimming and climbing behaviors indicative of mixed transporter activity (i.e., SNRI profiles). In conclusion, the tested compounds of the invention exhibited an anti-depressant profile in at least three animal models, the mouse tail suspension test and rat locomotor activity test as well as the rat forced swim test.

The following examples are provided to illustrate selected embodiments of the invention and are not to be construed as limiting its scope.

EXAMPLES

1. General Procedures

In the examples, below, the following general experimental procedures were used unless otherwise noted: All commercial reagents were used without further purification. Anhydrous reactions were performed in flame-dried glassware under $N_2$. NMR spectra were recorded on a Varian 400 MHz spectrometer in deuterochloroform or methanol-$d^4$ with trimethylsilane (TMS) as an internal reference. Silica gel column chromatography was performed using an ISCO Combiflash system with detection at 254 nm or using ISCO normal phase silica gel cartridges.

Analytical HPLC

Analytical HPLC was performed on a Hewlett Packard Series 1100 pump connected to an Agilent Zorbax RX-C18 5 μm, 4.6×250 mm column, with detection on a Hewlett Packard Series 1100 UV/Vis detector monitoring at 214 and 254 nm. Typical flow rate=1 ml/min. Three different HPLC columns and various elution protocols were used. For example, (1) Agilent Zorbax RX-C18 5 μm, 4.6×250 mm column running a linear gradient. Solvent A=$H_2O$ w/0.05% TFA, Solvent B=MeCN w/0.05% TFA. Time 0 min=5% Solvent B, time 4 min=40% Solvent B, time 8 min=100% Solvent B, 12 min=5% Solvent B, 20 min=5% Solvent B; (2) Phenomenex 3μ C18 column running a 3 minute gradient of 5→100% B (acetonitrile/0.1% formic acid) and solvent A (water/0.1% formic acid); (3) Phenomenex 5μ C18 column running a 5 minute gradient of 5→100% B where solvent B (acetonitrile/0.1% formic acid) and solvent A (water/0.1% formic acid).

Reverse Phase HPLC Purification

Reverse phase HPLC purification was performed on a Gilson system using a Phenomenex 5μ C18 (50×21.2 mm) column. The standard separation method was: 10 minute gradient of 10→100% B (acetonitrile/0.1% formic acid) in solvent A (water/0.1% formic acid). Crude samples were typically dissolved in MeOH. Fractions were concentrated by Genovac (centrifugation at low pressure).

GC-MS

Gas chromatography was performed on a Hewlett Packard 6890 Series GC System with an HP1 column (30 meters, 0.15μ film thickness) coupled to a Hewlett Packard 5973 Series Mass Selective Detector. The following linear temperature gradient was used: 100° C. for 5 minutes, then 20° C./min to 320° C. Hold @ 320° C. for 10 minutes.

LCMS

LCMS was performed on an Agilent 1100 Series system connected to a Micromass Platform LC. The following column and gradient was used: Column: Luna C18(2), 3 um particle size 30×2.0 mm column dimension. Flow rate=0.5 mL/min, Solvent A=0.1 M $NH_4Ac$ in 95% $H_2O$, 5% MeOH, pH 6.0, Solvent B=Solvent B: 0.1 M $NH_4Ac$ in MeOH. Linear gradient with 6 entries: Time 0 min=100% Solvent A, time 10 min=100% Solvent B, time 12 min=100% Solvent B, time 12 min 10 sec=100% Solvent A, time 14 min=100% Solvent A, time 14 min 20 sec=100% Solvent A.

Microwave (μW) Recrystallization

The crude salt (e.g., HCl salt) was loaded into a microwave vessel with a stir bar. The recrystallization solvent was added and the vessel was heated at the target temperature for a given time. The vessel was cooled to 50° C. in the reactor, was then removed and allowed to slowly cool to RT. N,N-dimethyl amines were typically recrystallized in EtOAc or EtOAc:$CH_3CN$ (2:1). N-Me or primary amines were typically recrystallized in $CH_3CN$. mixture was stirred at 25° C. for 18 h. The mixture was cooled to 15° C. and quenched with sat. aq. $NH_4Cl$ (100 mL). The resulting mixture was partitioned between $H_2O$ (1.2 L) and t-butyl methyl ether (MTBE) (300 mL). The aqueous layer was further extracted with MTBE (200 mL). The combined organic layers were washed with brine (200 mL), dried over $MgSO_4$ (5 g) and spin-evaporated in vacuo to an oil. The oil was chromatographed on a silica gel column (1.0 kg) packed in, and eluted with hexanes-EtOAc (4:1) (8.0 L). Appropriate fractions as determined by TLC were combined and spin-evaporated in vacuo to an oil, which solidified when pumped down, giving 27.4 g (97.0%) of purified product. A total of 240.2 g of product suitable for further transformation was prepared in this fashion.

Example 1

Generic Procedure: Synthesis of Cycloalkyl Pyrrolidine

A: Cyclization

To a solution of 1 (50 mmoL) in THF (200 mL)-NaOH (50%, 100 mL) at 0° C. was added TBAI (tetra-butylammonium iodide, 2.0 g) and dibromoalkane (60 mmoL). The reaction mixture was stirred for 12 h before being concentrated. The product was extracted with diethyl ether (200 mL×3). The combined extracts were dried and concentrated. The residue was purified by silica gel column chromatogra-

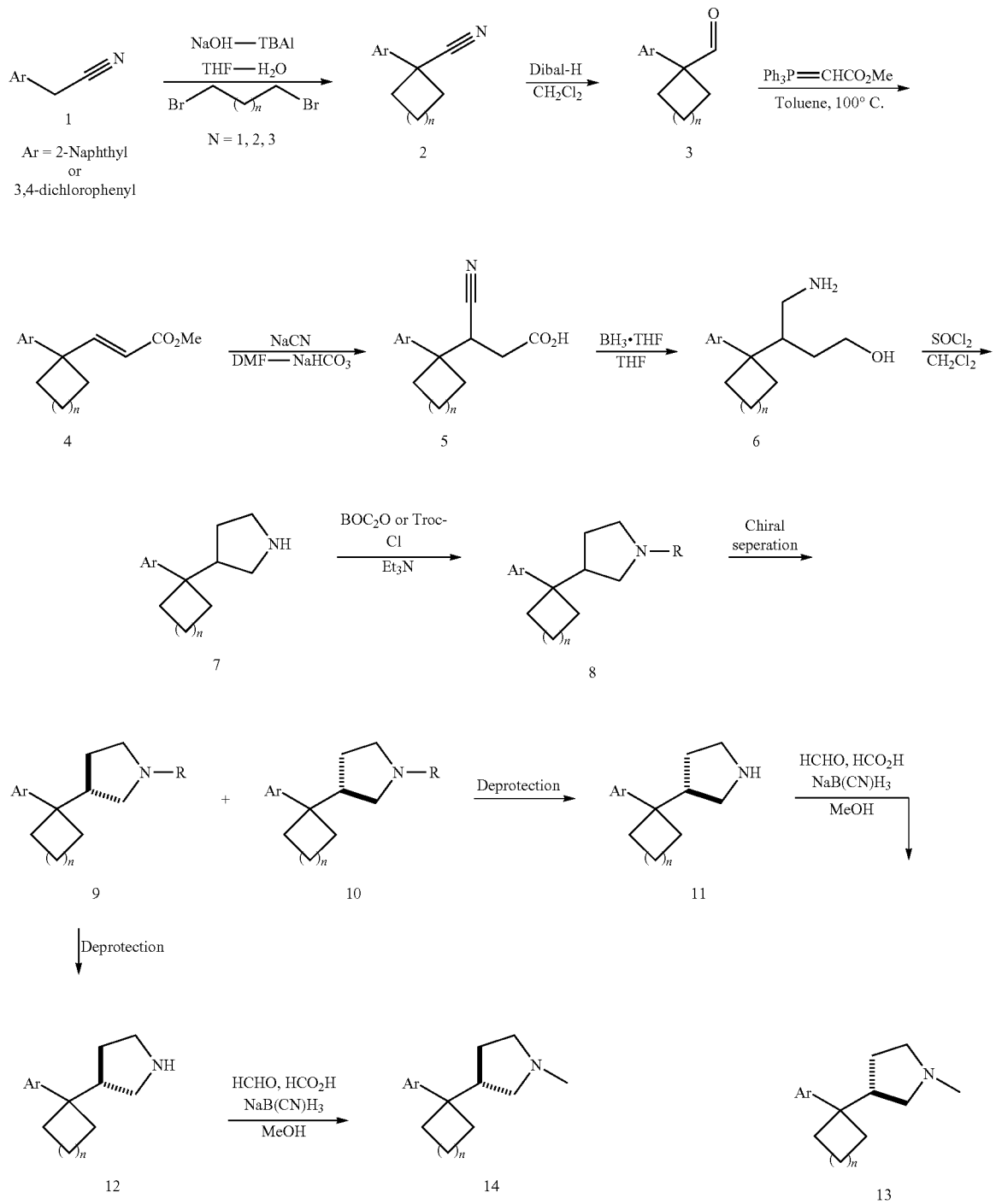

Scheme 1:

phy (hexane/ethyl acetate, gradient: 0/100 to 50/50) to give the desired product (~85-95%).

B: Reduction and Wittig Reaction:

To a solution of 2 (40 mmoL) in $CH_2Cl_2$ (250 mL) at −78° C. was added Dibal-H (1.0 M in hexane, 48 mL, 48 mmoL). The reaction mixture was stirred for 20 min before being quenched by McOH (40 mL) and HCl (6 N, 200 mL). The product was extracted with diethyl ether (200 mL×2). The combined extracts were dried and concentrated. The residue was used in the next step without further purification.

To a solution of the residue from the above reaction in toluene (250 mL) was added the Wittig reagent (60 mmoL). The reaction mixture was stirred at 100° C. for 7 h before being concentrated. The resultant residue was purified by silica gel column chromatography (hexane/ethyl acetate, gradient: 0/100 to 60/40) to give the desired product 4 (~90% for two steps).

C: Sodium Cyanide addition:

To a solution of 4 (30 mmoL) in DMF (150 mL) and $NaHCO_3$ (saturated, 10 mL) at room temperature was added NaCN (120 mmoL). The reaction mixture was stirred for 16 h before being concentrated. The resultant residue was acidified with HCl (4 N, 150 mL). The product was extracted with $CH_2Cl_2$ (200 mL×3). The combined extracts were dried and concentrated. The resultant residue was used in the next step without further purification.

D: Borane Reduction

To a solution of the residue from the above reaction in THF (150 mL) was added $BH_3$.THF (1.0 M in THF, 200 mL, 200 mmoL) at room temperature. The reaction mixture was stirred 14 h before being concentrated. The resultant residue was quenched by MeOH (100 mL). The resultant mixture was concentrated and purified by silica gel column chromatography (ethyl acetate/MeOH/$NH_3$, gradient: 100/0/2 to 70/30/5) to give the desired product 6 (~79% for two steps).

F: Cyclization of Amino Alcohol:

To a solution of 6 (10 mmoL) in $CH_2Cl_2$ (100 mL) was slowly added $SOCl_2$ (20 mmoL) at 0° C. The reaction mixture was stirred for 2 h before being concentrated. The residue was dissolved in $CH_2Cl_2$ (100 mL) and washed with NaOH solution (6 N, 10 mL). The organic layer was separated. The aqueous layer was extract with $CH_2Cl_2$ (100 mL×2). The combined extracts were dried and concentrated. The residue was used in the next step without further purification.

Generic Method F for Chiral Separation:

F: Protection of Amine with Boc Group and Purification (for Ar=Naphthyl, n=1, 2, 3; Ar=3,4-Dichlorophenyl, n=2, 3):

To a solution of 7 (8 mL) from the above reaction in $CH_2Cl_2$ (30 mL) was added $Et_3N$ (12 mmoL) and $(BOC)_2O$ (10 mmoL) The reaction mixture was stirred for 2 h at room temperature before being quenched by $NH_4Cl$ (saturated, 100 mL). The organic layer was separated. The aqueous layer was extract with $CH_2Cl_2$ (50 mL×2). The combined extracts were dried and concentrated. The residue was purified by silica gel column chromatography (Hexane/ethyl acetate, gradient: 100/0 to 50/50) to give the desired product 8 (~86%).

The two enantiomers of 8 were separated by chiral column; the conditions for these and other compounds of the invention are summarized in the following table. Scheme 2, shows a representative separation of two enantiomers and the subsequent deprotection of the purified enantiomers. Compound numbers in this table and throughout the examples are with reference to Table 1, supra.

| Compounds | Separation Conditions | | |
|---|---|---|---|
| | Chiral column | Eluent | Enantiomers |
| Ar = 3,4 dichlorophenyl n = 3 | RO1 | iPrOH/Heptane/ DEA = 10:90:0.1 | 1 (first peak) 2 (second peak) |
| Ar = 3,4 dichlorophenyl n = 2 | AD | Hexane/iPrOH/ DEA = 93/7/0.1 | 5 (first peak) 6 (second peak) |
| Ar = 2-naphthyl n = 3 | AD | Hexane/iPrOH/ DEA = 95/5/0.1 | 9 (first peak) 10 (second peak) |
| Ar = 2-naphthyl n = 2 | AD | Hexane/iPrOH/ DEA = 90/10/0.1 | 11 (first peak) 12 (second peak) |
| Ar = 2-naphthyl n = 1 | RO1 | Hexane/iPrOH/ DEA = 90/10/0.1 | 13 (first peak) 14 (second peak) |

G: Deprotection of Boc Group:

To a solution of the N-Boc enantiomer (4 mmoL) in $CH_2Cl_2$ (10 mL) was added TFA (3 mL). The reaction mixture was stirred for 20 min before being concentrated. The residue was purified by reverse phase column chromatography to give the pure enantiomers.

H: Protection of Amine with Troc Group and Purification (for Ar=3,4-Dichlorophenyl, n=1, R=Troc)

To a solution of 7 (8 mL) from the above reaction in $CH_2Cl_2$ (30 mL) was added $Et_3N$ (12 mmoL) and TrocCl (10 mmoL). The reaction mixture was stirred for 2 h at room temperature before being quenched by $NH_4Cl$ (saturated, 100 mL). The organic layer was separated. The aqueous layer was extract with $CH_2Cl_2$ (50 mL×2). The combined extracts were dried and concentrated. The residue was purified by silica gel column chromatography (Hexane/ethyl acetate, gradient: 100/0 to 50/50) to give the desired product 8 (~90%).

Crude 8 was separated by chiral column (eluent: Hexane/ iPrOH/DEA=93/7/0.1 to give the two enantiomers (First peak is N-Troc protected 8, second peak is N-Troc protected 7).

I: Deprotection of N-Troc Group:

To a solution of the N-Troc enantiomer (4 mmoL) in THF (10 mL) was added $NH_4Cl$ (saturated, 2 mL) and Zn dust (12 mmol). The reaction mixture was stirred for 2 h before the solid was filtered. The filtrate was concentrated. The residue was purified by reverse phase column chromatography to give the pure enantiomers.

J: Reductive Amination:

To a solution of the amine 11 or 12 (3 mmol) in MeOH (6 mL) was added HCHO (37% in water, 2 mL), $HCO_2H$ (0.5 mL) and $NaB(CN)H_3$ (6 mmol). The reaction was stirred for about 30 min before being concentrated. The resulting residue was purified by reverse phase column chromatography ($CH_3CN/H_2O$, gradient, 10% to 100% $CH_3CN$ in 10 min) to give pure 13 or 14 ((~80%).

TABLE 2

| Cpd. No. | Structure | Generic Methods | Data |
|---|---|---|---|
| 1 | 3,4-dichlorophenyl-cyclohexyl-pyrrolidine (NH) | A B C D E F G | ¹H NMR (400 MHz, CD₃OD) δ 7.53 (m, 2 H), 7.33 (d, J = 8.4 Hz, 1 H), 3.24 (m, 1 H), 3.16 (m, 2 H), 2.73 (t, J = 11.6 Hz, 1 H), 2.42-2.28 (m, 3 H), 1.93-1.88 (m, 1 H), 1.62-1.59 (m, 6 H), 1.32-1.21 (m, 3 H); ¹³C NMR (100 MHz, CD₃OD) δ 143.19, 132.45, 130.46, 130.33, 130.11, 128.25, 50.28, 45.46, 44.86, 44.58, 33.80, 33.64, 26.21, 24.96, 21.92; ESI MS + 1 m/z 299. |
| 2 | 3,4-dichlorophenyl-cyclohexyl-pyrrolidine (NH) | A B C D E F G | ¹H NMR (400 MHz, CD₃OD) δ 7.53 (m, 2 H), 7.33 (d, J = 8.4 Hz, 1 H), 3.24 (m, 1 H), 3.16 (m, 2 H), 2.73 (t, J = 11.6 Hz, 1 H), 2.42-2.28 (m, 3 H), 1.93-1.88 (m, 1 H), 1.62-1.59 (m, 6 H), 1.32-1.21 (m, 3 H); ¹³C NMR (100 MHz, CD₃OD) δ 143.19, 132.45, 130.46, 130.33, 130.11, 128.25, 50.28, 45.46, 44.86, 44.58, 33.80, 33.64, 26.21, 24.96, 21.92; ESI MS + 1 m/z 299. |
| 3 | 3,4-dichlorophenyl-cyclohexyl-N-methylpyrrolidine | A B C D E F G J | ¹H NMR (400 MHz, CD₃OD) δ 7.48 (d, J = 2.0 Hz, 1 H), 7.47 (d, J = 8.8 Hz, 1 H), 7.30 (dd, J = 2.0, 8.8 Hz, 1 H), 2.7-2.64 (m, 1 H), 2.56 (t, J = 8.4 Hz, 1 H), 2.34-2.27 (m, 1 H), 2.24 (s, 3 H), 2.24-2.18 (m, 2 H), 2.18-2.13 (m, 1 H), 1.70-1.50 (m, 1 H), 1.38-1.10 (m, 4 H); ¹³C NMR (100 MHz, CD₃OD) δ 144.97, 138.85, 132.04, 130.23, 130.08, 128.16, 56.55, 55.61, 50.82, 43.34, 41.33, 33.44, 32.95, 26.45, 25.45, 22.03; ESI MS + 1 m/z 312. |
| 4 | 3,4-dichlorophenyl-cyclohexyl-N-methylpyrrolidine | A B C D E F G J | ¹H NMR (400 MHz, CD₃OD) δ 7.48 (d, J = 2.0 Hz, 1 H), 7.47 (d, J = 8.8 Hz, 1 H), 7.30 (dd, J = 2.0, 8.8 Hz, 1 H), 2.7-2.64 (m, 1 H), 2.56 (t, J = 8.4 Hz, 1 H), 2.34-2.27 (m, 1 H), 2.24 (s, 3 H), 2.24-2.18 (m, 2 H), 2.18-2.13 (m, 1 H), 1.70-1.50 (m, 1 H), 1.38-1.10 (m, 4 H); ¹³C NMR (100 MHz, CD₃OD) δ 144.97, 138.85, 132.04, 130.23, 130.08, 128.16, 56.55, 55.61, 50.82, 43.34, 41.33, 33.44, 32.95, 26.45, 25.45, 22.03; ESI MS + 1 m/z 312. |
| 5 | 3,4-dichlorophenyl-cyclopentyl-pyrrolidine (NH) | A B C D E F G | ¹H NMR (400 MHz, CD₃OD) δ 7.52 (d, J = 2.0 Hz, 1 H), 7.48 (d, J = 8.4 Hz, 1 H), 7.32 (dd, J = 2.0 Hz, 1 H), 3.232-3.28 (m, 2 H), 3.22-3.15 (m, 2 H), 2.75-2.60 (m, 2 H), 2.12-2.05 (m, 2 H), 2.05-1.90 (m, 2 H), 1.85-1.70 (m, 2 H), 1.64-1.50 (m, 2 H); ¹³C NMR (100 MHz, CD₃OD) δ 145.82, 132.07, 130.19, 129.82, 130.11, 127.77, 51.39, 47.22, 46.63, 45.09, 35.58, 26.40, 22.70, 22.64; ESI MS + 1 m/z 284. |
| 6 | 3,4-dichlorophenyl-cyclopentyl-pyrrolidine (NH) | A B C D E F G | ¹H NMR (400 MHz, CD₃OD) δ 7.52 (d, J = 2.0 Hz, 1 H), 7.48 (d, J = 8.4 Hz, 1 H), 7.32 (dd, J = 2.0 Hz, 1 H), 3.232-3.28 (m, 2 H), 3.22-3.15 (m, 2 H), 2.75-2.60 (m, 2 H), 2.12-2.05 (m, 2 H), 2.05-1.90 (m, 2 H), 1.85-1.70 (m, 2 H), 1.64-1.50 (m, 2 H); ¹³C NMR (100 MHz, CD₃OD) δ 145.82, 132.07, 130.19, 129.82, 130.11, 127.77, 51.39, 47.22, 46.63, 45.09, 35.58, 26.40, 22.70, 22.64; ESI MS + 1 m/z 284. |

TABLE 2-continued

Compounds

| Cpd. No. | Structure | Generic Methods | Data |
|---|---|---|---|
| 7 | (3,4-dichlorophenyl)(cyclobutyl)-pyrrolidine | A B C D E H I | ¹H NMR (400 MHz, CD₃OD) δ 7.47 (d, J = 8.8 Hz, 1 H), 7.34 (s, 1 H), 7.12 (d, J = 8.8 Hz, 1 H), 3.30-3.19 (m, 3 H), 2.85-2.71 (m, 2 H), 2.39 (m, 4 H), 2.08-1.89 (m, 2 H), 1.87 (m, 1 H), 1.70 (m, 1 H); ¹³C NMR (100 MHz, CD₃OD) δ 148.94, 132.00, 130.25, 129.80, 128.59, 126.48, 47.63, 46.18, 46.13, 45.16, 31.09, 30.74, 26.01, 15.38; ESI MS + 1 m/z 270. |
| 8 | (3,4-dichlorophenyl)(cyclobutyl)-pyrrolidine | A B C D E H I | ¹H NMR (400 MHz, CD₃OD) δ 7.47 (d, J = 8.8 Hz, 1 H), 7.34 (s, 1 H), 7.12 (d, J = 8.8 Hz, 1 H), 3.30-3.19 (m, 3 H), 2.85-2.71 (m, 2 H), 2.39 (m, 4 H), 2.08-1.89 (m, 2 H), 1.87 (m, 1 H), 1.70 (m, 1 H); ¹³C NMR (100 MHz, CD₃OD) δ 148.94, 132.00, 130.25, 129.80, 128.59, 126.48, 47.63, 46.18, 46.13, 45.16, 31.09, 30.74, 26.01, 15.38; ESI MS + 1 m/z 272. |
| 9 | (naphthyl)(cyclohexyl)-pyrrolidine | A B C D E F G | ¹H NMR (400 MHz, CD₃OD) δ 7.92-7.81 (m, 4 H), 7.58-7.52 (m, 1 H), 7.50-7.40 (m, 2 H), 3.28-3.20 (m, 1 H), 3.18-3.02 (m, 2 H), 2.86-2.78 (m, 1 H), 2.60-2.40 (m, 3 H), 2.04-1.94 (m, 1 H), 1.72-1.50 (m, 5 H), 1.40-1.28 (m, 2 H); ¹³C NMR (100 MHz, CD₃OD) δ 138.81, 133.79, 132.24, 127.97, 127.88, 127.41, 127.14, 125.96, 125.84, 125.83, 50.69, 45.73, 44.98, 42.72, 34.55, 34.03, 26.38, 23.11, 22.11; ESI MS + 1 m/z 279. |
| 10 | (naphthyl)(cyclohexyl)-pyrrolidine | A B C D E F G | ¹H NMR (400 MHz, CD₃OD) δ 7.92-7.81 (m, 4 H), 7.58-7.52 (m, 1 H), 7.50-7.40 (m, 2 H), 3.28-3.20 (m, 1 H), 3.18-3.02 (m, 2 H), 2.86-2.78 (m, 1 H), 2.60-2.40 (m, 3 H), 2.04-1.94 (m, 1 H), 1.72-1.50 (m, 5 H), 1.40-1.28 (m, 2 H); ¹³C NMR (100 MHz, CD₃OD) δ 138.81, 133.79, 132.24, 127.97, 127.88, 127.41, 127.14, 125.96, 125.84, 125.83, 50.69, 45.73, 44.98, 42.72, 34.55, 34.03, 26.38, 23.11, 22.11; ESI MS + 1 m/z 279. |
| 11 | (naphthyl)(cyclopentyl)-pyrrolidine | A B C D E F G | ¹H NMR (400 MHz, CD₃OD) δ 7.91-7.70 (m, 4 H), 7.51-7.41 (m, 3 H), 7.50-7.40 (m, 2 H), 5.0 (broad, 1 H), 3.32-3.24 (m, 1 H), 3.14-3.02 (m, 2 H), 2.82-2.64 (m, 2 H), 2.24-2.14 (m, 2 H), 2.00-1.88 (m, 3 H), 1.80-1.70 (m, 2 H), 1.70-1.50 (m, 3 H); ¹³C NMR (100 MHz, CD₃OD) δ 141.82, 133.50, 132.39, 127.92, 127.81, 127.23, 126.21, 126.05, 125.78, 51.58, 46.89, 46.77, 36.17, 35.59, 22.87, 22.82; ESI MS + 1 m/z 265. |
| 12 | (naphthyl)(cyclopentyl)-pyrrolidine | A B C D E F G | ¹H NMR (400 MHz, CD₃OD) δ 7.91-7.70 (m, 4 H), 7.51-7.41 (m, 3 H), 7.50-7.40 (m, 2 H), 5.0 (broad, 1 H), 3.32-3.24 (m, 1 H), 3.14-3.02 (m, 2 H), 2.82-2.64 (m, 2 H), 2.24-2.14 (m, 2 H), 2.00-1.88 (m, 3 H), 1.80-1.70 (m, 2 H), 1.70-1.50 (m, 3 H); ¹³C NMR (100 MHz, CD₃OD) δ 141.82, 133.50, 132.39, 127.92, 127.81, 127.23, 126.21, 126.05, 125.78, 51.58, 46.89, 46.77, 36.17, 35.59, 22.87, 22.82; ESI MS + 1 m/z 265. |

TABLE 2-continued
Compounds
| Cpd. No. | Structure | Generic Methods | Data |
|---|---|---|---|
| 13 | 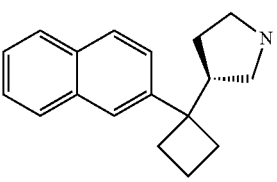 | A B C D E F G | ¹H NMR (400 MHz, CD₃OD) δ 7.84-7.80 (m, 3 H), 7.62 (s, 1 H), 7.48-7.42 (m, 2 H), 7.32-7.29 (m, 1 H), 4.90 (broad, 1 H), 3.30-3.28 (m, 1 H), 3.16-3.13 (m, 2 H), 2.87-2.86 (m, 2 H), 2.60-2.52 (m, 2 H), 2.46-2.41 (m, 2 H), 2.15-2.06 (m, 2 H), 1.96-1.90 (m, 1 H), 1.90-1.71 (m, 1 H); ¹³C NMR (100 MHz, CD₃OD) δ 144.69, 133.44, 132.27, 127.90, 127.63, 127.39, 126.12, 125.62, 124.80, 124.77, 47.80, 46.60; ESI MS + 1 m/z 252. |
| 14 | 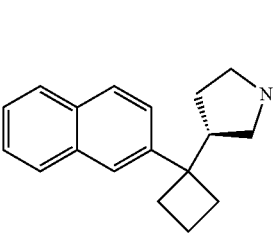 | A B C D E F G | ¹H NMR (400 MHz, CD₃OD) δ 7.84-7.80 (m, 3 H), 7.62 (s, 1 H), 7.48-7.42 (m, 2 H), 7.32-7.29 (m, 1 H), 4.90 (broad, 1 H), 3.30-3.28 (m, 1 H), 3.16-3.13 (m, 2 H), 2.87-2.86 (m, 2 H), 2.60-2.52 (m, 2 H), 2.46-2.41 (m, 2 H), 2.15-2.06 (m, 2 H), 1.96-1.90 (m, 1 H), 1.90-1.71 (m, 1 H); ¹³C NMR (100 MHz, CD₃OD) δ 144.69, 133.44, 132.27, 127.90, 127.63, 127.39, 126.12, 125.62, 124.80, 124.77, 47.80, 46.60; ESI MS + 1 m/z 252. |
Scheme 2 sets forth an exemplary route to synthesis of cyclic ether pyrrolidines of the invention, e.g., 15 and 16.
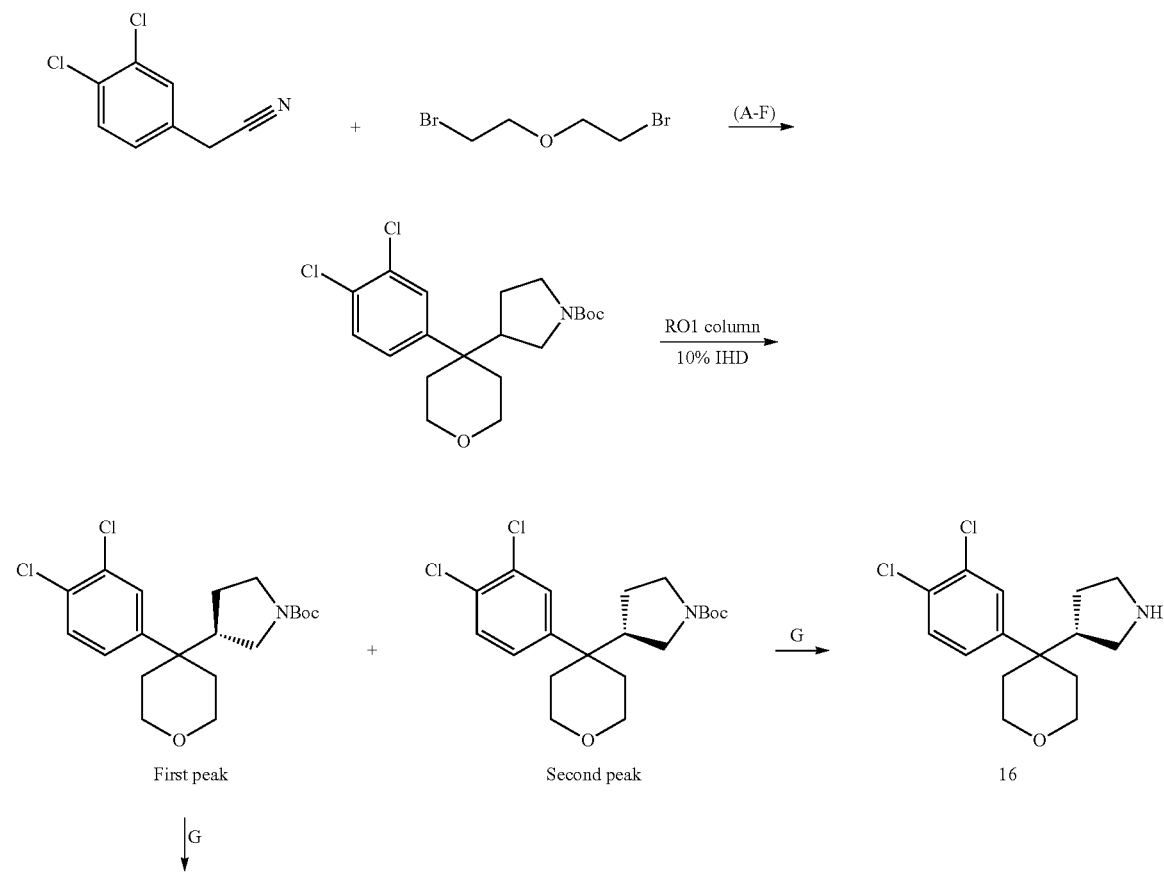
Scheme 2

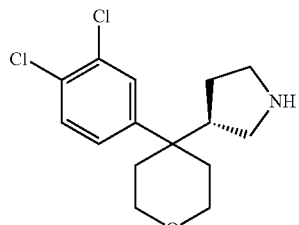

15

Table 3 provides exemplary structures and analytical characteristics of representative cyclic ether pyrrolidines of the invention.

TABLE 3

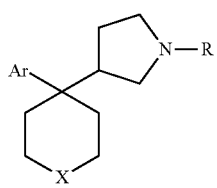

| Cpd. No. | Ar | X | R | Generic Methods | Data |
|---|---|---|---|---|---|
| 15 | 3,4-diCl-phenyl | O | H | A B C D E F G | $^1$H NMR (400 MHz, CD$_3$OD) δ 7.59-7.56 (m, 2 H), 7.36 (d, J = 16.8 Hz, 1 H), 3.79 (d, J = 11.2 Hz, 2 H), 3.39-3.26 (m, 5 H), 2.76 (t, J = 11.6 Hz, 1 H), 2.76 (t, J = 11.6 Hz, 1 H), 2.57 (m, 1 H), 2.32-2.25 (m, 2 H), 1.99-1.89 (m, 3 H), 1.60-1.55 (m, 1 H); $^{13}$C NMR (100 MHz, CD$_3$OD) δ 141.83, 132.82, 130.79, 130.39, 128.30, 63.83, 63.76, 49.31, 45.33, 45.09, 40.77, 34.02, 33.75, 24.85; ESI MS + 1 m/z 300. |
| 16 | 3,4-diCl-phenyl | O | H | A B C D E F G | $^1$H NMR (400 MHz, CD$_3$OD) δ 7.59-7.56 (m, 2 H), 7.36 (d, J = 16.8 Hz, 1 H), 3.79 (d, J = 11.2 Hz, 2 H), 3.39-3.26 (m, 5 H), 2.76 (t, J = 11.6 Hz, 1 H), 2.76 (t, J = 11.6 Hz, 1 H), 2.57 (m, 1 H), 2.32-2.25 (m, 2 H), 1.99-1.89 (m, 3 H), 1.60-1.55 (m, 1 H); $^{13}$C NMR (100 MHz, CD$_3$OD) δ 141.83, 132.82, 130.79, 130.39, 128.30, 63.83, 63.76, 49.31, 45.33, 45.09, 40.77, 34.02, 33.75, 24.85; ESI MS + 1 m/z 300. |

Scheme 3

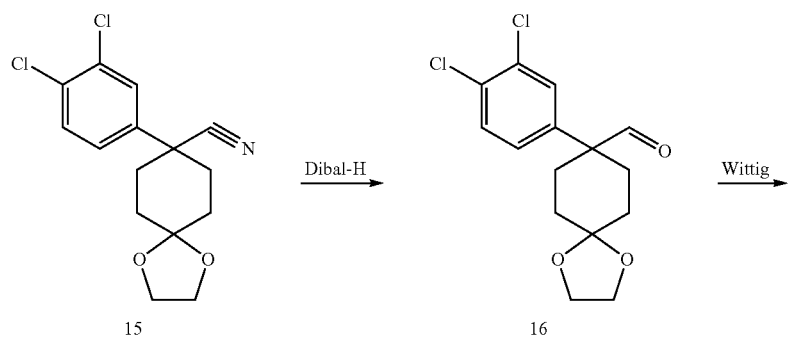

-continued
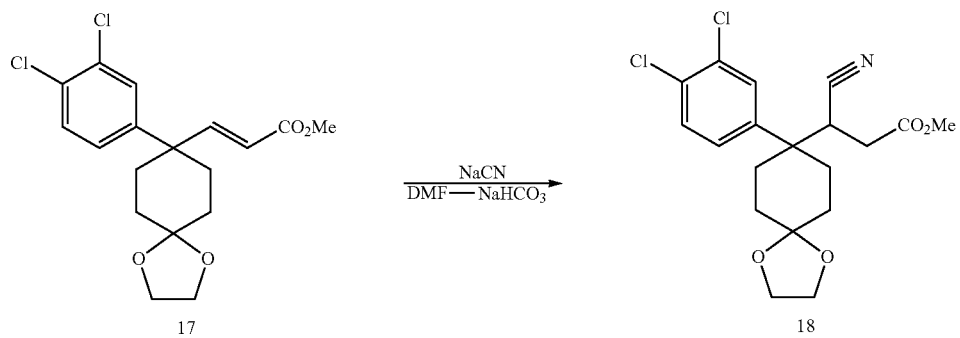
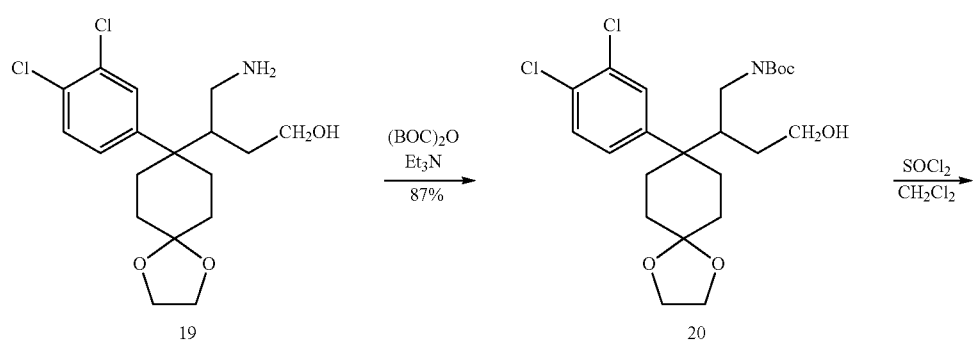
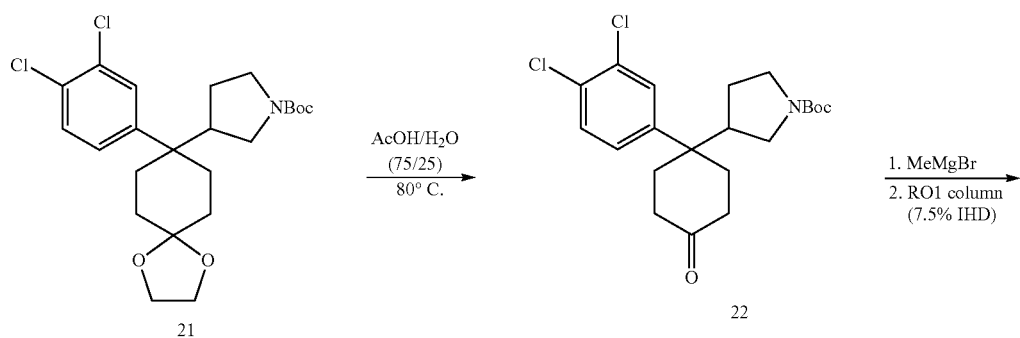
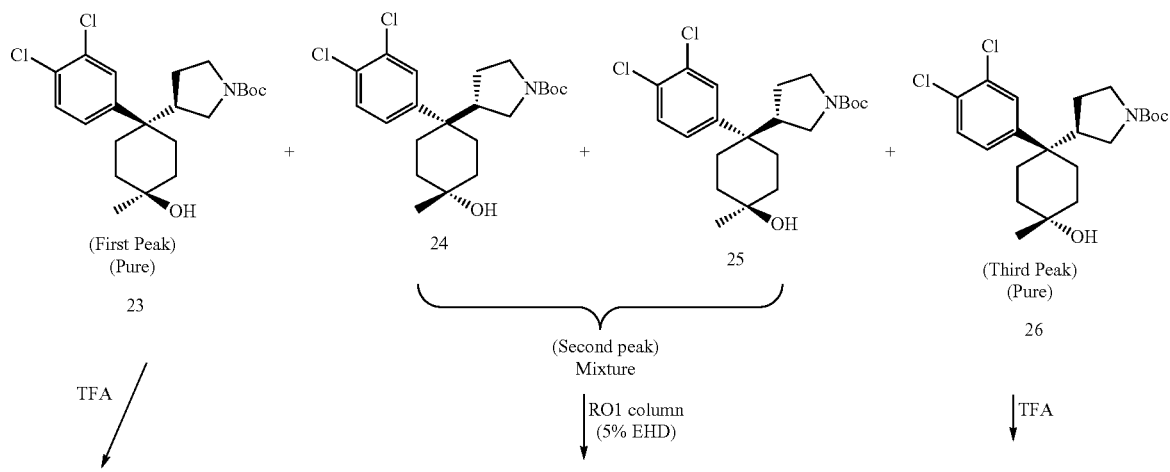

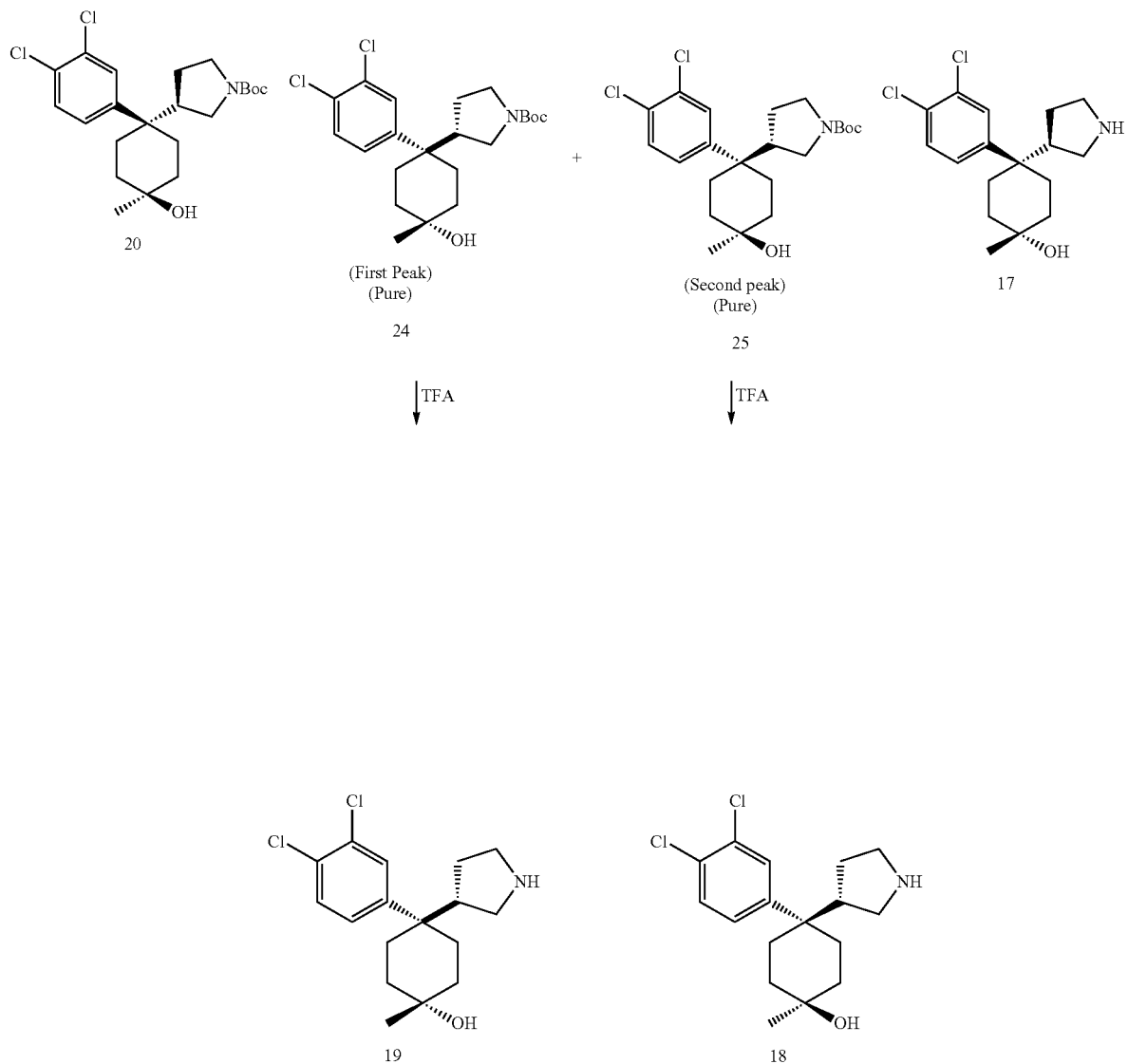

Scheme 3 provides an exemplary route to substituted cycloalkyl derivatives of the invention through a ketone precursor. General procedures B, C, F, E were used to prepare compound 21.

K: Selective Deprotection of the Ketone.

To a solution of 21 (7 g, 15.4 mmol) in a mixture of THF (20 mL) and H$_2$O (50 mL) was added AcOH (150 mL). The reaction mixture was stirred at 80° C. for 1.5 h before being concentrated at reduced pressure. The residue was purified by silica gel column chromatography (gradient, Hexane/ethyl acetate from 100:0 to 0:100) to give 22 (4.69 g, 74%) and recovered starting material (1.3 g).

L: 1,2 Addition of MeMgBr to Ketone and Deprotection:

The following steps are illustrated in Scheme 4. To a solution of 22 (4.0 g, 9.7 mmoL) in THF (40 mL) at −78° C. was added MeMgBr (3 M in diethyl ether, 19.4 mmoL, 6.4 mL). The reaction mixture was stirred for 10 min before being quenched by saturated NH$_4$Cl (20 mL). The product was extracted with CH$_2$Cl$_2$ (100 mL×3), dried and concentrated. The residue was then purified by silica gel column chromatography (gradient, Hexane/ethyl acetate from 100:0 to 0:100) to give a mixture of 23, 24, 25, 26 (3.6 g,). The mixture was separated by chiral column (RO1, 7.5% IHD). The enantiomer 23 (first peak) and 26 (last peak) were obtained. The mixture of 24 and 25 (the second peak) was further separated by chiral RO1 column (5% EHD as eluent) to give 24 (the first peak) and 25 (the second peak). Deprotection of N-Boc groups in 23, 24, 25, 26 with TFA afforded 20, 19, 18 and 17.

M: Reduction of Ketone and Deprotection:

Treatment of compound 22 with N—Selectride in CH$_2$Cl$_2$ at −78° C. gave the two pairs of racemic compounds Rac1 and Rac2 (ratio of Rac1:Rac2=1:1.5). Separation of the four compounds with RO1 (5% EHD as eleut) provided 27 (the first peak), a mixture of 28 and 29 (the second peak), and 30 (the third peak). 28 and 29 were then separated by reverse phase (MeCN/H$_2$O, gradient, from 5% MeCN to 100% MeCN). Deprotection of the N-Boc group in 27, 28, 29 and 30 afforded the compounds 21, 22, 23 and 24.

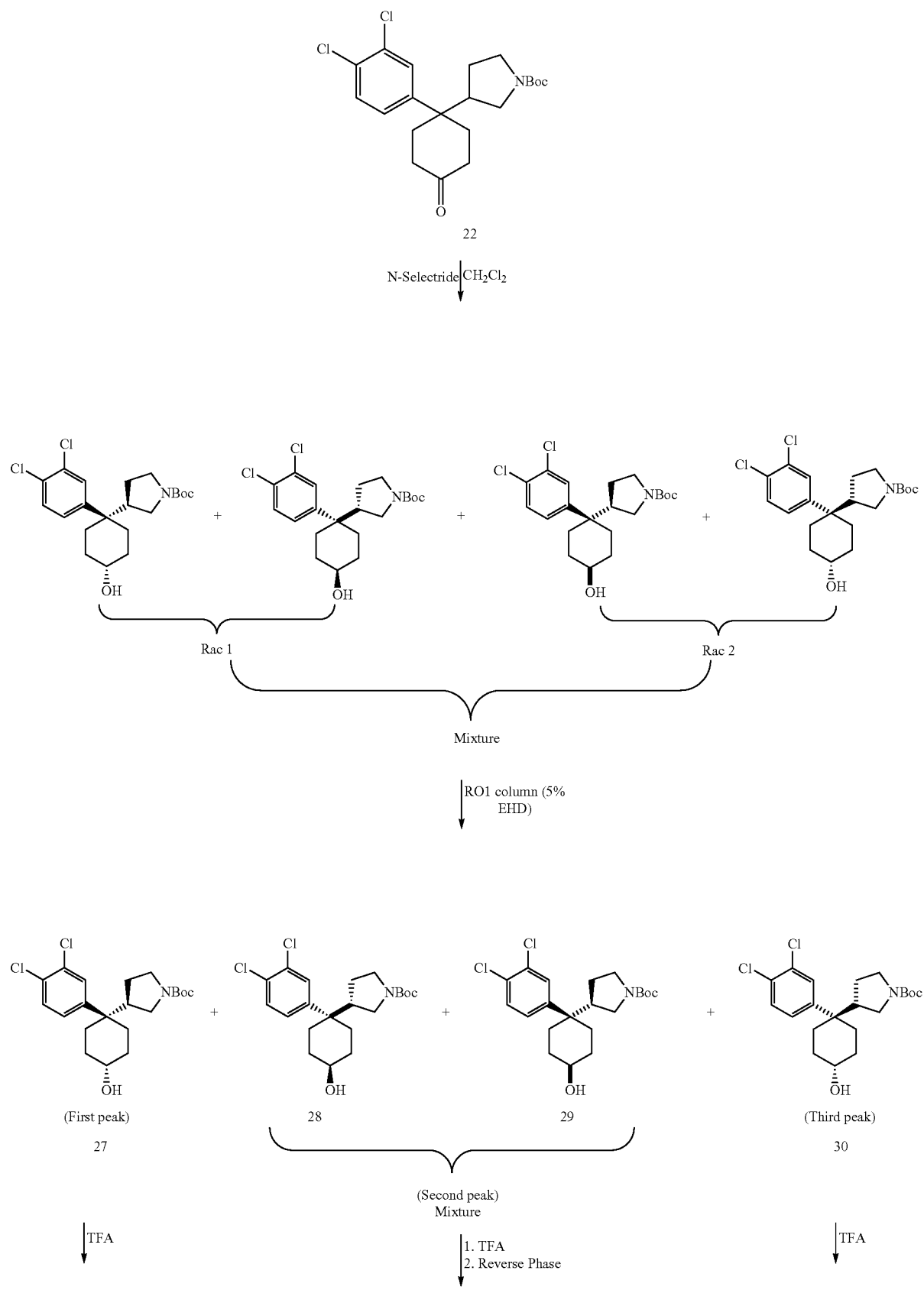

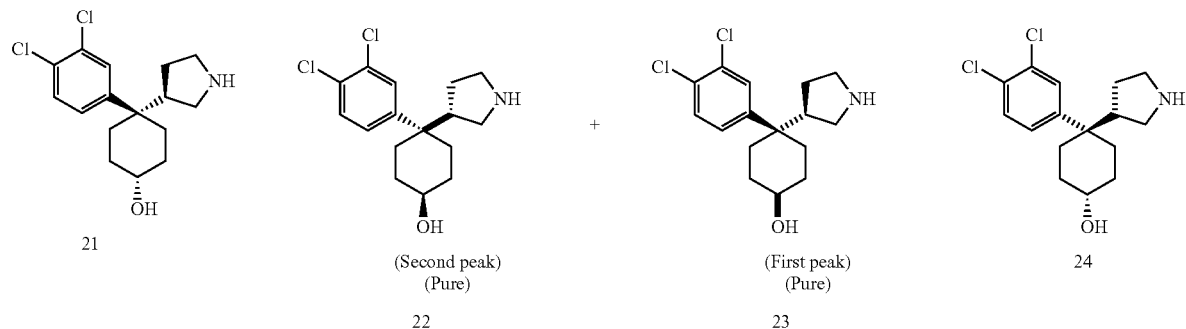

Scheme 4 provides an exemplary route to the reduction of the cycloalkyl ketone and the resolution of the resulting mixture of stereoisomers.

N: Methylation and Deprotection:

Scheme 5 sets forth an exemplary route to methylation and deprotection of various substrates to form compounds of the invention. Treatment of compounds 23, 24, 25, 26 with NaH and iodomethane provided methylated compounds 31, 32, 33, 34 respectively. Removal of the N-Boc protecting groups afforded 25, 26, 27 and 28.

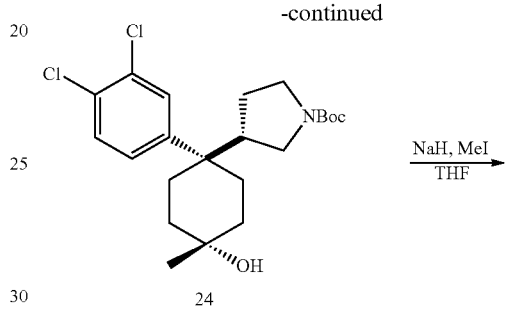

Scheme 5

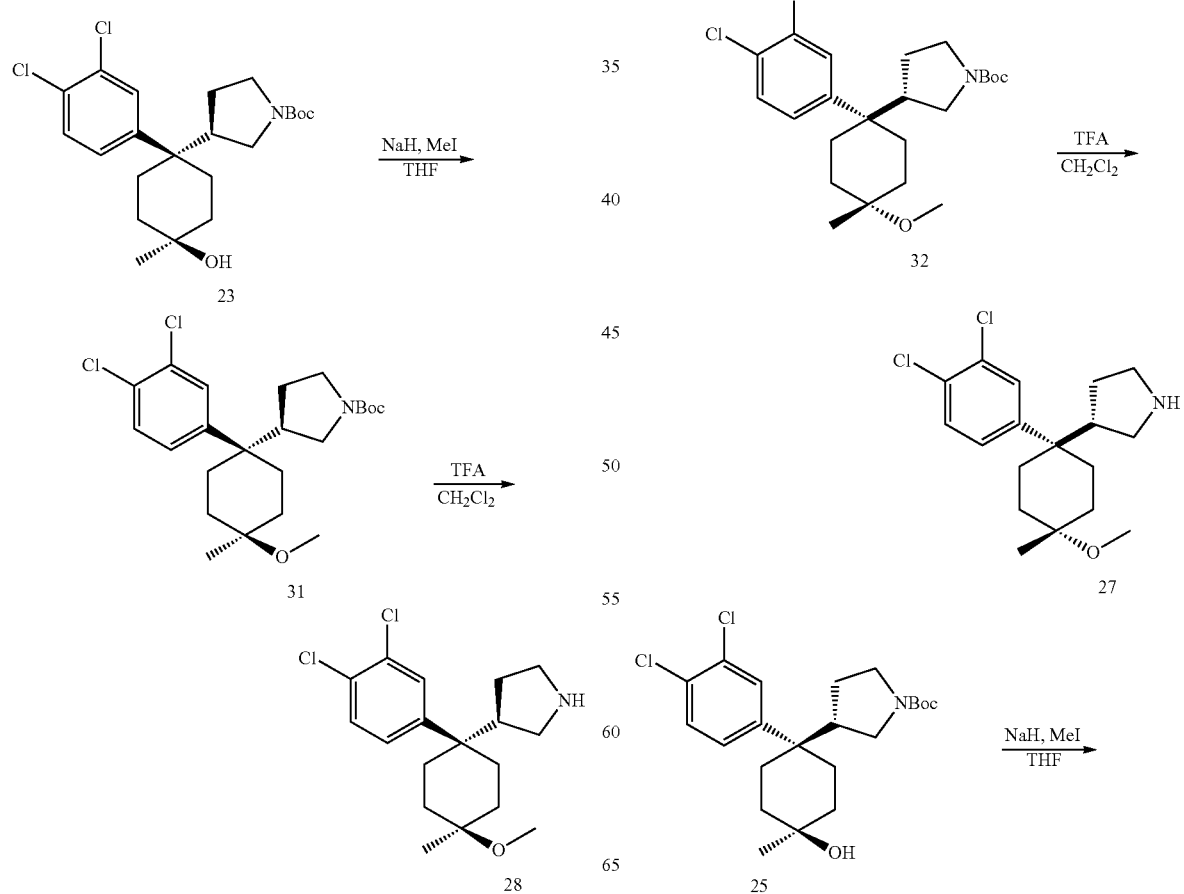

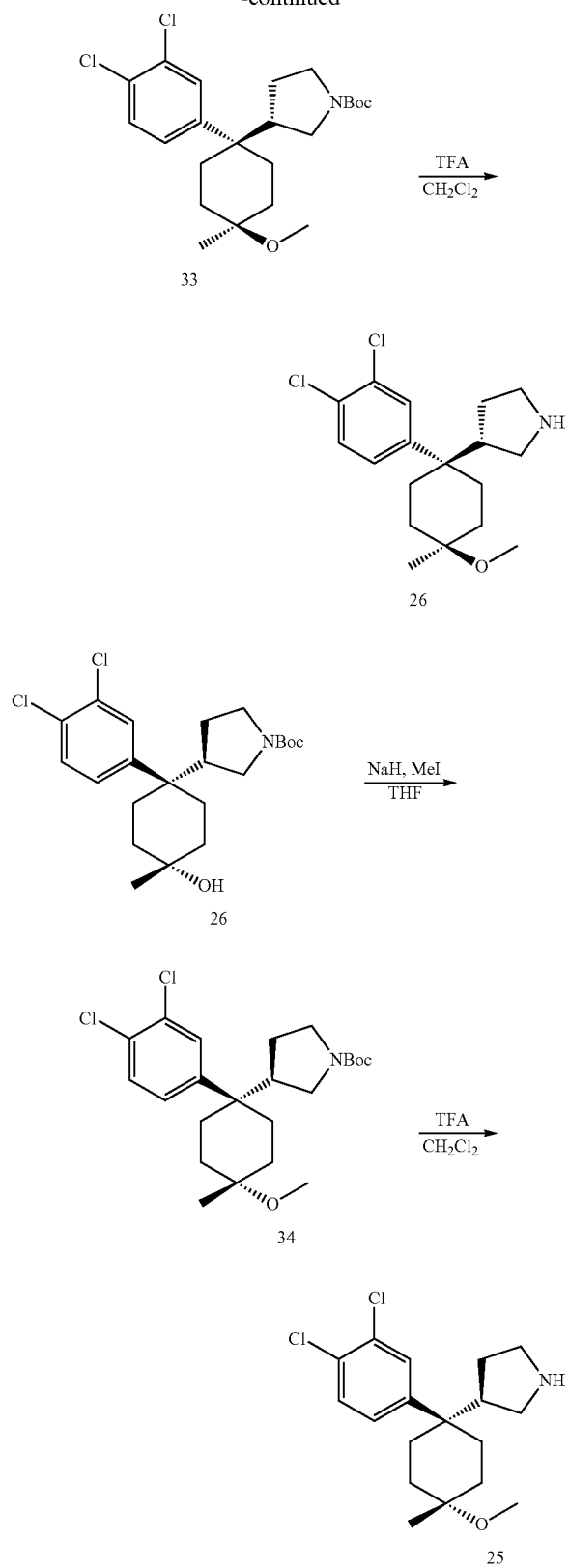

TABLE 4

[Structure: 3,4-dichlorophenyl cyclohexyl pyrrolidine with R1, R2 on cyclohexane and R3 on N]

| Cpd. No. | R₁ | R₂ | R₃ | Generic Methods | Data |
|---|---|---|---|---|---|
| 17 | Me | OH | H | B C F E K L | $^1$H NMR (400 MHz, CD$_3$OD) δ 7.58-7.54 (m, 2 H), 7.39-7.37 (m, 1 H), 3.21-3.08 (m, 2 H), 2.80-2.70 (m, 1 H), 2.70-2.55 (m, 1 H), 2.40-2.20 (m, 2 H), 2.05-1.85 (m, 2 H), 1.80-1.62 (m, 2 H), 1.62-1.40 (m, 5 H), 1.27 (m, 3 H); $^{13}$C NMR (100 MHz, DMSO) δ 154.08, 131.59, 130.69, 130.65, 129.27, 129.17, 46.74, 45.99, 45.74, 40.85, 40.62, 39.58, 36.38, 31.99, 31.20, 27.56, 26.69; ESI MS + 1 m/z 328. |
| 18 | Me | OH | H | B C F E K L | $^1$H NMR (400 MHz, CD$_3$Cl$_3$) δ 7.58-7.54 (m, 2 H), 7.39-7.37 (m, 1 H), 3.21-3.08 (m, 2 H), 2.80-2.70 (m, 1 H), 2.70-2.55 (m, 1 H), 2.40-2.20 (m, 2 H), 2.05-1.85 (m, 2 H), 1.80-1.62 (m, 2 H), 1.62-1.40 (m, 5 H), 1.27 (m, 3 H); $^{13}$C NMR (100 MHz, DMSO) δ 154.08, 131.59, 130.69, 130.65, 129.27, 129.17, 46.74, 45.99, 45.74, 40.85, 40.62, 39.58, 36.38, 31.99, 31.20, 27.56, 26.69; ESI MS + 1 m/z 328. |
| 19 | Me | OH | H | B C F E K L | $^1$H NMR (400 MHz, DMSO) δ 7.55 (m, 2 H), 7.46 (m, 1 H), 3.30-3.00 (m, 3 H), 2.90-2.70 (m, 1 H), 2.45-2.25 (m, 1 H), 2.20-2.00 (m, 2 H), 2.00-1.80 (m, 3 H), 1.70-1.40 (m, 3 H), 1.16-1.05 (m, 3 H), 1.01 (s, 3 H); $^{13}$C NMR (100 MHz, DMSO) δ 143.46, 131.91, 131.02, 130.74, 129.55, 129.26, 67.42, 50.53, 45.43, 44.69, 42.52, 40.86, 40.61, 35.24, 31.74, 26.82, 23.56; ESI MS + 1 m/z 328. |
| 20 | Me | OH | H | B C F E K L | $^1$H NMR (400 MHz, CD$_3$OD) δ 7.55 (m, 2 H), 7.46 (m, 1 H), 3.30-3.00 (m, 3 H), 2.90-2.70 (m, 1 H), 2.45-2.25 (m, 1 H), 2.20-2.00 (m, 2 H), 2.00-1.80 (m, 3 H), 1.70-1.40 (m, 3 H), 1.16-1.05 (m, 3 H), 1.01 (s, 3 H); $^{13}$C NMR (100 MHz, CD$_3$OD) δ 143.46, 131.91, 131.02, 130.74, 129.55, 129.26, 67.42, 50.53, 45.43, 44.69, 42.52, 40.86, 40.61, 35.24, 31.74, 26.82, 23.56; ESI MS + 1 m/z 328. |
| 21 | H | OH | H | B C F E K M | $^1$H NMR (400 MHz, CD$_3$OD) δ 7.54 (d, J = 2.0 Hz, 1 H), 7.52 (d, J = 8.8 Hz, 1 H), 7.33 (dd, J = 8.8, 2.0 Hz, 1 H), 5.0 (broad, 2 H), 3.70-3.61 (m, 1 H), 3.61-3.54 (m, 1 H), 3.36-3.35 (m, 1 H), 3.13 (d, J = 12.8 Hz, 1 H), 2.43-2.34 (m, 3 H), 2.00-1.96 (m, 1 H), 1.84-1.74 (m, 2 H), 1.74-1.64 (m, 1 H), 1.64-1.55 (m, 3 H), 1.22-1.16 (m, 3 H); $^{13}$C NMR (100 MHz, CD$_3$OD) δ 143.10, 132.57, 130.51, 130.30, 128.16, 69.97, 60.88, 47.47, 44.46, 41.56, 32.13, 31.06, 30.93, 30.89, 30.56; ESI MS + 1 m/z 314. |
| 22 | H | OH | H | B C F E K M | $^1$H NMR (400 MHz, CD$_3$OD) δ 7.54 (d, J = 2.0 Hz, 1 H), 7.52 (d, J = 8.8 Hz, 1 H), 7.33 (dd, J = 8.8, 2.0 Hz, 1 H), 5.0 (broad, 2 H), 3.70-3.61 (m, 1 H), 3.61-3.54 (m, 1 H), 3.36-3.35 (m, 1 H), 3.13 (d, J = 12.8 Hz, 1 H), 2.43-2.34 (m, 3 H), 2.00-1.96 (m, 1 H), 1.84-1.74 (m, 2 H), 1.74-1.64 (m, 1 H), 1.64-1.55 (m, 3 H), 1.22-1.16 (m, |

Table 4 sets forth structures of exemplary compounds of the invention, the generic procedures used to synthesize them, and analytical data acquired from these compounds.

TABLE 4-continued

[Structure: 3,4-dichlorophenyl-cyclohexyl-pyrrolidine with R1, R2, R3 substituents]

| Cpd. No. | R1 | R2 | R3 | Generic Methods | Data |
|---|---|---|---|---|---|
| | | | | | 3 H); ¹³C NMR (100 MHz, CD₃OD) δ 143.10, 132.57, 130.51, 130.30, 128.16, 69.97, 60.88, 47.47, 44.46, 41.56, 32.13, 31.06, 30.93, 30.89, 30.56; ESI MS + 1 m/z 314. |
| 23 | H | OH | H | B C F E K M | ¹H NMR (400 MHz, CD₃Cl₃) δ 7.45 (d, J = 8.0 Hz, 1 H), 7.34 (s, 1 H), 7.11 (d, J = 8.0 Hz, 1 H), 3.65 (m, 1 H), 3.35-3.05 (m, 2 H), 2.7 (m, 1 H), 2.40-2.20 (m, 2 H), 1.95-1.80 (m, 2 H), 1.80-1.40 (m, 6 H), 1.25-1.18 (m, 1 H); ¹³C NMR (100 MHz, DMSO) δ 143.67, 132.03, 131.14, 130.85, 129.58, 129.36, 69.56, 50.08, 45.47, 44.65, 42.54, 40.90, 39.65, 31.97, 31.88, 25.76; ESI MS + 1 m/z 314. |
| 24 | H | OH | H | B C F E K M | ¹H NMR (400 MHz, CD₃Cl₃) δ 7.45 (d, J = 8.0 Hz, 1 H), 7.34 (s, 1 H), 7.11 (d, J = 8.0 Hz, 1 H), 3.65 (m, 1 H), 3.35-3.05 (m, 2 H), 2.7 (m, 1 H), 2.40-2.20 (m, 2 H), 1.95-1.80 (m, 2 H), 1.80-1.40 (m, 6 H), 1.25-1.18 (m, 1 H); ¹³C NMR (100 MHz, DMSO) δ 143.67, 132.03, 131.14, 130.85, 129.58, 129.36, 69.56, 50.08, 45.47, 44.65, 42.54, 40.90, 39.65, 31.97, 31.88, 25.76; ESI MS + 1 m/z 314. |
| 25 | Me | OMe | H | B C F E K N | ¹H NMR (400 MHz, CD₃Cl₃) δ 7.43 (d, J = 8.0 Hz, 1 H), 7.36 (d, J = 2.4 Hz, 1 H), 7.13 (dd, J = 8.4, 2.4 Hz, 1 H), 3.15 (s, 3 H), 3.14-3.00 (m, 2 H), 2.7 (t, J = 11.2 Hz, 1 H), 2.33 (m, 1 H), 2.0-1.90 (m, 3 H), 1.90-1.75 (m, 3 H), 1.75-1.62 (m, 3 H), 1.62-1.50 (m, 1 H), 1.10-1.03 (m, 2 H), 0.95 (s, 3 H); ¹³C NMR (100 MHz, CD₃Cl₃) δ 142.02, 133.23, 131.04, 130.90, 129.81, 127.18, 72.44, 50.97, 48.77, 45.46, 44.60, 42.07, 31.68, 31.54, 28.28, 25.49, 24.64; ESI MS + 1 m/z 342. |
| 26 | Me | OMe | H | B C F E K N | ¹H NMR (400 MHz, CD₃Cl₃) δ 7.43 (d, J = 8.0 Hz, 1 H), 7.36 (d, J = 2.4 Hz, 1 H), 7.13 (dd, J = 8.4, 2.4 Hz, 1 H), 3.15 (s, 3 H), 3.14-3.00 (m, 2 H), 2.7 (t, J = 11.2 Hz, 1 H), 2.33 (m, 1 H), 2.0-1.90 (m, 3 H), 1.90-1.75 (m, 3 H), 1.75-1.62 (m, 3 H), 1.62-1.50 (m, 1 H), 1.10-1.03 (m, 2 H), 0.95 (s, 3 H); ¹³C NMR (100 MHz, CD₃Cl₃) δ 142.02, 133.23, 131.04, 130.90, 129.81, 127.18, 72.44, 50.97, 48.77, 45.46, 44.60, 42.07, 31.68, 31.54, 28.28, 25.49, 24.64; ESI MS + 1 m/z 342. |
| 27 | Me | OMe | H | B C F E K N | ¹H NMR (400 MHz, CD₃OD) δ 7.84-7.80 (m, 3 H), 7.62 (s, 1 H), 7.48-7.42 (m, 2 H), 7.32-7.29 (m, 1 H), 4.90 (broad, 1 H), 3.30-3.28 (m, 1 H), 3.16-3.13 (m, 2 H), 2.87-2.86 (m, 2 H), 2.60-2.52 (m, 2 H), 2.46-2.41 (m, 2 H), 2.15-2.06 (m, 2 H), 1.96-1.90 (m, 1 H), 1.90-1.71 (m, 1 H); ¹³C NMR (100 MHz, CD₃OD) δ 144.69, 133.44, 132.27, 127.90, 127.63, 127.39, 126.12, 125.62, 124.80, 124.77, 47.80, 46.60; ESI MS + 1 m/z 252. |
| 28 | Me | OMe | H | B C F E K N | ¹H NMR (400 MHz, CD₃OD) δ 7.84-7.80 (m, 3 H), 7.62 (s, 1 H), 7.48-7.42 (m, 2 H), 7.32-7.29 (m, 1 H), 4.90 (broad, 1 H), 3.30-3.28 (m, 1 H), 3.16-3.13 (m, 2 H), 2.87-2.86 (m, 2 H), 2.60-2.52 (m, 2 H), 2.46-2.41 (m, 2 H), 2.15-2.06 (m, 2 H), 1.96-1.90 (m, 1 H), 1.90-1.71 (m, 1 H); ¹³C NMR (100 MHz, CD₃OD) δ 144.69, 133.44, 132.27, 127.90, 127.63, 127.39, 126.12, 125.62, 124.80, 124.77, 47.80, 46.60; ESI MS + 1 m/z 252. |

Scheme 6

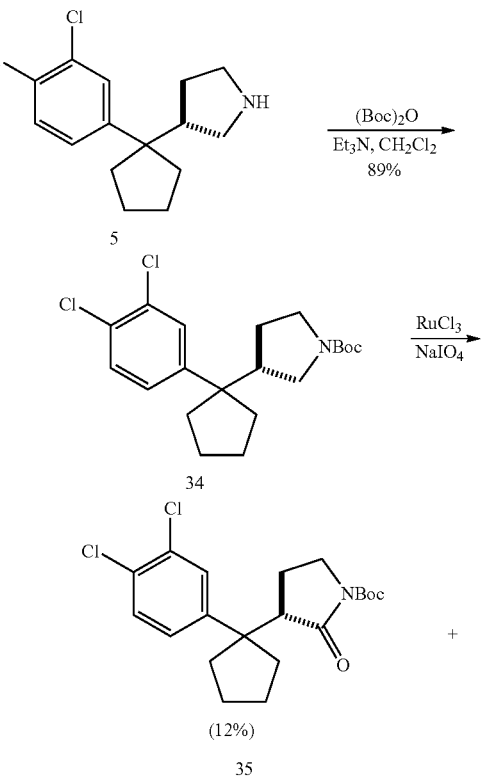

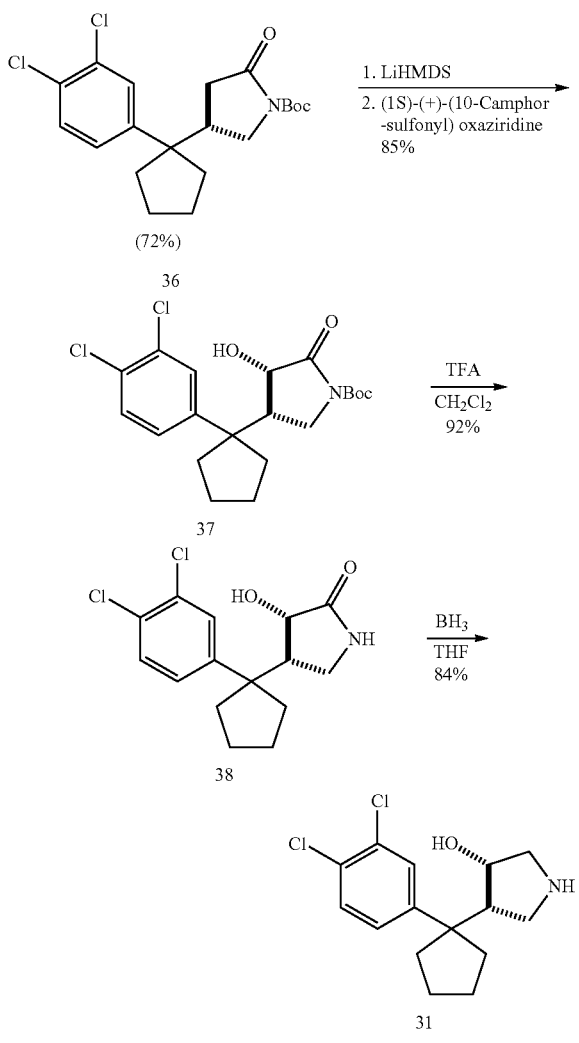

O: RuCl₃-NaIO₄ Oxidation:

Scheme 6 sets forth an exemplary oxidateive route to compounds of the invention utilizing ruthenium as the oxidant. To the compound 34 (3 g, 7.8 mmol) in $CH_3CN$ (100 mL) and $H_2O$ (5 mL) was added $RuCl_3.6H_2O$ (0.5 g) and $NaIO_4$ (3.3 g, 15.7 mmol). The reaction mixture was stirred for 8 h before being concentrated. The residue was extracted with $CH_2Cl_2$ (3×50 mL). The combined $CH_2Cl_2$ solution was dried and concentrated. The residue was purified by silica gel column chromatography (ethyl acetate/hexane, gradient, 0% to 100% ethyl acetate) to give the desired product 36 (2.2 g, 72%).

P: Alpha-Hydroxylation:

To a solution of 36 (1.5 g, 3.8 mmol) in THF (30 mL) at −78° C. was added LiHMDS (1.0 M in THF, 5 mL, 5.00 mmol). The reaction mixture was stirred for 1 h before a solution of (1S)-(+)-(10-Camphorsulfonyl)oxaziridine (5.0 mmol) in THF (15 mL) was added, followed by HMPA (1 mL). The reaction mixture was stirred for 2 h at −78° C. and then was warmed to −20° C. before being quenched by saturated $NH_4Cl$ solution (10 mL). The reaction mixture was then concentrated to remove most of THF. The product was extracted with $CH_2Cl_2$ (3×50 mL) and the combined $CH_2Cl_2$ extracts were dried and concentrated. The residue was purified by silica gel column chromatography (ethyl acetate/hexane, gradient, 0% to 100% for ethyl acetate) to give the desired product 37 (1.3 g, 85%).

Q: Removal of Boc Group

To a solution of 37 (1.0 g, 2.4 mmol), in $CH_2Cl_2$ (15 mL) was added TFA (5 mL). The reaction mixture was stirred for 30 min before being concentrated. The residue was dissolved in $CH_2Cl_2$ (30 mL), washed with NaOH (3 N, 3 mL), dried and concentrated to give 38 (0.69 g, 92%).

R: Borane Reduction of Lactam:

Scheme 7 provides an exemplary route to synthesis of a lactam and the reduction of that lactam with borane. To a solution of 38 (0.5 g, 1.6 mmol) in THF was added $BH_3.THF$ (1.0 M in THF, 6 mL, 6 mmol). The reaction mixture was stirred at reflux for 8 h before being concentrated. The residue was dissolved in MeOH and purified by reversed phase HPLC to give 31 (0.4 g, 84%).

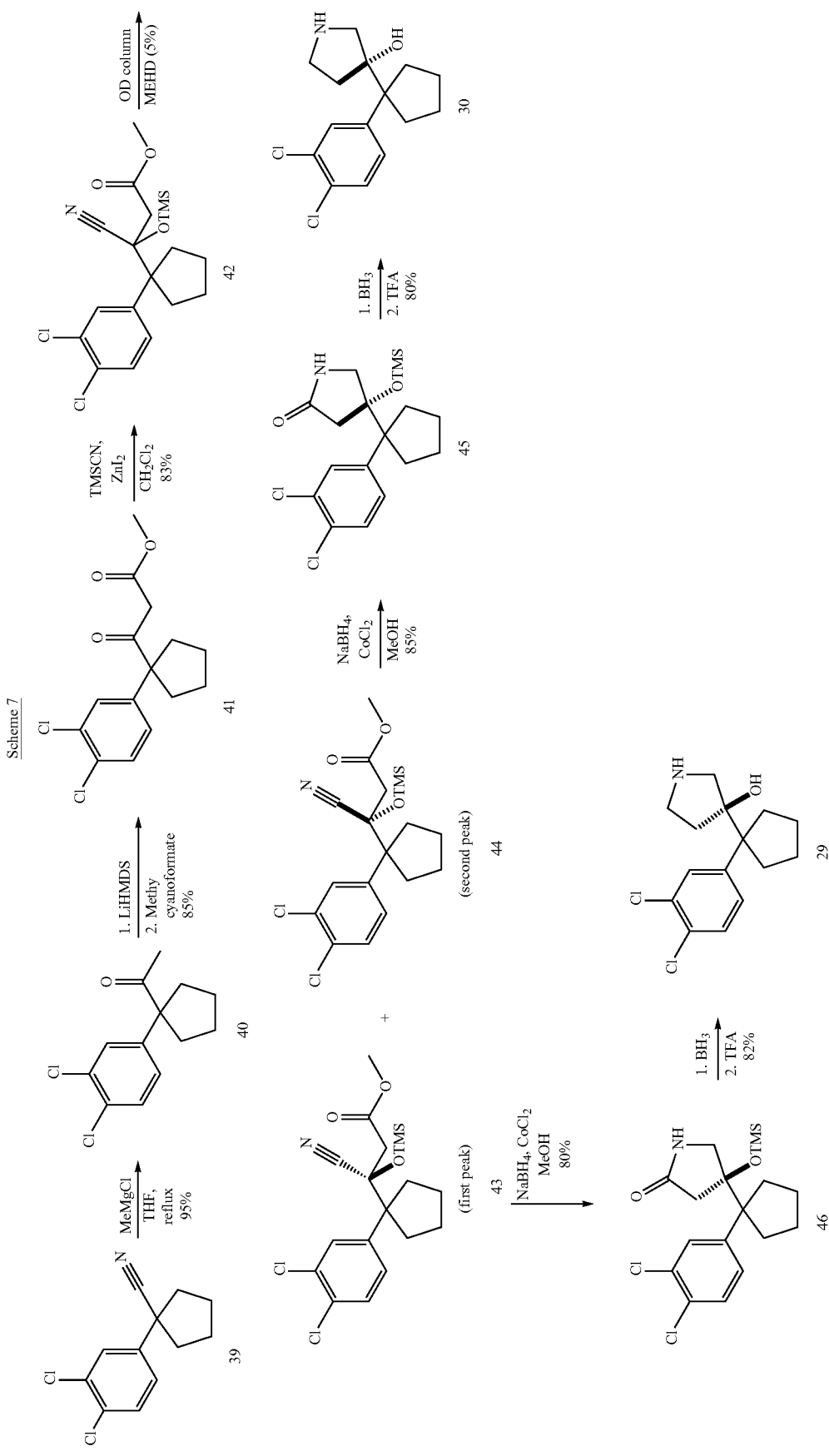

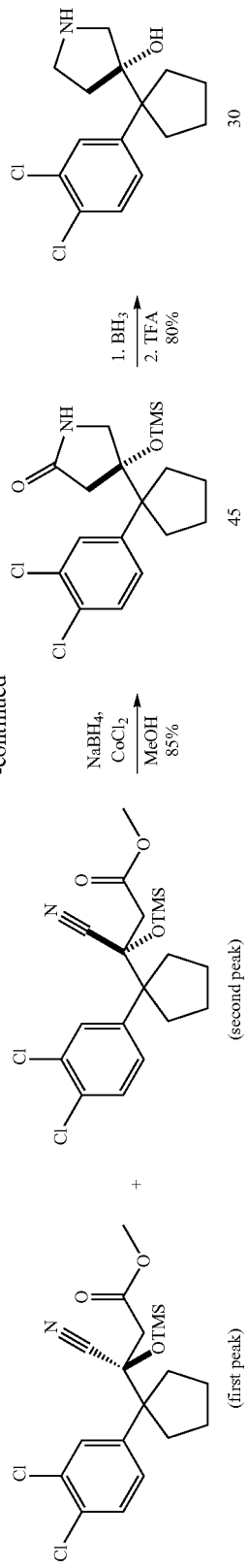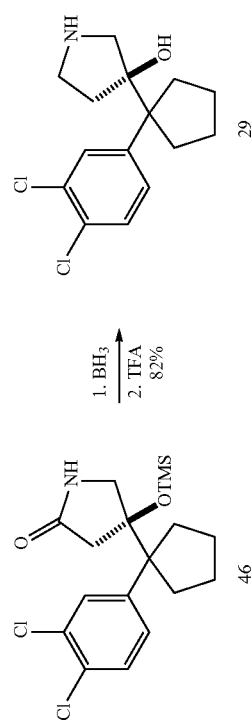

S: Methyl Addition to Cyano Group:

To a solution of 39 (9 g, 37.8 mmol) in THF (150 mL) at −10° C. was added MeMgCl (3 M in THF, 20 mL, 60 mmol). The reaction mixture was stirred for 5 h at reflux before being quenched by NH₄Cl (20 mL). The resulting mixture was concentrated to remove most of THF. The product was then extracted with CH₂Cl₂ (2×100 mL). The combined extracts were dried and concentrated to give 40 (9 g, 95%).

T: Alpha Carboxylation:

To a solution of 40 (9.0 g, 35.2 mmol) in THF at −78° C. was added LiHMDS (1.0 M in THF, 45 mL, 45 mmol) and HMPA (6 mL). The reaction mixture was stirred for 30 min before methyl cyanoformate (3.0 g, 35.2 mmol) was added. The reaction mixture was stirred for 2 h at −78° C. and then warmed to −10° C. over 30 min before being quenched by NH₄Cl (20 mL). The resulting mixture was concentrated to remove most of THF. The product was then extracted with CH₂Cl₂ (2×100 mL). The combined extracts were dried and concentrated. The resulting residue was purified by silica gel column chromatography (ethyl acetate/hexane, gradient, 0% to 100% for ethyl acetate) to give the desired product 41 (9.4 g, 85%).

U: Cyano Group Addition to Ketone and Chiral Separation:

To a solution of 41 (2.11 g, 6.7 mmol) in CH₂Cl₂ (30 mL) was added ZnI₂ (12.8 g, 40.2 mmol) and Me₃SiCN (5.4 mL, 3.99 g, 40.2 mmol). The reaction mixture was stirred overnight. The inorganic solid was filtered. The filtrate was washed with saturated NaHCO₃, dried and concentrated. The resulting residue was purified by silica gel column chromatography (ethyl acetate/hexane, gradient, 0% to 100% ethyl acetate) to give the desired product 42 (2.3 g, 83%).

The racemic mixture of 42 (800 mg) was separated by chiral column RO1 column with 5% MEHD as eluent to give 43 (the first peak, 300 mg) and 44 (the second peak, 280 mg).

V: Reduction of Cyano Group and Cyclization:

To a solution of 43 (300 mg, 0.73 mmol) in MeOH (6 mL) was added CoCl₂·6H₂O (0.52 g, 2.19 mmol) and NaBH₄ (220 mg, 5.84 mmol). The reaction mixture was stirred for 1 h before being concentrated. The residue was washed with CH₂Cl₂ (3×30 mL). The combined CH₂Cl₂ solution was dried and concentrated. Purification of the residue by reverse phase HPLC gave the 45 (192 mg, 85%).

W: Borane Reduction and TMS Deprotection:

To a solution of 45 (150 mg, 0.47 mmol) in THF (5 mL) was added BH₃·THF (1.0 M in THF, 4 mL, 4.0 mmol). The reaction mixture was heated at reflux for 8 h before being concentrated. The residue was quenched by MeOH (2 mL). MeOH was removed and CH₂Cl₂ (5 mL) and TFA (3 mL) were added. The reaction mixture was stirred for 30 min before being concentrated. The residue was purified by reverse phase HPLC (CH₃CN/H₂O, gradient, 10% to 100% in 10 min for MeCN) to give 30 (112 mg, 85%).

Following steps V and W, 29 was obtained from 43. Table 5 sets forth structures of representative compounds of the invention in which the pyrrolidne ring system is substituted.

TABLE 5

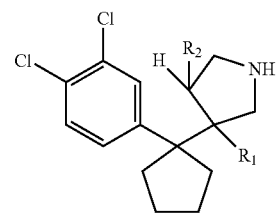

| Cpd. No. | R₁ | R₂ | Generic Methods | Data |
|---|---|---|---|---|
| 29 | OH | H | S T U V W | ¹H NMR (400 MHz, CDCl₃) δ 7.49 (d, J = 2.0 Hz, 1 H), 7.35 (d, J = 8.4 Hz, 1 H), 7.27 (dd, J = 2.0, 8.4 Hz, 1 H), 3.36 (m, 3 H), 3.20 (m, 1 H), 3.00 (s, 2 H), 2.18 (m, 2 H), 1.98 (m, 3 H), 1.78 (m, 3 H), 1.48 (m, 2 H); ¹³C NMR (100 MHz, CDCl₃) 144.50, 133.31, 132.21, 130.91, 129.97, 128.32, 83.66, 56.43, 53.07, 43.57, 34.50, 34.56, 23.99, 23.96; ESI MS + 1 m/z 300. |
| 30 | OH | H | S T U V W | ¹H NMR (400 MHz, CDCl₃) δ 7.49 (d, J = 2.0 Hz, 1 H), 7.35 (d, J = 8.4 Hz, 1 H), 7.27 (dd, J = 2.0, 8.4 Hz, 1 H), 3.36 (m, 3 H), 3.20 (m, 1 H), 3.00 (s, 2 H), 2.18 (m, 2 H), 1.98 (m, 3 H), 1.78 (m, 3 H), 1.48 (m, 2 H); ¹³C NMR (100 MHz, CDCl₃) 144.50, 133.31, 132.21, 130.91, 129.97, 128.32, 83.66, 56.43, 53.07, 43.57, 34.50, 34.56, 23.99, 23.96; ESI MS + 1 m/z 300. |
| 31 | H | OH | O P Q R | ¹H NMR (400 MHz, CDCl₃) δ 7.40 (d, J = 8.4 Hz, 1 H), 7.37 (d, J = 2.0 Hz, 1 H), 7.14 (dd, J = 2.0, 8.4 Hz, 1 H), 4.16 (m, 1 H), 3.29 (m, 1 H), 3.09 (d, J = 11.6 Hz, 1 H), 2.67-2.52 (m, 3 H), 2.06-2.02 (m, 1 H), 2.02-1.84 (m, 5 H), 1.87-1.62 (m, 2 H); ¹³C NMR (100 MHz, CDCl₃) 143.50, 133.10, 132.41, 130.63, 129.73, 127, 72.21, 55.52, 54.10, 51.75, 47.13, 38.78, 37.09, 35.45, 23.05, 22.97; ESI MS + 1 m/z 300. |

Example 2

In Vitro Analyses (Monoamine Uptake Assays)

The compounds of the invention were tested for their inhibition of functional uptake of serotonin (5-HT), norepinephrine (NE), and dopamine (DA), in synaptosomes prepared from rat whole brain, hypothalamus, or corpus striatum, respectively, and/or using recombinant human transporters, as described herein, below. Compounds were initially tested at 10 μM in duplicate. Compounds showing ≥50% inhibition of uptake were further tested at 10 different concentrations in duplicate in order to obtain full inhibition curves. IC₅₀ values (concentration inhibiting control activity by 50%) were then determined by nonlinear regression analysis of the inhibition curves. Results are summarized in Table 6, below.

TABLE 6

| Comp. No. | hSERT (IC₅₀ nM) | hNET (IC₅₀ nM) | hDAT (IC₅₀ nM) |
|---|---|---|---|
| 1 | ++++ | +++ | ++ |
| 2 | ++ | ++ | ++ |
| 3 | + | + | ++ |
| 4 | − | − | +++ |
| 5 | ++ | ++ | ++ |
| 6 | +++ | ++ | ++ |
| 7 | ++ | ++ | +++ |
| 8 | ++ | ++ | ++ |

TABLE 6-continued

| Comp. No. | hSERT (IC$_{50}$ nM) | hNET (IC$_{50}$ nM) | hDAT (IC$_{50}$ nM) |
|---|---|---|---|
| 9 | +++ | + | ++ |
| 10 | ++++ | ++ | ++ |
| 11 | ++++ | +++ | +++ |
| 12 | ++++ | ++++ | ++ |
| 13 | ++ | ++ | ++ |
| 14 | +++ | ++ | ++ |
| 15 | ++ | ++ | ++ |
| 16 | +++ | +++ | +++ |
| 17 | +++ | +++ | ++ |
| 18 | +++ | +++ | ++ |
| 19 | +++ | ++ | +++ |
| 20 | +++ | ++ | +++ |
| 21 | +++ | +++ | ++ |
| 22 | +++ | +++ | +++ |
| 23 | +++ | +++ | +++ |
| 24 | ++++ | ++++ | +++ |
| 25 | +++ | ++ | +++ |
| 26 | ++ | +++ | +++ |
| 27 | +++ | +++ | ++ |
| 28 | ++ | +++ | ++ |
| 29 | +++ | +++ | ++ |
| 30 | ++ | ++ | ++ |
| 31 | ++ | ++ | ++ |

++++ (IC$_{50}$ < 1 nM);
+++ (IC$_{50}$ < 10 nM);
++ (IC$_{50}$ ≤ 100 nM);
+ (100 nM < IC$_{50}$ ≤ 500 nM);
− (IC$_{50}$ > 500 nM);

2.1. Serotonin Functional Uptake Assay for Rat Reuptake Transporter

Quantification of 5-HT uptake was performed using synaptosomes isolated in a 0.32M sucrose buffer from a male Wistar rat cortex. The uptake of radiolabelled 5-HT by synaptosomes (100 μg of proteins/point) was allowed by incubating them in a well for 15 min at 37° C. in presence of test compounds and [$^3$H]5-hydroxytryptamine (serotonin; 0.1 μCi/point).

Synaptosomes and [$^3$H]serotonin were prepared in a Krebs buffer pH 7.4 containing 25 mM NaHCO$_3$, 11 mM glucose and 50 μM ascorbic acid. This incubation buffer was oxygenated during 5 minutes before incubation. Basal control was incubated for 15 minutes at 4° C. in order to avoid any uptake. Following this incubation the uptake was stopped by filtration through a unifilter 96-wells GFB Packard plate washed with Krebs buffer containing 25 mM NaHCO$_3$ in order to eliminate the free [$^3$H]serotonin. The radioactivity associated to the synaptosomes retained on the unifilter corresponding to the uptake was then measured with a microplate scintillation counter (Topcount, Packard) using a scintillation fluid. Non-specific binding was measured in the presence of an excess of cold, unlabeled ligand. Specific binding was obtained by subtracting nonspecific binding from total binding.

The reference compound was imipramine tested at 10 concentrations ranging from 10$^{-11}$ M to 10$^{-5}$ M in order to obtain an IC$_{50}$ value. See, Perovics and Müller, *Arzeim. Forsch./ Drug Res.*, 45:1145-1148 (1995).

2.2. Serotonin Functional Uptake Assay for Human Reuptake Transporter

Inhibition of human serotonin reuptake transporter was assayed using the recombinant human serotonin transporter expressed in HEK-293 cells using a published method (Gu H et al., *J. Biol. Chem.* 1994, 269 (10): 7124-7130). HEK-293 cells expressing human serotonin transporter were plated before the assay. Test compound and/or vehicle was preincubated with cells in modified HEPES buffer pH 7.1 or pH 7.4 for 20 minutes at 18 to 25° C. and 65 nM [$^3$H]serotonin was then added for an additional timed incubation period (ten to thirty minutes). Cells with internalized [$^3$H]serotonin were washed and the amount of tritium taken into cells is counted using a liquid scintillation counter to determine [$^3$H]serotonin uptake. Non-specific binding of tritium was measured in a control reaction containing 10 μM fluoxetine, and was subtracted from the counts for assays to correct for non-specific binding of tritium. Reduction of [$^3$H]serotonin uptake by 50 percent or more (≥50%) relative to an uninhibited control reaction indicates significant inhibitory activity. Compounds were screened at 10, 1, 0.1, 0.01 and 0.001 μM. The reference compound for the assay was fluoxetine, for which the IC$_{50}$ value of 7.1 nM was obtained in a typical experiment.

2.3. Dopamine Functional Uptake Assay for Rat Reuptake Transporter

Quantification of dopamine uptake was performed using synaptosomes isolated in a 0.32 M sucrose buffer from a male Wistar rat striatum. The uptake of radiolabelled dopamine by synaptosomes (20 μg of proteins/point) was allowed by incubating them for 15 minutes at 37° C. in the presence of test compounds and [$^3$H]-dopamine (0.1 μCi/point). The experiment was performed in a deep well.

Synaptosomes and [$^3$H]-dopamine were prepared in a Krebs buffer pH 7.4 containing 25 mM NaHCO$_3$, 11 mM glucose and 50 μM ascorbic acid. This incubation buffer was oxygenated for 5 minutes before incubation. Basal control was incubated for 15 minutes at 4° C. in order to avoid any uptake. Following this incubation, the uptake was stopped by filtration through a unifilter 96-wells GFB Packard plate washed with Krebs buffer containing 25 mM NaHCO$_3$ in order to eliminate free [$^3$H]-dopamine. The radioactivity associated to the synaptosomes retained onto the unifilter corresponding to the uptake was then measured with a microplate scintillation counter (Topcount, Packard) using a scintillation fluid.

The reference compound was GRB12909 tested at 8 concentrations ranging from 10$^{-11}$ M to 10$^{-6}$ M in order to obtain an IC$_{50}$ value. See, Jankowsky et al., *J. Neurochem.* 1986, 46:1272-1276).

2.4. Dopamine Functional Uptake Assay for Human Reuptake Transporter

Inhibition of human dopamine reuptake transporter was assayed using the recombinant human dopamine transporter expressed in either CHO-K1 or HEK293 cells using a published method (Pristupa, Z. B. et al., *Mol. Pharmacol.* 45: 125-135, 1994). Either CHO-K1 or HEK293 cells expressing human recombinant dopamine transporter were plated before the assay. Test compound and/or vehicle was preincubated with cells in modified HEPES buffer pH 7.1 or pH 7.4 for 20 minutes at 18 to 25° C. and 50 nM [$^3$H]dopamine was then added for an additional timed incubation period (10 to 30 minutes). After washing the cells to remove [$^3$H]dopamine not internalized, the cells were lysed, and the amount of tritium in the lysate was measured using a liquid scintillation counter to determine [$^3$H]dopamine uptake. Non-specific binding of tritium was measured in a control reaction containing 10 μM nomifensine, and was subtracted from the counts for assays to correct for non-specific binding of tritium. Reduction of [$^3$H]dopamine uptake by 50 percent or more (50%) relative to an uninhibited control reaction indicates significant inhibitory activity. Compounds were screened at 10, 1, 0.1, 0.01 and 0.001 µM. The reference compound for the assay was nomifensine, for which the $IC_{50}$ value of 11 nM was obtained in a typical experiment.

2.5. Norepinephrine Functional Uptake Assay for Rat Reuptake Transporter

Quantification of norepinephrine uptake was performed using synaptosomes isolated in a 0.32 M sucrose buffer from a male Wistar rat hypothalamus. The uptake of radiolabelled norepinephrine by synaptosomes (100 µg of proteins/point) was allowed by incubating them for 20 minutes at 37° C. in presence of test compounds and [$^3$H]-norepinephrine (0.1 µCi/point). The experiment was performed in a deep well.

Synaptosomes and [$^3$H]-norepinephrine were prepared in a Krebs buffer pH 7.4 containing 25 mM $NaHCO_3$, 11 mM glucose and 50 µM ascorbic acid. This incubation buffer was oxygenated for 5 minutes before incubation. Basal control was incubated for 20 minutes at 4° C. in order to avoid any uptake. Following this incubation, the uptake was stopped by filtration through a unifilter 96-wells GFB Packard plate washed with Krebs buffer containing 25 mM $NaHCO_3$ in order to eliminate the free [$^3$H]-norepinephrine. The radioactivity associated to the synaptosomes retained onto the unifilter corresponding to the uptake was then measured with a microplate scintillation counter (Topcount, Packard) using a scintillation fluid.

The reference compound was protriptyline tested at 13 concentrations ranging from $10^{-11}$ M to $10^{-5}$ M in order to obtain an $IC_{50}$ value. See, Perovics and Müller, *Arzeim. Forsch./Drug Res.*, 45:1145-1148 (1995).

2.6. Norepinephrine Functional Uptake Assay for Human Reuptake Transporter

Inhibition of human norepinephrine reuptake transporter was assayed using the recombinant human norepinephrine transporter expressed in either HEK293 or MDCK cells using a published method (Galli A et al., *J. Exp. Biol.* 198: 2197-2212, 1995). The cells were plated before the assay. Test compound and/or vehicle was preincubated with cells in modified HEPES buffer pH 7.1 or pH 7.4 for 20 minutes at 18 to 25° C. Following the preincubation, 25 nM [$^3$H]norepinephrine was added for an additional timed incubation period (10 to 20 minutes). After the cells were washed to remove [$^3$H]norepinephrine not internalized, the cells were lysed, and the amount of tritium in the cell lysate was measured using a liquid scintillation counter to determine [$^3$H]norepinephrine uptake. Non-specific binding of tritium was measured in a control reaction containing 10 µM imipramine (or 10 µM nisoxetine), and was subtracted from the counts for assays to correct for non-specific binding of tritium. Reduction of [$^3$H] norepinephrine uptake by 50 percent or more (50%) relative to an uninhibited control reaction indicates significant inhibitory activity. Compounds were screened at 10, 1, 0.1, 0.01 and 0.001 µM. The reference compounds for the assay were desipramine and nisoxetine, for which IC50 values of 1.9 nM and 5.3 nM respectively were obtained in typical experiments.

In Table 6, compound numbers correspond to those used in the Examples above. In addition, the following abbreviations have been used in Table 6: SERT (serotonin transporter), NET (norepinephrine transporter) and DAT (dopamine transporter).

The above results indicate that compounds of the invention exhibit potent inhibition of neuronal uptake of NE, DA, and/ or 5-HT, and compare favorably with potencies seen for various existing therapeutic agents. For example, reported potencies ($IC_{50}$ or $K_i$ values) of approved and launched drugs include: fluoxetine (PROZAC®), 7 nM for inhibition of human 5-HT reuptake transporter; methylphenidate (RITALIN®), 193 nM and 38 nM for inhibition of human dopamine and norepinephrine reuptake transporters, respectively (Eshleman et al., *J. Pharmacol. Exp. Ther.* 1999, 289: 877-885); amitriptyline (ELAVIL®), 63 nM and 67 nM for inhibition of the human norepinephrine and serotonin reuptake transporters, respectively and venlafaxine (EFFEXOR®), a so-called serotonin norepinephrine reuptake inhibitor (SNRI) 145 and 1420 nM, for inhibition of the human serotonin, and norepinephrine reuptake transporters respectively (Vaishnavi et al., *Biol. Psychiatry.* 2004, 55: 320-322). The multiple inhibition of the neuronal uptake of NE, DA and/or 5-HT displayed by the compounds of the invention provides the clinician with the ability to more effectively treat CNS disorders, including without limitation affective disorders, cerebral function disorders, anxiety disorders, neuropathic pain, and migraine or migraine headache, by elevating various monoamine levels in the brain simultaneously and over the same dose-range without the need to titrate separate drugs.

Example 3

Ex Vivo Binding Assays

Receptor occupancy of central noradrenaline (NA), 5-HT and dopamine (DA) transporter sites following peripheral administration of compounds was determined using [$^3$H] nisoxetine, [$^3$H] citalopram and [$^3$H] WIN 35428 binding, respectively. Liquid scintillation counting was used to quantify the radioactivity.

3.1. Methods

C57BL/6 mice (25-30 g) were dosed orally with either vehicle or compound at 4 dose levels. Mice were sacrificed 60 minutes after treatment. Whole brains were removed and cortex and striata dissected out before being frozen on dry ice. The brain tissue was stored at −20° C. until the day of the assay. The cortex from each hemisphere was frozen separately. One was used to determine occupancy of NA transporter sites and the other occupancy of 5-HT transporter sites. Striatum was used to determine occupancy of DA transporter sites.

3.2. Membrane Preparation

Frontal cortex from each hemisphere or striata was homogenised individually in ice-cold assay buffer using a tight fitting glass/Teflon homogeniser and used immediately in the binding assay.

[$^3$H] Citalopram Binding to 5-HT Transporter (SERT) Sites in Mouse Brain

Cortical membranes (400 µl; equivalent to 1.25 mg wet weight of tissue/tube) were incubated with 50 µl of [$^3$H] citalopram at a single concentration of 1.3 nM and either 50 µL of buffer (total binding) or 50 µL of paroxetine (0.5 µM; non-specific binding) for 1 h at 27° C. For each animal, three tubes were used for the determination of total binding and three tubes were used for the determination of non-specific binding.

[³H] Nisoxetine Binding to Norepinephrine Transporter (NET) Sites in Mouse Brain Cortical membranes (400 µl; equivalent to 6.0 mg wet weight of tissue/tube) were incubated with 50 µl of [³H] nisoxetine at a single concentration of 0.6 nM and either 50 µl of buffer (total binding) or 50 µl of mazindol (1 µM; non-specific binding) for 4 h at 4° C. For each animal, three tubes were used for the determination of total binding and three tubes were used for the determination of non-specific binding.

[³H] WIN 35428 Binding to DA Transporter (DAT) Sites in Mouse Brain

Striatal membranes (200 µl; equivalent to 2 mg wet weight of tissue/tube) were incubated with 25 µl of [³H] WIN 35428 at a single concentration of 24 nM and either 25 µl of buffer (total binding) or 25 µL of GBR12935 (1 µM; non-specific binding) for 2 h at 4° C. For each animal, two tubes were used for the determination of total binding and two tubes for the determination of non-specific binding.

Membrane bound radioactivity was recovered by filtration under vacuum through Skatron 11731 filters, presoaked in 0.5% PEI, using a Skatron cell harvester. Filters were rapidly washed with ice-cold phosphate buffer and radioactivity (dpm) was determined by liquid scintillation counting (1 ml Packard MV Gold scintillator).

3.3. Data Analysis

A value for specific binding (dpm) was generated by the subtraction of mean non-specific binding (dpm) from mean total binding (dpm) for each animal. Data are presented as mean specific binding (dpm) and as a percentage of the vehicle-treated control taken as 100%.

3.4. Results Summary

Ex vivo SERT, NET and DAT binding/receptor occupancy data were generated for selected compounds of the invention. Results showed that the compounds exhibited varying SERT, NET and DAT inhibition ratios.

Example 4

In Vivo Analyses

4.1. Rat Forced Swim Test

The method, which detects antidepressant activity, followed that described by Porsolt et al (*Eur. J. Pharmacol.*, 47, 379-391, 1978) and modified by Lucki et al. (*Psychopharm.*, 121, 66-72, 1995). Rats forced to swim in a situation from which they cannot escape rapidly become immobile. Antidepressants decrease the duration of immobility. In addition, distinct patterns of active behaviors are produced by antidepressants that selectively inhibit norepinephrine (NE) and serotonin (5-HT) uptake in this test. Selective NE reuptake inhibitors decrease immobility by increasing climbing behaviors whereas selective 5-HT reuptake inhibitors decrease immobility by increasing swimming behaviors.

Rats were individually placed in a cylinder (Height=40 cm; Diameter=20 cm) containing 22 cm water (25° C.) for 15 minutes on the first day of the experiment (Session 1) and were then put back in the water 24 hours later for a 5 minute test (Session 2). The sessions were videotaped and duration of immobility as well as swimming and climbing behaviors during the 5 minute test were measured. Twelve rats were tested in each group. The test was performed blind. Compounds were typically evaluated at 3 doses (1-30 mg/kg), administered orally 2 times: 24 hours and 30-60 minutes before the test (Session 2), and compared with a vehicle control group. Desipramine (20 mg/kg i.p.), administered under the same experimental conditions, was used as the positive reference substance.

Data were analyzed by one way analysis of variance (ANOVA) followed by post-hoc comparisons where appropriate. An effect will be considered significant if $p<0.05$. Data are represented as the mean and standard error to the mean (s.e.m). Tested compounds exhibited antidepressant-like effects with MED's in the range of 10-30 mg/kg, PO. The decrease in immobility produced by these compounds appeared to be due to increases in swimming and climbing behaviors indicative of mixed transporter activity (i.e., SNRI profiles).

4.2. Mouse Tail Suspension Test

The method, which detects antidepressant activity, follows that described by Stem et al (*Psychopharmacology,* 85, 367-370, 1985). Rodents, suspended by the tail, rapidly become immobile. Antidepressants decrease the duration of immobility.

The behavior of the animal was recorded automatically for 5 minutes using a computerized device (Med-Associates Inc.) similar to that developed by Steru et al (*Prog. Neuropsychopharmacol. Exp. Psychiatry,* 11, 659-671, 1987). Ten to twelve mice were tested in each group. The test was performed blind. Compounds were typically evaluated at 3 doses (1-30 mg/kg), administered orally one time: 30-60 minutes before the test, and compared with a vehicle control group. Desipramine (100 mg/kg), administered under the same experimental conditions, was used as the positive reference substance.

Data were analyzed by one way analysis of variance (ANOVA) followed by post-hoc comparisons where appropriate. An effect was considered significant if $p<0.05$. Data are represented as the mean and standard error to the mean (s.e.m). Results showed that tested compounds exhibited an antidepressant-like profile (i.e., significantly decreased immobility time) with MED's in the range of 3-30 mg/kg, PO.

4.3. Locomotor Activity

In order to ensure effects of the compounds on immobility time were not related to a general stimulant effect on baseline motor activity, locomotor activity was assessed using photocell monitored cages (Med-Associates Inc.). Each test chamber was equipped with infrared photocell beams to measure movement of the animals. Horizontal and vertical activity were measured Rats or mice were pretreated with vehicle or test compounds and placed back in home cage, following which they will be individually placed in locomotor cages and activity was monitored in 5 minute intervals for up to 60 min.

Data were analyzed by one way analysis of variance (ANOVA) followed by post-hoc comparisons where appropriate. An effect was considered significant if $p<0.05$. Data are represented as the mean and standard error to the mean (s.e.m). At doses active in the tail suspension test, no change or a decrease in baseline motor activity was observed indicating that antidepressant-like activity was not due to a general stimulant effect.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

What is claimed is:

1. A compound having a structure of formula (I) or a pharmaceutically acceptable salt, solvate, enantiomer, diastereomer, racemic mixture, enantiomerically enriched mixture, or enantiomerically pure form thereof:

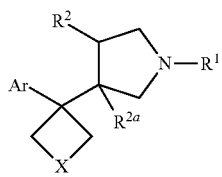
(I)

wherein $R^1$ is selected from H, $C_1$-$C_3$ substituted or unsubstituted alkyl and $C_1$-$C_3$ substituted or unsubstituted heteroalkyl;

$R^2$ and $R^{2a}$ are independently selected from H, $C_1$-$C_3$ substituted or unsubstituted alkyl, $C_1$-$C_3$ substituted or unsubstituted heteroalkyl, and $OR^3$ $R^3$ is selected from H, $C_1$-$C_3$ substituted or unsubstituted alkyl and $C_1$-$C_3$ substituted or unsubstituted heteroalkyl;

$R^5$ is selected from H, $C_1$-$C_3$ substituted or unsubstituted alkyl, $C_1$-$C_3$ substituted or unsubstituted heteroalkyl, and $OR^6$ $R^6$ is selected from H, $C_1$-$C_3$ substituted or unsubstituted alkyl and $C_1$-$C_3$ substituted or unsubstituted heteroalkyl

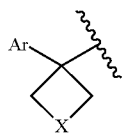

is selected from:

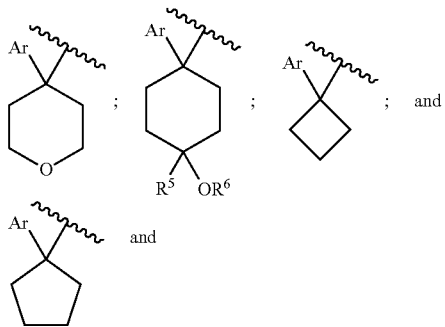

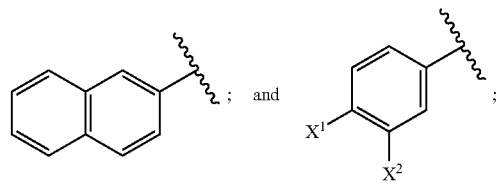

Ar is selected from wherein $X^1$ and $X^2$ are independently selected from H and halogen with the proviso that at least one of $X^1$ and $X^2$ is halogen.

2. A compound of claim 1, selected from

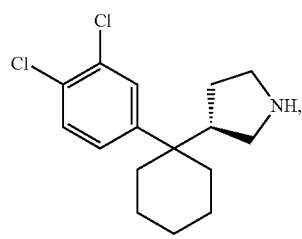

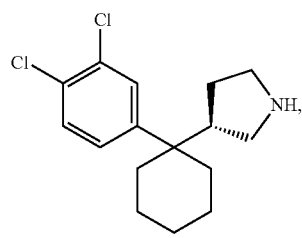

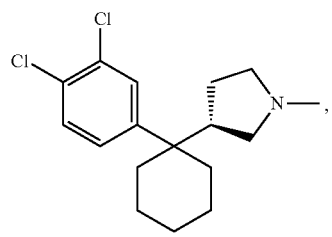

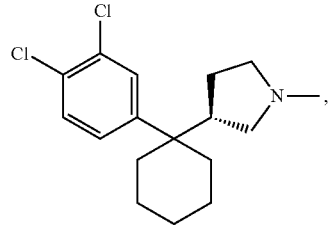

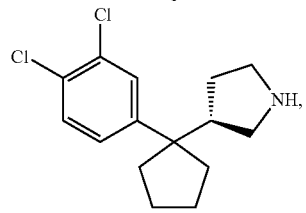

87
-continued
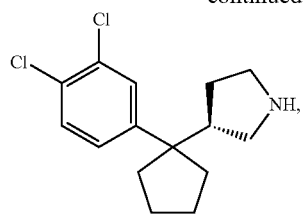
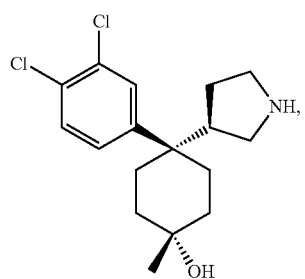
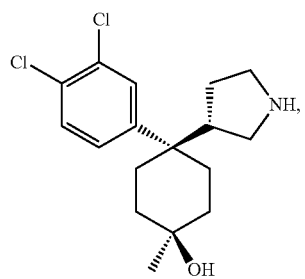
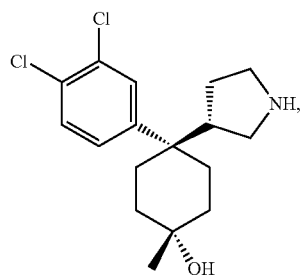
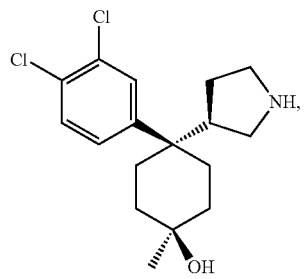
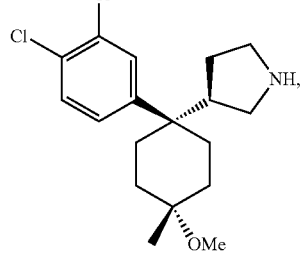
88
-continued
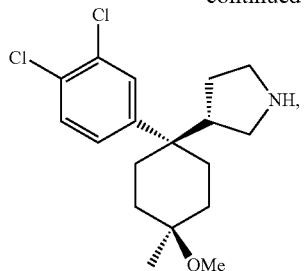
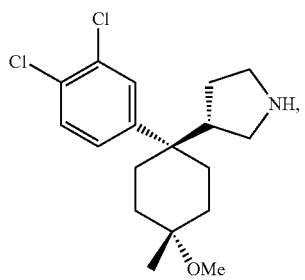
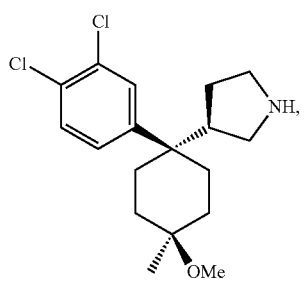
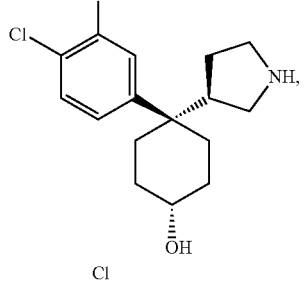
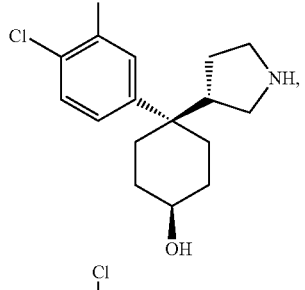
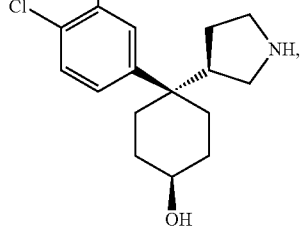

-continued
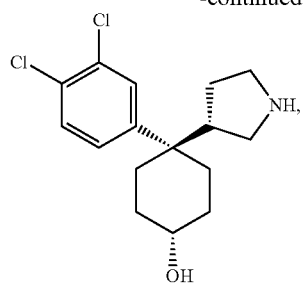
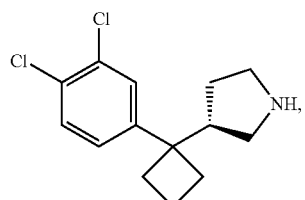
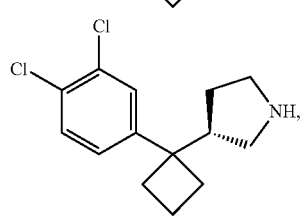
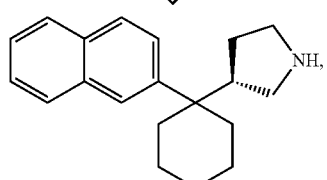
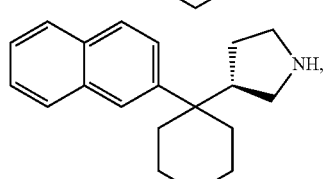
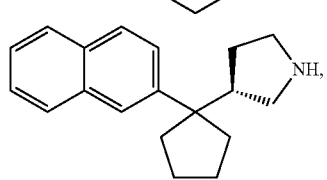
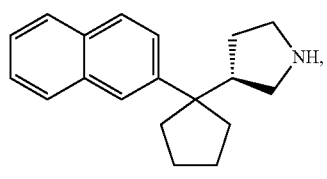
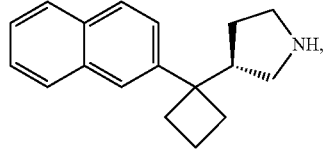
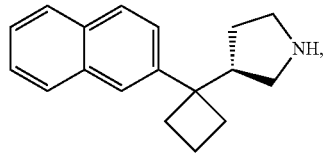
-continued
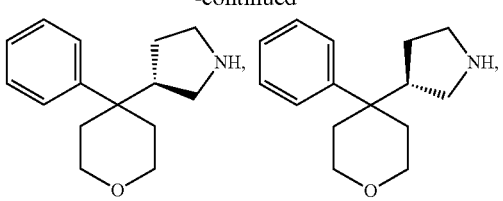
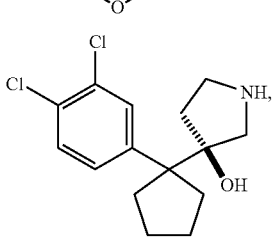
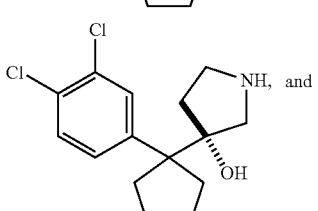
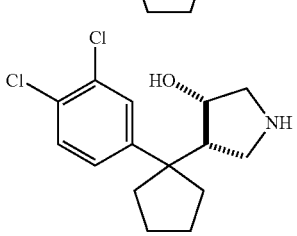
or a pharmaceutically acceptable salt or solvate thereof.
3. A compound of claim 2, selected from
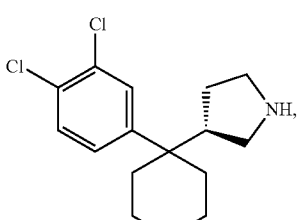
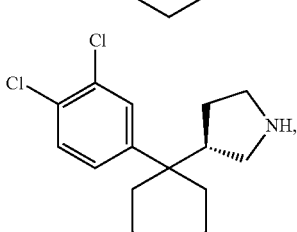
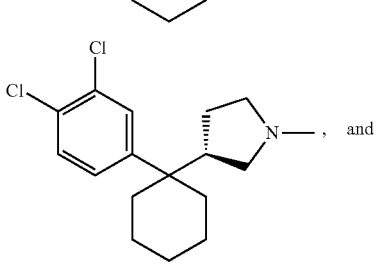

-continued
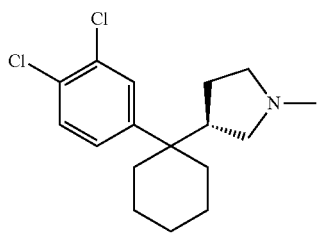
or a pharmaceutically acceptable salt or solvate thereof.
4. A compound of claim 2, selected from
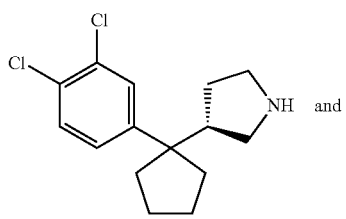 and
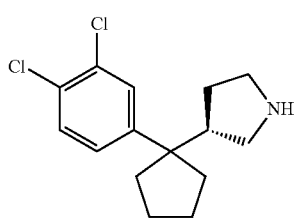
or a pharmaceutically acceptable salt or solvate thereof.
5. A compound of claim 2, selected from
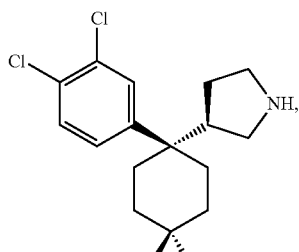
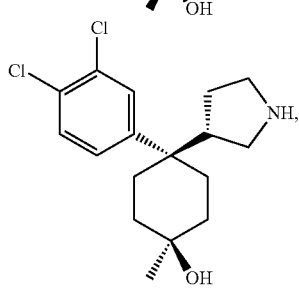
-continued
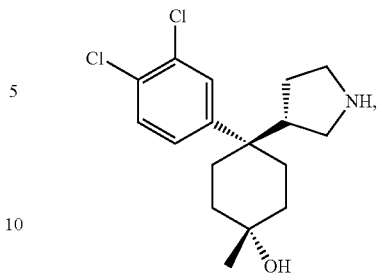
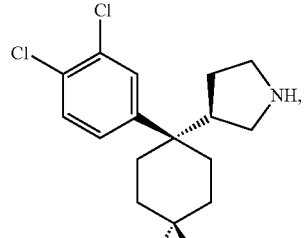
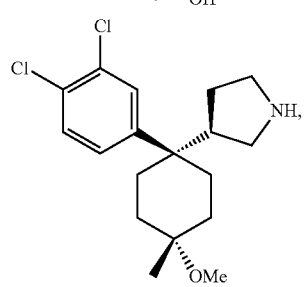
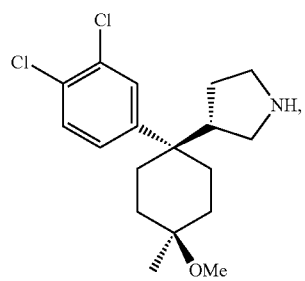
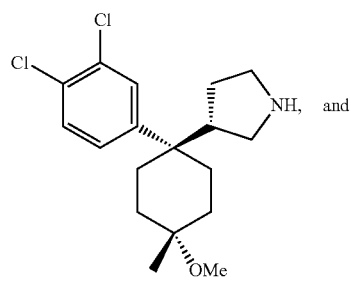 and
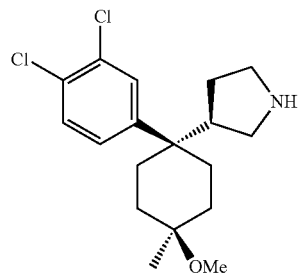
or a pharmaceutically acceptable salt or solvate thereof.

6. A compound of claim 2, selected from

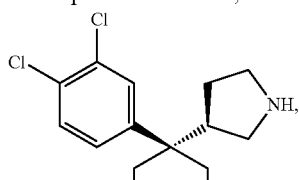

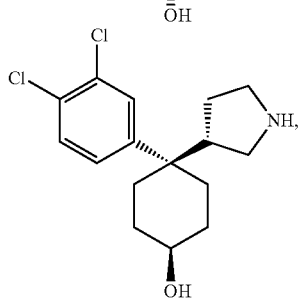

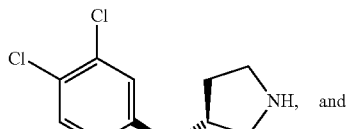

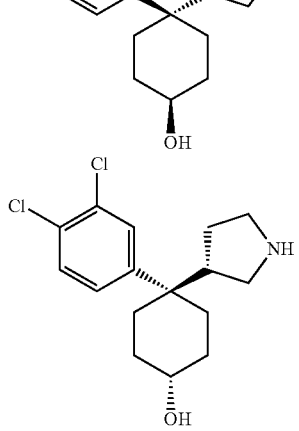

or a pharmaceutically acceptable salt or solvate thereof.

7. A compound of claim 2, selected from

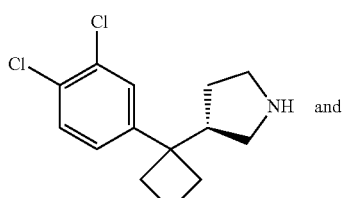

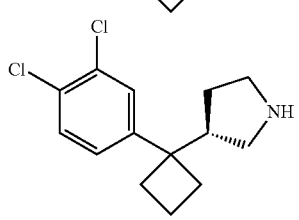

or a pharmaceutically acceptable salt or solvate thereof.

8. A compound of claim 2, selected from

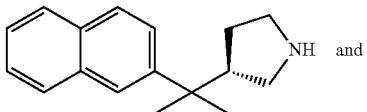

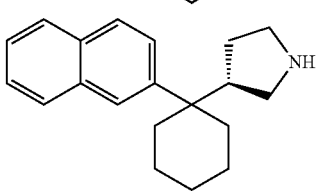

or a pharmaceutically acceptable salt or solvate thereof.

9. A compound of claim 2, selected from

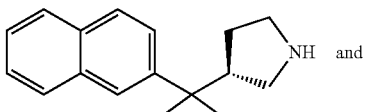

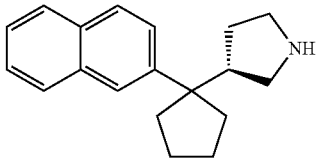

or a pharmaceutically acceptable salt or solvate thereof.

10. A compound of claim 2, selected from

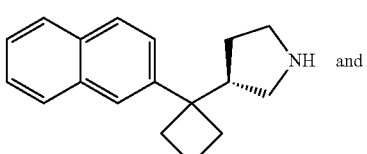

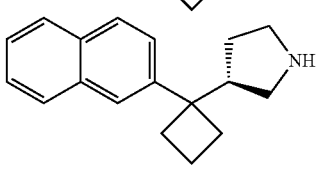

or a pharmaceutically acceptable salt or solvate thereof.

11. A compound of claim 2, selected from

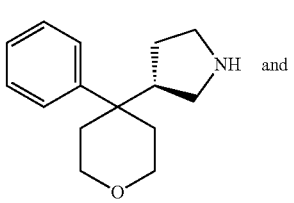

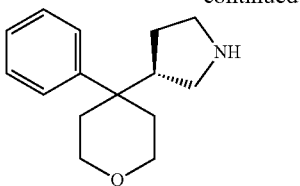

or a pharmaceutically acceptable salt or solvate thereof.

12. A compound of claim 2, selected from

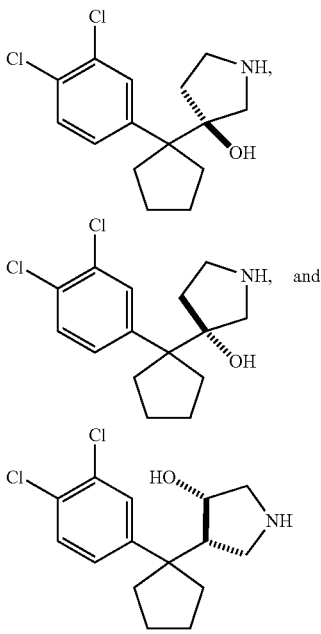

or a pharmaceutically acceptable salt or solvate thereof.

13. A pharmaceutical composition comprising a compound of claim 1 or a pharmaceutically acceptable salt, solvate, enantiomer, diastereomer, racemic mixture, enantiomerically enriched mixture, or enantiomerically pure form thereof, and a pharmaceutically acceptable carrier.

14. A method of inhibiting binding of a monoamine transporter ligand to a monoamine transporter, comprising contacting the monoamine transporter with a compound of claim 1, or a pharmaceutically acceptable salt, solvate, enantiomer, diastereomer, racemic mixture, enantiomerically enriched mixture, or enantiomerically pure form thereof.

15. The method of claim 14, wherein the monoamine transporter is selected from serotonin transporter (SERT), dopamine transporter (DAT), norepinephrine transporter (NET) and combinations thereof.

16. A method of inhibiting the activity of at least one monoamine transporter, comprising contacting the monoamine transporter with a compound of claim 1, or a pharmaceutically acceptable salt, solvate, enantiomer, diastereomer, racemic mixture, enantiomerically enriched mixture, or enantiomerically pure form thereof.

17. The method of claim 16, wherein the monoamine transporter is selected from serotonin transporter (SERT), dopamine transporter (DAT), norepinephrine transporter (NET) and combinations thereof.

18. A method of inhibiting uptake of at least one monoamine by a cell, comprising contacting said cell with a compound of claim 1, or a pharmaceutically acceptable salt, solvate, enantiomer, diastereomer, racemic mixture, enantiomerically enriched mixture, or enantiomerically pure form thereof.

19. The method of claim 18, wherein the monoamine is selected from serotonin, dopamine, norepinephrine and combinations thereof.

20. The method of claim 18, wherein the cell is a neuronal cell.

21. A method of treating a central nervous system disorder, comprising administering to a subject in need thereof a therapeutically effective amount of a compound of claim 1, or a pharmaceutically acceptable salt, solvate, enantiomer, diastereomer, racemic mixture, enantiomerically enriched mixture, or enantiomerically pure form thereof.

22. The method of claim 21, wherein said central nervous system disorder is selected from depression, cognitive deficit, fibromyalgia, pain, sleep disorder, attention deficit disorder (ADD), attention deficit hyperactivity disorder (ADHD), restless leg syndrome, schizophrenia, anxiety, obsessive compulsive disorder, posttraumatic stress disorder, premenstrual dysphoria, and neurodegenerative disease.

23. The method of claim 21, wherein the central nervous system disorder is selected from major depressive disorder, unipolar depression, bipolar disorder, seasonal affective disorder, and dysthymia.

24. The method of claim 21, wherein the central nervous disorder is Parkinson's disease.

25. The method of claim 21, wherein said central nervous system disorder is sleep apnea.

26. The method of claim 21, wherein said central nervous system disorder is neuropathic pain.

* * * * *